(12) United States Patent
Macdonald et al.

(10) Patent No.: US 6,740,666 B2
(45) Date of Patent: May 25, 2004

(54) SUBSTITUTED 8-ARYLQUINOLINE PHOSPHODIESTERASE-4 INHIBITORS

(75) Inventors: Dwight Macdonald, L'Ile Bizard (CA); Helene Perrier, Burlingame, CA (US); Roch Thibert, Outremont (CA); Guo-Jie Ho, Scotch Plains, NJ (US); Anant Vailaya, North Brunswick, NJ (US); David Conlon, Plainsboro, NJ (US); Elizabeth Kwong, Pointe-Claire (CA); Sophie-Dorothee Clas, Montreal (CA)

(73) Assignees: Merck & Co., Inc., Rahway, NJ (US); Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 10/040,993

(22) Filed: Nov. 9, 2001

(65) Prior Publication Data

US 2002/0143032 A1 Oct. 3, 2002

Related U.S. Application Data

(60) Provisional application No. 60/256,803, filed on Dec. 20, 2000.

(51) Int. Cl.[7] .................. A61K 31/47; C07D 413/10
(52) U.S. Cl. ......................... 514/314; 546/172
(58) Field of Search ................. 546/172, 173; 514/314

(56) References Cited

U.S. PATENT DOCUMENTS

| | | |
|---|---|---|
| 5,340,827 A | 8/1994 | Beeley et al. |
| 5,491,147 A | 2/1996 | Boyd et al. |
| 5,550,137 A | 8/1996 | Beeley et al. |
| 5,580,888 A | 12/1996 | Warrellow et al. |
| 5,608,070 A | 3/1997 | Alexander et al. |
| 5,622,977 A | 4/1997 | Warrellow et al. |
| 5,633,257 A | 5/1997 | Warrellow et al. |
| 5,679,712 A | 10/1997 | Schwark et al. |
| 5,693,672 A | 12/1997 | Weichert et al. |
| 5,736,297 A | 4/1998 | Roeschert et al. |
| 5,739,144 A | 4/1998 | Warrellow et al. |
| 5,747,541 A | 5/1998 | Weichert et al. |
| 5,776,958 A | 7/1998 | Warrellow et al. |
| 5,780,477 A | 7/1998 | Head et al. |
| 5,780,478 A | 7/1998 | Alexander et al. |
| 5,786,354 A | 7/1998 | Warrellow et al. |
| 5,798,373 A | 8/1998 | Warrellow |
| 5,849,770 A | 12/1998 | Head et al. |
| 5,859,034 A | 1/1999 | Warrellow et al. |
| 5,866,593 A | 2/1999 | Warrellow et al. |
| 5,891,896 A | 4/1999 | Warrellow et al. |
| 6,011,063 A | 1/2000 | Weichert et al. |
| 6,410,563 B1 * | 6/2002 | Deschenes et al. ......... 514/314 |

FOREIGN PATENT DOCUMENTS

| | | |
|---|---|---|
| EP | 1 052 254 A1 | 1/1999 |
| WO | WO 94/22852 | 10/1994 |
| WO | WO 95/35283 | 12/1995 |
| WO | WO 96/00215 | 1/1996 |
| WO | WO 98/25883 | 6/1999 |
| WO | WO 01/56151 A1 | 6/2001 |

OTHER PUBLICATIONS

C. Burnouf et al., Ann. Rep. In Med. Chem., 33:91–109(1998).
B. Hughes et al., Dr. J. Pharmacol., 118:1183–1191(1996).
M. J. Perry et al., Cell Biochem. Biophys., 29:113–132(1998).
S. B. Christensen et al., J. Med Chem., 41:821–835(1998).
M. D. Houslay et al., Adv. In Pharmacol., 44:225–342(1998).
D. Spina et al., Adv. In Pharmacol., 44:33–89(1998).
A. H. Cook et al., J. Chem. Soc. 413–417(1943).
K. Manabe et al., J. Org. Chem., 58(24):6692–6700(1993).
K. Manabe et al., J. Am. Chem. Soc., 115(12): 5324–5325(1993).
K. Manabe et al., J. Am. Chem. Soc., 114(17): 6940–6941(1999).
Macdonald, D., et al., J. Med. Chem., (2000) p. 3820–3823, vol. 43 No. 21.

* cited by examiner

*Primary Examiner*—Bernard Dentz
(74) *Attorney, Agent, or Firm*—Curtis C. Panzer; David L. Rose

(57) ABSTRACT

Novel sulfuric acid, methanesulfonic acid, p-toluenesulfonic acid, 2-naphthalenesulfonic acid, hydrochloride acid, or benzenesulfonic acid salts of substituted 8-arylquinolines, wherein the aryl group at the 8-position contains a substituent substituted-alkenyl group, are PDE4 inhibitors.

4 Claims, 6 Drawing Sheets

SUBSTITUTED 8-ARYLQUINOLINE PHOSPHODIESTERASE-4 INHIBITORS

CROSS-REFERENCE TO RELATED APPLICATIONS

This application claims the benefit of U.S. Provisional Application No. 60/256,803, filed on Dec. 20, 2000.

BACKGROUND OF THE INVENTION

1. Field of the Invention

The present invention is directed to compounds that are substituted 8-arylquinolines. In particular, this invention is directed to salts of substituted 8-arylquinolines which are phosphodiesterase-4 inhibitors wherein the aryl group at the 8-position contains a substituent substituted-alkenyl group.

2. Related Background

Hormones are compounds that variously affect cellular activity. In many respects, hormones act as messengers to trigger specific cellular responses and activities. Many effects produced by hormones, however, are not caused by the singular effect of just the hormone. Instead, the hormone first binds to a receptor, thereby triggering the release of a second compound that goes on to affect the cellular activity. In this scenario, the hormone is known as the first messenger while the second compound is called the second messenger. Cyclic adenosine monophosphate (adenosine 3', 5'-cyclic monophosphate, "cAMP" or "cyclic AMP") is known as a second messenger for hormones including epinephrine, glucagon, calcitonin, corticotrophin, lipotropin, luteinizing hormone, norepinephrine, parathyroid hormone, thyroid-stimulating hormone, and vasopressin. Thus, cAMP mediates cellular responses to hormones. Cyclic AMP also mediates cellular responses to various neurotransmitters.

Phosphodiesterases ("PDE") are a family of enzymes that metabolize 3',5' cyclic nucleotides to 5' nucleoside monophosphates, thereby terminating cAMP second messenger activity. A particular phosphodiesterase, phosphodiesterase-4 ("PDE4", also known as "PDE-IV"), which is a high affinity, cAMP specific, type IV PDE, has generated interest as potential targets for the development of novel anti-asthmatic and anti-inflammatory compounds. PDE4 is known to exist as at lease four isoenzymes, each of which is encoded by a distinct gene. Each of the four known PDE4 gene products is believed to play varying roles in allergic and/or inflammatory responses. Thus, it is believed that inhibition of PDE4, particularly the specific PDE4 isoforms that produce detrimental responses, can beneficially affect allergy and inflammation symptoms. It would be desirable to provide novel compounds and compositions that inhibit PDE4 activity.

A major concern with the use of PDE4 inhibitors is the side effect of emesis which has been observed for several candidate compounds as described in C. Burnouf et al., ("Burnouf"), Ann. Rep. In Med. Chem., 33:91–109(1998). B. Hughes et al., Br. J. Pharmnacol., 118:1183–1191(1996); M. J. Perry et al., Cell Biochem. Biophys., 29:113–132(1998); S. B. Christensen et al., J. Med. Chem., 41:821–835(1998); and Burnouf describe the wide variation of the severity of the undesirable side effects exhibited by various compounds. As described in M. D. Housely et al., Adv. In Pharmacol., 44:225–342(1998) and D. Spina et al., Adv. In Pharmacol., 44:33–89(1998), there is great interest and research of therapeutic PDE4 inhibitors.

International Patent Publication W09422852 describes quinolines as PDE4 inhibitors.

A. H. Cook, et al., J. Chem. Soc., 413–417(1943) describes gammapyridylquinolines. Other quinoline compounds are described in Kei Manabe et al., J. Org. Chem., 58(24):6692–6700(1993); Kei Manabe et al., J. Am. Chem. Soc., 115(12):5324–5325(1993); and Kei Manabe et al., J. Am. Chem. Soc., 114(17):6940–6941(1992).

Compounds that include ringed systems are described by various investigators as effective for a variety of therapies and utilities. For example, International Patent Publication No. WO 98/25883 describes ketobenzarnides as calpain inhibitors, European Patent Publication No. EP 811610 and U.S. Pat. Nos. 5,679,712, 5,693,672 and 5,747,541 describe substituted benzoylguanidine sodium channel blockers, U.S. Pat. No. 5,736,297 describes ring systems useful as a photosensitive composition.

U.S. Pat. Nos. 5,491,147, 5,608,070, 5,622,977, 5,739,144, 5,776,958, 5,780,477, 5,786,354, 5,798,373, 5,849,770, 5,859,034, 5,866,593, 5,891,896, and International Patent Publication WO 95/35283 describe PDE4 inhibitors that are tri-substituted aryl or heteroaryl phenyl derivatives. U.S. Pat. No. 5,580,888 describes PDE4 inhibitors that are styryl derivatives. U.S. Pat. No. 5,550,137 describes PDE4 inhibitors that are phenylaminocarbonyl derivatives. U.S. Pat. No. 5,340,827 describes PDE4 inhibitors that are phenylcarboxamide compounds. U.S. Pat. No. 5,780,478 describes PDE4 inhibitors that are tetra-substituted phenyl derivatives. International Patent Publication WO 96/00215 describes substituted oxime derivatives useful as PDE4 inhibitors. U.S. Pat. No. 5,633,257 describes PDE4 inhibitors that are cyclo(alkyl and alkenyl)phenyl-alkenyl (aryl and heteroaryl) compounds.

However, there remains a need for novel compounds and compositions that therapeutically inhibit PDE4 with minimal side effects.

SUMMARY OF THE INVENTION

The present invention is directed to novel salts of novel substituted 8-arylquinolines that are PDE4 inhibitors, wherein the aryl group at the 8-position is substituted by a substituted-alkenyl group. This invention also provides a pharmaceutical composition which includes an effective amount of the novel salts of novel substituted 8-arylquinolines and a pharmaceutically acceptable carrier. This invention further provides a method of treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues by the administration of an effective amount of the novel salt of a substituted 8-arylquinoline or a precursor salt compound which forms in vivo the novel substituted 8-arylquinoline.

DETAILED DESCRIPTION OF THE INVENTION

Figure 1:
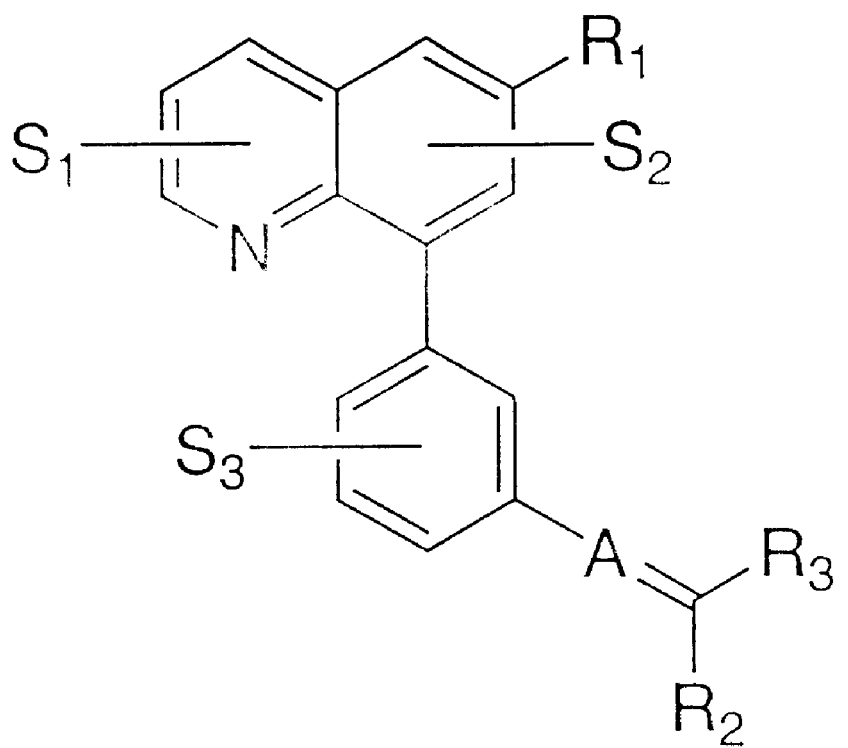
FIG. 1 is a chemical schematic drawing of the general structure of the compounds from which the present invention forms novel salts.

A compound of this invention is a pharmaceutically acceptable salt of a compound represented by Formula (I):

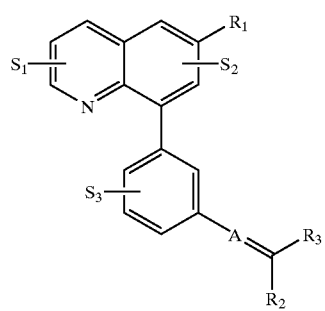

(I)

wherein
$S_1$, $S_2$, and $S_3$ are independently H, —OH, halogen, —$C_1$–$C_6$alkyl, —$NO_2$, —CN, or —$C_1$–$C_6$alkoxy, wherein the alkyl and alkoxy groups are optionally substituted with 1–5 substituents; wherein each substituent is independently a halogen or OH;

$R_1$ is a H, OH, halogen, carbonyl, or —$C_1$–$C_6$alkyl, -cyclo$C_3$–$C_6$alkyl, —$C_1$–$C_6$alkenyl, —$C_1$–$C_6$alkoxy, aryl, heteroaryl, —CN, -heterocyclo$C_3$–$C_6$alkyl, -amino, —$C_1$–$C_6$alkylamino, —($C_1$–$C_6$alkyl) ($C_1$–$C_6$alkyl)amino, —$C_1$–$C_6$alkyl(oxy)$C_1$–$C_6$alkyl, —C(O)NH(aryl), —C(O)NH(heteroaryl), —$SO_n$NH (aryl), —$SO_n$NH(heteroaryl), —$SO_n$NH($C_1$–$C_6$alkyl), —C(O)N($C_0$–$C_6$alkyl)($C_0$–$C_6$alkyl), —NH—$SO_n$—($C_1$–$C_6$alkyl), —$SO_n$—($C_1$–$C_6$alkyl), —($C_1$–$C_6$-alkyl)—O—C(CN)-dialkylarnino, or —($C_1$–$C_6$-alkyl)—$SO_n$—($C_1$–$C_6$alkyl) group, wherein any of the groups is optionally substituted with 1–5 substituents; wherein each substituent is independently a halogen, —OH, —CN, —$C_1$–$C_6$alkyl, -cyclo$C_3$–$C_6$alkyl, —C(O)(heterocyclo$C_3$–$C_6$alkyl), —C(O)—O—($C_0$–$C_6$alkyl), —C(O)-aryloxy, —$C_1$–$C_6$alkoxy, —($C_0$–$C_6$alkyl)($C_0$–$C_6$alkyl)amino, cycloalkyloxy, acyl, acyloxy, -cyclo$C_3$–$C_6$alkyl, heterocyclo$C_3$–$C_6$alkyl, aryl, heteroaryl, carbonyl, carbamoyl, or —$SO_n$—($C_1$–$C_6$alkyl);

A is CH, C-ester, or C—$R_4$;

$R_2$ and $R_3$ independently is an aryl, heteroaryl, H, halogen, —CN, —$C_1$–$C_6$alkyl, heterocyclo$C_3$–$C_6$alkyl, —$C_1$–$C_6$alkoxy, carbonyl, carbamoyl, —C(O)OH, —($C_1$–$C_6$alkyl)—$SO_n$—($C_1$–$C_6$alkyl), —C(O)N ($C_0$–$C_6$alkyl)($C_0$–$C_6$alkyl), or —$C_1$–$C_6$alkylacylamino group, wherein any of the groups is optionally substituted with 1–5 substituents, wherein each substituent is independently an aryl, heteroaryl, halogen, —$NO_2$, —C(O)OH, carbonyl, —CN, —$C_1$–$C_6$alkyl, —$SO_n$—($C_1$–$C_6$alkyl), —$SO_n$—(aryl), aryloxy, -heteroaryloxy, $C_1$–$C_6$alkoxy, N-oxide, —C(O)-heterocyclo$C_3$–$C_6$alkyl, —NH-cyclo$C_3$–$C_6$alkyl, amino, —OH, or —($C_0$–$C_6$alkyl)($C_0$–$C_6$alkyl)amino, —C(O)—N($C_0$–$C_6$alkyl)($C_0$–$C_6$alkyl) substituent group, wherein each substituent group independently is optionally substituted with —OH, $C_1$–$C_6$alkoxy, —$C_1$–$C_6$alkyl, -cyclo$C_3$–$C_6$alkyl, aryloxy, —C(O)OH, —C(O)O($C_1$–$C_6$alkyl), halogen, —$NO_2$, —CN, —$SO_n$—($C_1$–$C_6$alkyl), or —C(O)—N($C_0$–$C_6$alkyl) ($C_0$–$C_6$alkyl);

one of $R_2$ and $R_3$ must be an aryl or heteroaryl, optionally substituted;

when $R_2$ and $R_3$ are both an aryl or heteroaryl, then $R_2$ and $R_3$ may be optionally connected by a thio, oxy, or ($C_1$–$C_4$alkyl) bridge to form a fused three ring system;

$R_4$ is an aryl, —$C_1$–$C_6$alkyl, heteroaryl, —CN, carbonyl, carbamoyl, —($C_1$–$C_6$alkyl)—$SO_n$—($C_1$–$C_6$alkyl), —C(O)N($C_0$–$C_6$alkyl)($C_0$–$C_6$alkyl), or —$C_1$–$C_6$alkylacylamino group, wherein any of the groups is optionally substituted with 1–5 substituents, wherein each substituent is independently a carbonyl, —CN, halogen, —C(O)($C_0$–$C_6$alkyl), —C(O)O ($C_0$–$C_6$alkyl), —$C_1$–$C_6$alkyl, —$SO_n$—($C_1$–$C_6$alkyl), —OH, $C_1$–$C_6$alkoxy, or —($C_0$–$C_6$alkyl)($C_0$–$C_6$alkyl) amino, group;

n is independently 0, 1, or 2; and $R_2$ or $R_3$ may optionally be joined to $R_4$ by a bond to form a ring.

In one aspect, the compound of this invention is a pharmaceutically acceptable sulfuric acid, methanesulfonic acid, p-toluenesulfonic acid, 2-naphthalenesulfonic acid, hydrochloride acid, or benzenesulfonic acid salt of a compound represented by Formula (I), wherein $S_1$, $S_2$, and $S_3$ are independently H, —OH, halogen, —$C_1$–$C_6$alkyl, —$NO_2$, —CN, or —$C_1$–$C_6$alkoxy, wherein the alkyl and alkoxy groups are optionally substituted with 1–5 substituents; wherein each substituent is independently a halogen or OH;

$R_1$ is a H, OH, halogen, carbonyl, or —$C_1$–$C_6$alkyl, -cyclo$C_3$–$C_6$alkyl, —$C_1$–$C_6$alkenyl, —$C_1$–$C_6$alkoxy, aryl, heteroaryl, —CN, -heterocyclo$C_3$–$C_6$alkyl, -amino, —$C_1$–$C_6$alkylamino, —($C_1$–$C_6$alkyl)($C_1$–$C_6$alkyl)amino, —$C_1$–$C_6$alkyl(oxy)$C_1$–$C_6$alkyl, —C(O)NH(aryl), —C(O)NH(heteroaryl), —SO$_n$NH(aryl), —SO$_n$NH(heteroaryl), —SO$_n$NH($C_1$–$C_6$alkyl), —C(O)N($C_0$–$C_6$alkyl)($C_0$–$C_6$alkyl), —NH—SO$_n$—($C_1$–$C_6$alkyl), —SO$_n$—($C_1$–$C_6$alkyl), —($C_1$–$C_6$alkyl)—O—C(CN)-dialkylamino, or —($C_1$–$C_6$alkyl)—SO$_n$—($C_1$–$C_6$alkyl) group, wherein any of the groups is optionally substituted with 1–5 substituents; wherein each substituent is independently a halogen, —OH, —CN, —$C_1$–$C_6$alkyl, -cyclo$C_3$–$C_6$alkyl, —C(O)(heterocyclo$C_3$–$C_6$alkyl), —C(O)—O—($C_0$–$C_6$alkyl), —C(O)-aryloxy, —$C_1$–$C_6$alkoxy, —($C_0$–$C_6$alkyl)($C_0$–$C_6$alkyl)amino, cycloalkyloxy, acyl, acyloxy, -cyclo$C_3$–$C_6$alkyl, heterocyclo$C_3$–$C_6$alkyl, aryl, heteroaryl, carbonyl, carbamoyl, or —SO$_n$—($C_1$–$C_6$alkyl);

A is CH, C-ester, or C—$R_4$;

$R_2$ and $R_3$ independently is an aryl, heteroaryl, H, halogen, —CN, —$C_1$–$C_6$alkyl, heterocyclo$C_{3-6}$alkyl, —$C_1$–$C_6$alkoxy, carbonyl, carbamoyl, —C(O)OH, —($C_1$–$C_6$alkyl)—SO$_n$—($C_1$–$C_6$alkyl), —C(O)N($C_0$–$C_6$alkyl)($C_0$–$C_6$alkyl), or —$C_1$–$C_6$alkylacylamino group, wherein any of the groups is optionally substituted with 1–5 substituents, wherein each substituent is independently an aryl, heteroaryl, halogen, —NO$_2$, —C(O)OH, carbonyl, —CN, —$C_1$–$C_6$alkyl, —SO$_n$—($C_1$–$C_6$alkyl), —SO$_n$—(aryl), aryloxy, -heteroaryloxy, $C_1$–$C_6$alkoxy, N-oxide, —C(O)-heterocyclo$C_3$–$C_6$alkyl, —NH-cyclo$C_3$–$C_6$alkyl, amino, —OH, or —($C_0$–$C_6$alkyl)($C_0$–$C_6$alkyl)amino, —C(O)—N($C_0$–$C_6$alkyl)($C_0$–$C_6$alkyl) substituent group, wherein each substituent group independently is optionally substituted with —OH, $C_1$–$C_6$alkoxy, —$C_1$–$C_6$alkyl, -cyclo$C_3$–$C_6$alkyl, aryloxy, —C(O)OH, —C(O)O($C_1$–$C_6$alkyl), halogen, —NO$_2$, —CN, —SO$_n$—($C_1$–$C_6$alkyl), or —C(O)—N($C_0$–$C_6$alkyl)($C_0$–$C_6$alkyl);

one of $R_2$ and $R_3$ must be an aryl or heteroaryl, optionally substituted;

when $R_2$ and $R_3$ are both an aryl or heteroaryl, then $R_2$ and $R_3$ may be optionally connected by a thio, oxy, or ($C_1$–$C_4$alkyl) bridge to form a fused three ring system;

$R_4$ is an aryl, —$C_1$–$C_6$alkyl, heteroaryl, —CN, carbonyl, carbamoyl, —($C_1$–$C_6$alkyl)—SO$_n$—($C_1$–$C_6$alkyl), —C(O)N($C_0$–$C_6$alkyl)($C_0$–$C_6$alkyl), or —$C_1$–$C_6$alkylacylamino group, wherein any of the groups is optionally substituted with 1–5 substituents, wherein each substituent is independently a carbonyl, —CN, halogen, —C(O)($C_0$–$C_6$alkyl), —C(O)O($C_0$–$C_6$alkyl), —$C_1$–$C_6$alkyl, —SO$_n$—($C_1$–$C_6$alkyl), —OH, $C_1$–$C_6$alkoxy, or —($C_0$–$C_6$alkyl)($C_0$–$C_6$alkyl)amino, group;

n is independently 0, 1, or 2; and $R_2$ or $R_3$ may optionally be joined to $R_4$ by a bond to form a ring.

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "cycloalkyloxy" unless specifically stated otherwise includes a cycloalkyl group connected to the oxy connecting atom.

The term "alkoxy" unless specifically stated otherwise includes an alkyl group connected to the oxy connecting atom.

The term "aryl" unless specifically stated otherwise includes multiple ring systems as well as single ring systems such as, for example, phenyl or naphthyl.

The term "aryloxy" unless specifically stated otherwise includes multiple ring systems as well as single ring systems such as, for example, phenyl or naphthyl, connected through the oxy connecting atom to the connecting site.

The term "$C_0$–$C_6$alkyl" includes alkyls containing 6, 5, 4, 3, 2, 1, or no carbon atoms. An alkyl with no carbon atoms is a hydrogen atom substituent or a direct bond—depending on whether the alkyl is a terminus or a bridging moiety.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five membered ring containing from 5 to no carbon atoms.

Examples of heteroaryl include, for example, pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl.

The term "heteroaryloxy" unless specifically stated otherwise describes a heteroaryl group connected through an oxy connecting atom to the connecting site.

Examples of heteroaryl($C_{1-6}$)alkyl include, for example, furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

Examples of heterocyclo$C_{3-7}$alkyl include, for example, azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

Examples of aryl($C_{1-6}$)alkyl include, for example, phenyl($C_{1-6}$)alkyl, and naphthyl($C_{1-6}$)alkyl.

Examples of heterocyclo$C_{3-7}$alkylcarbonyl($C_{1-6}$)alkyl include, for example, azetidinyl carbonyl($C_{1-6}$)alkyl, pyrrolidinyl carbonyl($C_{1-6}$)alkyl, piperidinyl carbonyl($C_{1-6}$)alkyl, piperazinyl carbonyl($C_{1-6}$)alkyl, morpholinyl carbonyl($C_{1-6}$)alkyl, and thiomorpholinyl carbonyl($C_{1-6}$)alkyl.

The term "amine" unless specifically stated otherwise includes primary, secondary and tertiary amines.

Unless otherwise stated, the term "carbamoyl" is used to include —NHC(O)O$C_1$–$C_4$alkyl, and —OC(O)NH$C_1$–$C_4$alkyl.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, the substitution can be made at any of the groups. For example, substituted aryl($C_{1-6}$)alkyl includes substitution on the aryl group as well as substitution on the alkyl group.

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are benzenesulfonic, citric, hydrobromic, hydrochloric, maleic, phosphoric, sulfuric, and tartaric acids.

The pharmaceutical compositions of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) Leukotriene receptor antagonists, ii) Leukotriene biosynthesis inhibitors, iii) corticosteroids, iv) H1 receptor antagonists, v) beta 2 adrenoceptor agonists, vi) COX-2 selective inhibitors, vii) statins, viii) non-steroidal anti-inflammatory drugs ("NSAID"), and ix) M2/M3 antagonists. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.001 mg/kg to about 140 mg/kg of body weight per day are useful in the treatment of conditions such as asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues which are responsive to PDE4 inhibition, or alternatively about 0.05 mg to about 7 g per patient per day. For example, inflammation may be effectively treated by the administration of from about 0.01 mg to 50 mg of the compound per kilogram of body weight per day, or alternatively about 0.5 mg to about 2.5 g per patient per day.

Further, it is understood that the PDE4 inhibiting compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 0.01 mg to about 1000 mg of the active ingredient, typically 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions of this invention have been found to exhibit biological activity as PDE4 inhibitors. Accordingly, another aspect of the invention is the treatment in mammals of, for example, asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues—maladies that are amenable to amelioration through inhibition of the PDE4 isoenzyme and the resulting elevated cCAMP levels—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound of this invention can be utilized in combination with other therapeutic compounds. In particular, the combinations of the PDE4 inhibiting compound of this invention can be advantageously used in combination with i) Leukotriene receptor antagonists, ii) Leukotriene biosynthesis inhibitors, iii) COX-2 selective inhibitors, iv) statins, v) NSAIDs, vi) M2/M3 antagonists, vii) corticosteroids, viii) H1 (histamine) receptor antagonists and ix) beta 2 adrenoceptor agonist.

In another aspect, it was found that the compound of this invention can be formed as a metabolite in the mammalian system. For example, Example 19, (5-{(E)-2-(3-{6-[1-methyl-1-(methylsulfonyl)ethyl]-8-quinolinyl}phenyl)-1-[4-(methylsulfonyl)phenyl]ethenyl}-1,2,4-oxadiazol-3-yl) methanol:

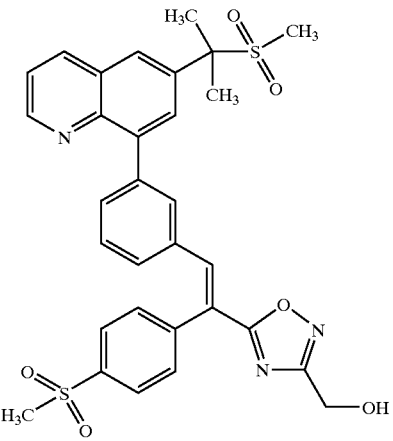

which is a PDE4 inhibitor is formed in vivo as a metabolite when Example 14:

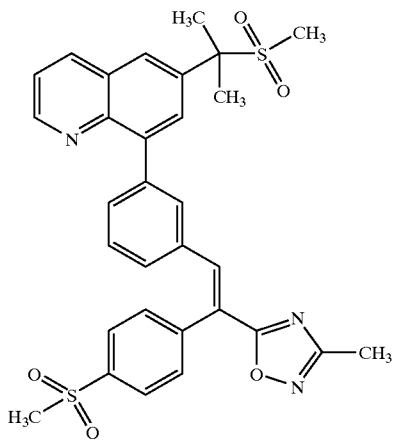

is administered. Accordingly, the present invention includes prodrugs that form PDE4 inhibitors in vivo as a metabolite after administering such prodrugs to a mammal. Further, this invention includes a method of treatment by a step of administering a prodrug to form in vivo an effective amount of a PDE4 inhibitor described by Formula I.

The abbreviations used herein have the following tabulated meanings. Abbreviations not tabulated below have their meanings as commonly used unless specifically stated otherwise.

| | |
|---|---|
| Ac = | acetyl |
| Bn = | benzyl |
| CAMP = | cyclic adenosine-3',5'-monophosphate |
| DBU = | 1,8-diazabicyclo[5.4.0]undec-7-ene |
| DIBAL = | diisobutylaluminum hydride |
| DMAP = | 4-(dimethylamino)pyridine |
| DMF = | N,N-dimethylformamide |
| Et$_3$N = | triethylamine |
| GST = | glutathione transferase |
| HMDS = | hexamethyldisilazide |
| LDA = | lithium diisopropylamide |
| m-CPBA = | metachloroperbenzoic acid |
| MMPP = | monoperoxyphthalic acid |
| MPPM = | monoperoxyphthalic acid, magnesium salt 6H$_2$O |
| Ms = | methanesulfonyl = mesyl = SO$_2$Me |
| MsO = | methanesulfonate = mesylate |

-continued

| | |
|---|---|
| NSAID = | non-steroidal anti-inflammatory drug |
| o-Tol = | ortho-tolyl |
| OXONE ® = | $2KHSO_5 \cdot KHSO_4 \cdot K_2SO_4$ |
| PCC = | pyridinium chlorochromate |
| PDC = | pyridinium dichromate |
| PDE = | phosphodiesterase |
| Ph = | phenyl |
| Phe = | benzenediyl |
| PMB = | para-methoxybenzyl |
| Pye = | pyridinediyl |
| r.t. = | room temperature |
| Rac. = | racemic |
| SAM = | aminosulfonyl or sulfonamide or $SO_2NH_2$ |
| SEM = | 2-(trimethylsilyl)ethoxymethoxy |
| SPA = | scintillation proximity assay |
| TBAF = | tetra-n-butylammonium fluoride |
| Th = | 2- or 3-thienyl |
| TFA = | trifluoroacetic acid |
| TFAA = | trifluoroacetic acid anhydride |
| THF = | teyrahydrofuran |
| Thi = | thiophenediyl |
| TLC = | thin layer chromatography |
| TMS-CN = | trimethylsilyl cyanide |
| TMSI = | trimethylsilyl iodide |
| Tz = | 1H (or 2H)-tetrazol-5-yl |
| CAN = | ceric ammonium nitrate |
| $C_3H_5$ = | allyl |

ALKYL GROUP ABBREVIATIONS

| | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

ASSAYS DEMONSTRATING BIOLOGICAL ACTIVITY

LPS AND FMLP-INDUCED TNF-α AND $LTB_4$ ASSAYS IN HUMAN WHOLE BLOOD

Whole blood provides a protein and cell-rich milieu appropriate for the study of biochemical efficacy of anti-inflammatory compounds such as PDE4-selective inhibitors. Normal non-stimulated human blood does not contain detectable levels of TNF-α and $LTB_4$. Upon stimulation with LPS, activated monocytes express and secrete TNF-α up to 8 hours and plasma levels remain stable for 24 hours. Published studies have shown that inhibition of TNF-α by increasing intracellular cAMP via PDE4 inhibition and/or enhanced adenylyl cyclase activity occurs at the transcriptional level. $LTB_4$ synthesis is also sensitive to levels of intracellular cAMP and can be completely inhibited by PDE4-selective inhibitors. As there is little $LTB_4$ produced during a 24 hour LPS stimulation of whole blood, an additional LPS stimulation followed by fMLP challenge of human whole blood is necessary for $LTB_4$ synthesis by activated neutrophils. Thus, by using the same blood sample, it is possible to evaluate the potency of a compound on two surrogate markers of PDE4 activity in the whole blood by the following procedure.

Fresh blood was collected in heparinized tubes by venipuncture from healthy human volunteers (male and female). These subjects had no apparent inflammatory conditions and had not taken any NSAIDs for at least 4 days prior to blood collection. 500 μL aliquots of blood were pre-incubated with either 2 μL of vehicle (DMSO) or 2 μL of test compound at varying concentrations for 15 minutes at 37° C. This was followed by the addition of either 10μL vehicle (PBS) as blanks or 10 μL LPS (1 μg/mL final concentration, #L-2630 (Sigma Chemical Co., St. Louis, Mo.) from E. coli, serotype 0111:B4; diluted in 0.1% w/v BSA (in PBS)). After 24 hours of incubation at 37° C., another 10 μL of PBS (blank) or 10 μL of LPS (1 μg/L final concentration) was added to blood and incubated for 30 minutes at 37° C. The blood was then challenged with either 10 μL of PBS (blank) or 10 μL of fMLP (1 μM final concentration, #F-3506 (Sigma); diluted in 1% w/v BSA (in PBS)) for 15 minutes at 37° C. The blood samples were centrifuged at 1500×g for 10 minutes at 4° C. to obtain plasma. A 50 μL aliquot of plasma was mixed with 200 μL methanol for protein precipitation and centrifuged as above. The supernatant was assayed for $LTB_4$ using an enzyme immunoassay kit (#520111 from Cayman Chemical Co., Ann Arbor, Mich.) according to the manufacturer's procedure. TNF-α was assayed in diluted plasma (in PBS) using an ELISA kit (Cistron Biotechnology, Pine Brook, N.J.) according to manufacturer's procedure. The $IC_{50}$ values of Examples 1–42 generally ranged from 0.04 μM to 8.71 μM.

ANTI-ALLERGIC ACTIVITY IN VIVO

Compounds of the invention have been tested for effects on an IgE-mediated allergic pulmonary inflammation induced by inhalation of antigen by sensitized guinea pigs. Guinea pigs were initially sensitized to ovalbumin under mild cyclophosphamide-induced immunosuppression, by intraperitoneal injection of antigen in combinations with aluminum hydroxide and pertussis vaccine. Booster doses of antigen were given two and four weeks later. At six weeks, animals were challenged with aerosolized ovalbumin while under cover of an intraperitoneally administered antihistamine agent (mepyramine). After a further 48 h, bronchial alveolar lavages (BAL) were performed and the numbers of eosinophils and other leukocytes in the BAL fluids were counted. The lungs were also removed for histological examination for inflammatory damage. Administration of compounds of the Examples (0.001–10 mg/kg i.p. or p.o.), up to three times during the 48 h following antigen challenge, lead to a significant reduction in the eosinophilia and the accumulation of other inflammatory leukocytes. There was also less inflammatory damage in the lungs of animals treated with compounds of the Examples.

SPA BASED PDE ACTIVITY ASSAY PROTOCOL

Compounds which inhibit the hydrolysis of cAMP to AMP by the type-IV cAMP-specific phosphodiesterases were screened in a 96-well plate format as follows:

In a 96 well-plate at 30° C. was added the test compound (dissolved in 2 μL DMSO), 188 mL of substrate buffer containing [2,8-³H] adenosine 3',5'-cyclic phosphate (cAMP, 100 nM to 50 μM), 10 mM MgCl2, 1 mM EDTA, 50 mM Tris, pH 7.5. The reaction was initiated by the addition of 10 mL of human recombinant PDE4 (the amount was controlled so that ~10% product was formed in 10 min.). The reaction was stopped after 10 min. by the addition of 1 mg of PDE-SPA beads (Amersham Pharmacia Biotech, Inc., Piscataway, N.J.). The product AMP generated was quantified on a Wallac Microbeta® 96-well plate counter (EG&G Wallac Co., Gaithersburg, Md.). The signal in the absence of enzyme was defined as the background. 100% activity was defined as the signal detected in the presence of enzyme and DMSO with the background subtracted. Percentage of inhibition was calculated accordingly. $IC_{50}$ value was approximated with a non-linear regression fit using the standard 4-parameter/multiple binding sites equation from a ten point titration.

The $IC_{50}$ values of Examples 1–42 were determined with 100 nM cAMP using the purified GST fusion protein of the human recombinant phosphodiesterase IVa (met-248) produced from a baculovirus/Sf-9 expression system. The $IC_{50}$ values of Examples 1–42 generally ranged from 0.14 nM to 10.24 nM, although one example had an $IC_{50}$ value of 109 nM.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18–25° C. Evaporation of solvent was carried out using a rotary evaporator under reduced pressure (600–4000 pascals: 4.5–30 mm. Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. Yields are given for illustration only. When given, NMR data is in the form of delta (δ) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations have also been used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

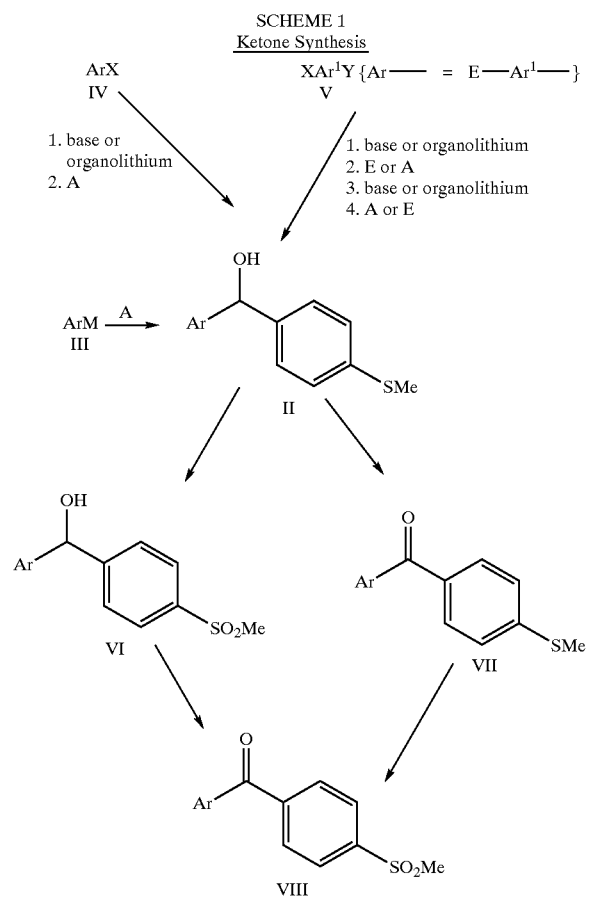

SCHEME 1
Ketone Synthesis

Wherein X=halogen, H
Y=halogen, H
A=4-(methylthio)benzaldehyde
E=electrophile
Ar=aryl or heteroaryl Referring to Scheme 1 above, and Scheme 1 Table below, the alcohol intermediate II may be prepared by the reaction of an aryl or heteroaryl metallic species III such as an organomagnesium halide with 4-(methylthio)benzaldehyde (A) in an organic solvent such as THF. The alcohol intermediate II may also be prepared by treatment an aryl or heteroaryl hydride or bromide IV with a base or an organometallic such as n-butyllithium in an organic solvent such as THF, followed by 4-(methylthio)benzaldehyde. Alternatively the alcohol intermediate II may also be prepared by the following chemical transformations: 1) Treatment of an aryl or heteroaryl dihydride, halide-hydride or dihalide V with a base or an organometallic such as n-butyllithium in an organic solvent such as THF, followed by an electrophile such as acetone or 4-(methylthio)benzaldehyde; 2) Subsequent treatment with a base or an organometallic such as n-butyllithium in an organic solvent such as THF, followed by an electrophile such as acetone or 4-(methylthio) benzaldehyde, where the first or the second transformation must use 4-(methylthio)benzaldehyde as the electrophile. The sulfone-alcohol VI may be prepared by the oxidation of the sulfide-alcohol II with an oxidizing agent such as oxone in a solvent such as a mixture of $THF/MeOH/H_2O$. The ketones VII and VIII may be prepared by the oxidation of the alcohols II and VI, respectively, with an oxidizing agent such as $MnO_2$ in a solvent such as $CH_2Cl_2$. The sulfone-ketone VIII may also be prepared by the oxidation of the sulfide-ketone VII with an oxidizing agent such as oxone in a solvent such as a mixture of THF/MeOH/H$_2$O.

concentrated. The residue was then treated with MnO$_2$ (28.6 g, 330 mmol) in CH$_2$Cl$_2$ (150 mL) and the reaction was stirred at r.t. overnight. The mixture was filtered through a

SCHEME 1 TABLE

Ketones

VII (n = 0)
VIII (n = 2)

| Ar | n | Ketone | Ar | n | Ketone |
|---|---|---|---|---|---|
| 4-fluorobenzyl | 2 | K1 | 6-methylpyridin-3-ylmethyl | 2 | K7 |
| 1-methyl-1H-imidazol-2-ylmethyl | 0 | K2 | 5-methylpyridin-2-ylmethyl | 2 | K8 |
| benzyl | 2 | K3 | 4-(methylsulfonyl)benzyl | 2 | K9 |
| thiazol-2-ylmethyl | 0<br>2 | K4<br>K5 | pyridin-2-ylmethyl | 2 | K10 |
| 5-(2-hydroxypropan-2-yl)thiazol-2-ylmethyl | 2 | K6 | 5-(2-hydroxypropan-2-yl)pyridin-2-ylmethyl | 2 | K11 |

Ketone K1

(4-Fluorophenyl)[4-(methylsulfonyl)]phenyl Ketone Ketone K1 was Prepared by the Following Procedure.

Step 1: (4-Fluorophenyl)[4-methylthio)phenyl]ketone

To a −78° C. solution of 4-(methylthio)benzaldehyde (2.5 g, 16.4 mmol) in THF (100 mL) was added 4-fluorophenylmagnesium bromide (1.0M in THF, 19.7 mL, 19.7 mmol) dropwise. The resulting solution was stirred at −78° C. for 3 h., and quenched with a saturated aqueous solution of NH$_4$Cl. The mixture was then diluted with EtOAc and HCl 10%, extracted and washed (NaHCO$_3$ (sat.), brine). The organic phase was dried over MgSO$_4$ and concentrated.

plug of silica (EtOAc) to yield 2.6 g of the (4-Fluorophenyl) [4-methylthio)phenyl]ketone compound Step 2: (4-Fluorophenyl)[4-(methylsulfonyl)phenyl] ketone To a solution of the sulfide—in other words, the (4-Fluorophenyl)[4-methylthio)phenyl]ketone—from the present step 1 (2.0 g, 8.1 mmol) in THF/MeOH/H$_2$O (80/ 40/40 ml) was added oxone (7.5 g, 12.2 mmol). The mixture was stirred at r.t. for 4 h, quenched with NaHCO$_3$ (sat.), and diluted with EtOAc. The organic phase was washed with NaHCO$_3$ (sat.), brine, dried over Na$_2$SO$_4$, filtered and concentrated. Crystallization (CH$_2$Cl$_2$/Hexanes) yielded (4-Fluorophenyl)[4-(methylsulfonyl)phenyl]ketone, the K1 ketone compound, as a white solid.

Ketone K2

(1-Methyl-1H-imidazol-2-yl)[4-methylthio)phenyl] ketone

Ketone K2 was Prepared by the Following Procedure.

Step 1: (1-Methyl-1H-imidazol-2-yl)[4-(methylthio)phenyl]methanol

To a solution of N-methylimidazole (10.0 g, 122 mmol) in 500 mL THF at −78° C. was added n-butyllithium (2.5 M in hexanes, 48.7 mL, 118 mmol) dropwise and the resulting solution was stirred at −78° C. for 30 min. 4-(Methylthio)benzaldehyde (14.73 mL, 110 mmol) was then added at −78° C. and the mixture was stirred until completion by TLC, and quenched with NH$_4$Cl (sat). The mixture was then diluted with EtOAc, extracted and washed (NaHCO$_3$ (sat.), brine). The organic phase was dried over MgSO$_4$, filtered and concentrated. Crystallization (EtOAc/Hexanes) yielded (1-Methyl-1H-imidazol-2-yl)[4-(methylthio)phenyl]methanol.

Step 2: (1-Methyl-1H-imidazol-2-yl)[4-(methylthio)phenyl]ketone

To a solution of the alcohol from the present step 1 (25.7 g, 11 mmol) in EtOAc (250 mL) and CH$_2$Cl$_2$ (250 mL) was added MnO$_2$ (140 g, 1.66 mol) and the reaction was stirred at r.t. overnight. The mixture was filtered through a plug of silica (EtOAc) to yield ketone K2.

Ketone K3

(4-Methylsulfonyl)(phenyl)ketone

Ketone K3 was Prepared by the Following Procedure.

Step 1: (4-Methylthio)(phenyl)methanol

To a solution of 4-(methylthio)benzaldehyde (1.0 g, 6.5 mmol) in THF (20 mL) at 0° C. was added phenylmagnesium chloride (2M, THF, 3.5 mL, 7.0 mmol). After 0.5 h at r.t., the mixture was neutralised with saturated NH$_4$Cl solution, diluted with water and extracted with Et$_2$O. The organic extracts were washed (H$_2$O), (brine), dried (MgSO$_4$), filtered and concentrated. Purification by stirring vigorously in hexane/Et$_2$O and filtration yielded (4-Methylthio)(phenyl)methanol as a white solid.

Step 2: (4-Methylthio)(phenyl)ketone (4-Methylthio)(phenyl)ketone was obtained by treating the (4-Methylthio)(phenyl)methanol from the present step 1 with MnO$_2$ as in step 2 of the procedure for K4 below.

Step 3: (4-Methylsulfonyl)(phenyl)ketone

To a solution of (4-Methylthio)(phenyl)ketone from the present step 2 (0.98 g, 4.3 mmol) in CHCl$_3$ (10 mL) at 0° C. was added mCPBA (m-chloroperbenzoic acid) (1.7 g, 10 mmol). After 0.5 h at r.t., Ca(OH)$_2$ (1.7 g, 23 mmol) was added to the mixture which was stirred for 1 h. Filtration on Celite® and concentration yielded ketone K3 as a white solid.

Ketone K4

(1,3-Thiazol-2-yl)[4-(methylthio)phenyl]ketone

Ketone K4 was Prepared by the Following Procedure.

Step 1: (1,3-Thiazol-2-yl) [4-(methylthio)phenyl]methanol

To a −78° C. solution of thiazole (5.0 g, 58.7 mmol) in THF (250 mL) was added n-butyllithium (2.5M in hexanes, 23.5 mL, 58.7 mmol) dropwise and the resulting solution was stirred at −78° C. for 10 min. 4-(Methylthio)benzaldehyde (7.1 mL, 53.4 mmol) was then added at −78° C. The resulting mixture was stirred until completion, and quenched with a saturated aqueous solution of NH$_4$Cl. The mixture was then diluted with EtOAc and HCl 10%, extracted and washed (NaHCO$_3$ (sat.), brine). The organic phase was dried over MgSO$_4$ and concentrated. The residue was then purified by flash chromatography (80% CH$_2$Cl$_2$/20% EtOAc) to yield (1,3-Thiazol-2-yl)[4-(methylthio)phenyl]methanol.

Step 2: (1,3-Thiazol-2-yl)[4-(methylthio)phenyl]ketone

To a solution of the (1,3-Thiazol-2-yl)[4-(methylthio)phenyl]methanol from the present step 1 (10.0 g, 42.1 mmol) in EtOAc (250 mL) was added MnO$_2$ (70 g, 843 mmol) and the reaction was stirred at 25° C. overnight. The mixture was filtered through a plug of silica (EtOAc) to form the K4 ketone compound.

Ketone K5

(1,3-Thiazol-2-yl)[4-(methylsulfonyl)phenyl]ketone

Ketone K5 was prepared by the following procedure. To a solution of K4 (1,3-Thiazol-2-yl)[4-(methylthio)phenyl] ketone (8.2 g, 34.7 mmol) in THF/MeOH/H$_2$O (350/175/175 ml) was added oxone (42.6 g, 69.4 mmol). The reaction was stirred at 25° C. for 3 h and quenched with a saturated aqueous solution of NaHCO$_3$. The resulting mixture was then diluted with EtOAc, extracted and washed (NaHCO$_3$ (sat.), brine). The organic phase was dried over MgSO$_4$ and concentrated. The residue was then purified by crystallization (EtOAc/Hexanes) to yield of (1,3-Thiazol-2-yl)[4-(methylsulfonyl)phenyl]ketone.

Ketone K6

[5-(1-Hydroxy-1-Methylethyl)-1,3-thiazol-2-yl][4-(methylsulfonyl)phenyl]ketone

Ketone K6 was Prepared by the Following Procedure.

Step 1: [5-(1-Hydroxy-1-Methylethyl)-1,3-thiazol-2-yl][4-methylthio)phenyl]ketone To a −78° C. solution of thiazole (1.0 g, 12.0 mmol) in THF (100 ml) was added n-butyllithium (2.3M in hexanes, 5.3 mL, 12.3 mmol) dropwise and the resulting solution was stirred at −78° C. for 10 min. 4-(Methylthio)benzaldehyde (7.1 mL, 53.4 mmol) was then added at −78° C. The resulting mixture was stirred at r.t. 10 min. and cooled at −78° C. Then n-butyllithium (2.3M in hexanes, 5.3 mL, 12.3 mmol) was added dropwise and the resulting solution was stirred at 25° C. for 10 min and quenched with acetone (3.0 mL). The mixture was then diluted with EtOAc and HCl 10%, extracted and washed (NaHCO$_3$ (sat.), brine). The organic phase was dried over MgSO$_4$ and concentrated. The residue was then treated with MnO$_2$ (20.4 g, 235 mmol) in CH$_2$Cl$_2$ (250 mL) and the reaction was stirred at r.t. overnight. The resulting mixture was then filtered through a plug of silica (EtOAc). Flash chromatography (90%CH$_2$Cl$_2$/10%EtOAc) yielded [5-(1-Hydroxy-1-Methylethyl)-1,3-thiazol-2-yl][4-(methylthio)phenyl)ketone.

Step 2: [5-(1-Hydroxy-1-Methylethyl)-1,3-thiazol-2-yl][4-(methylsulfonyl)phenyl]ketone To a solution of the sulfide—that is, [5-(1-Hydroxy-1-Methylethyl)-1,3-thiazol-2-yl][4-(methylthio)phenyl] ketone—from present step 1 (1.7 g, 5.8 mmol) in THF/MeOH/H$_2$O (100/50/50 ml) was added oxone (7.1 g, 11.5 mmol). The reaction was stirred at 25° C. for 3 h and quenched with a saturated aqueous solution of NaHCO$_3$. The mixture was then diluted with EtOAc, extracted and washed (NaHCO$_3$ (sat.), brine). The organic phase was dried over MgSO$_4$ and concentrated. The residue was then purified by crystallization (EtOAc/Hexanes) to yield ketone K6.

Ketone K7

(6-Methyl-3-pyridinyl)[4-(methylsulfonyl)phenyl]ketone

Ketone K7 was Prepared by the Following Procedure.

Step 1: (6-Methyl-3-pyridinyl)[4-(methylthio)phenyl]methanol

To solution of 3-bromo-6-methylpyridine (760 mg, 1 eq) in THF (20 mL) at −78° C., was added slowly n-butyllithium in hexane (1.1 eq). The solution was then stirred 30 min. 4-(thiomethyl)benzaldehyde (738 mg, 1.1 eq) was then slowly added. The solution was warmed to rt. NH$_4$Cl (sat.) was added, then water and EtOAc. The organic phase was separated, dried over MgSO$_4$, and concentrated. The (6-Methyl-3-pyridinyl)[4-(methylthio)phenyl]methanol was obtained by precipitation with ether/hexane and was used without further purification for the next step.

Step 2: (6-Methyl-3-pyridinyl)[4-(methylsulfonyl)phenyl]methanol

Following the procedure of step 2 of ketone K1 above but substituting the sulfide (6-Methyl-3-pyridinyl)[4-(methylthio)phenyl]methanol from the present step 1 for (4-fluorophenyl)(4-(methylthio)phenyl)ketone as the starting material, (6-Methyl-3-pyridinyl)[4-(methylsulfonyl)phenyl]methanol was obtained.

Step 3: (6-Methyl-3-pyridinyl)[4-(methylsulfonyl)phenyl]ketone

Following the procedure of step 2 of ketone K2 above but substituting the (6-Methyl-3-pyridinyl)[4-(methylsulfonyl)phenyl]methanol from the present step 2 for (1-methyl-1H-imidazol-2-yl)[4-(methylthio)phenyl]methanol as the starting material, ketone K7 was obtained.

Ketone K8

(5-Methyl-2-pyridinyl)[4-(methylsulfonyl)phenyl]ketone

Ketone K8 was prepared by following the procedure described for ketone K7 but substituting 2-bromo-5-methylpyridine for 3-bromo-6-methylpyridine.

Ketone K9 bis-[(4-Methylsulfonyl)phenyl]ketone

Ketone K9 was prepared by following the procedure described for ketone K7 but substituting 4-bromothioanisole for 3-bromo-6-methylpyridine and using twice the amount of Oxone in the sulfide-oxidation step.

Ketone K10

(2-Pyridinyl)[4-(methylsulfonyl)phenyl]ketone

Ketone K10 was prepared by following the procedure described for ketone K7 but substituting 2-bromopyridine for 3-bromo-6-methylpyridine.

Ketone K11

[5-(1-Hydroxy-1-methylethyl)-2-pyridinyl][4-(methylsulfonyl)phenyl]ketone

Ketone K11 was Prepared by the Following Procedure.

Step 1: [5-(1-Hydroxy-1-methylethyl)-2-pyridinyl][4-(methylthio)phenyl]methanol

To a suspension of 2,5-dibromopyridine (5.12 g, 1 eq) in ether at −78° C., was added n-butyllithium in hexane (1.05 eq) slowly. The resulting yellow-orange precipitate was stirred 30 min. Then acetone (1.54 mL, 1.05 eq) was added. The solution was kept at −78° C. for another 30 min. n-Butyllithium in hexane (1.1 eq) was slowly syringed to the resulting orange suspension. The suspension was then stirred 1 h at −78° C. Following this, 4-(methylthio)benzaldehyde (2.85 ml, 1.1 eq.) was added. The resulting suspension was warmed to −35° C. and quenched with a solution of NH$_4$Cl (sat.). Water and EtOAc were added and the organic layer dried over MgSO$_4$, evaporated and purified by flash chromatography (EtOAc) to give [5-(1-Hydroxy-1-methylethyl)-2-pyridinyl][4-(methylthio)phenyl]methanol.

Step 2: [5-(1-Hydroxy-1-methylethyl)-2-pyridinyl][4-(methylsulfonyl)phenyl]methanol Following the procedure described above for step 2 of ketone K1 but substituting the sulfide—that is, [5-(1-Hydroxy-1-methylethyl)-2-pyridinyl][4-(methylthio)phenyl]methanol—from the present step 1 for (4-fluorophenyl)[4-(methylthio)phenyl]ketone as the starting material, [5-(1-Hydroxy-1-methylethyl)-2-pyridinyl][4-(methylsulfonyl)phenyl]methanol was obtained.

Step 3: [5-(1-Hydroxy-1-methylethyl)-2-pyridinyl][4-(methylsulfonyl)phenyl]ketone Following the procedure described above for step 2 for ketone K2 but substituting the [5-(1-Hydroxy-1-methylethyl)-2-pyridinyl][4-(methylsulfonyl)phenyl]methanol from the present step 2 for (1-methyl-1H-imidazol-2-yl)[4-(methylthio)phenyl]methanol as the starting material, ketone K11 was obtained.

The boronate compounds utilized to prepare the compounds of this invention can be made according to Scheme 2 shown below:

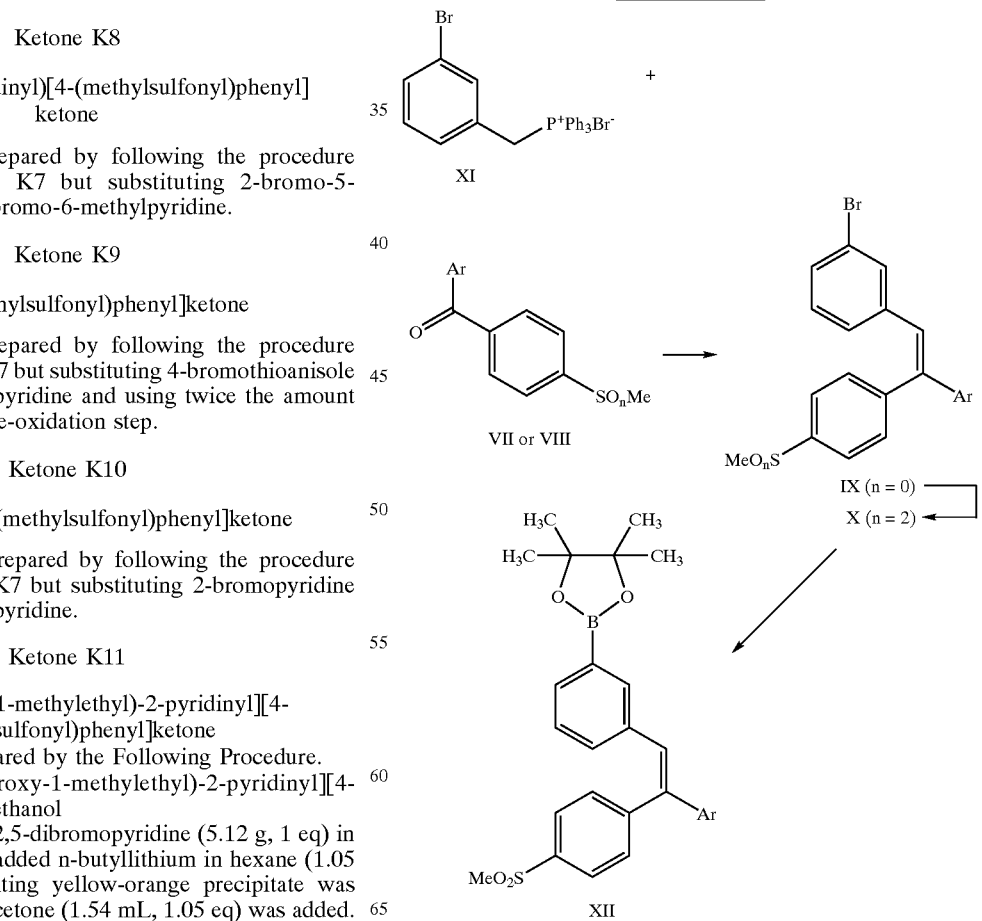

SCHEME 2
Boronate Synthesis

| Ketone (VII or VIII) | Ar | n | Boronate (XII) |
|---|---|---|---|
| K2 | 2-(1-methyl-1H-imidazol-2-yl)methylene (H₂C–imidazole with N-CH₃) | 0 | B1 |
| K4 | 2-(1,3-thiazol-2-yl)methylene (H₂C–thiazole) | 0 | B2 |
| K8 | (5-methylpyridin-2-yl)methylene (H₂C–pyridine–CH₃) | 2 | B3 |
| K11 | [5-(2-hydroxypropan-2-yl)pyridin-2-yl]methylene (H₂C–pyridine–C(CH₃)(CH₃)OH) | 2 | B4 |

The aryl bromides IX and X may be prepared by treatment of the benzyl phosphonium bromide XI with a base such as t-BuOK or LiHMDS in an organic solvent such as THF, followed by the addition of the ketone VII or VIII to the reaction mixture. The sulfide in IX may be converted to the sulfone X by treatment with oxone in a solvent such as a mixture of THF/MeOH/H₂O. The boronate ester XII can be prepared by heating the aryl bromide X with pinacol diborane in the presence of a base such as KOAc and a catalyst such as PdCl₂(dppf) in a solvent such as DMF.

Boronate B1

Pinacol 3-{(E)-2-(1-methyl-1H-imidazol-2-yl)-2-[4-(methylsulfonyl)phenyl]ethenyl}phenylboronate
Boronate B1 was Prepared by the Following Procedure.
Step 1: (E/Z)-2-(3-Bromophenyl)-1-(1-methyl-1H-imidazol-2-yl)-1-[4-(methylthio)phenyl]ethene To a solution of (3-bromobenzyl)(triphenyl)phosphonium bromide (10.2 g, 19.9 mmol) in THF (200 mL) and CH₃CN (50 mL) at 25° C. was added t-BuOK (1.0M in THF, 19.9 mL, 19.9 mmol) dropwise and the resulting red solution was stirred at r.t. for 20 min. To this resulting ylide was then added at 25° C. the ketone K2 (4.4 g, 18.9 mmol). The resulting mixture was stirred at 60° C. for 2 days and quenched with NH₄Cl (sat). The mixture was then diluted with EtOAc. The organic phase was washed with NaHCO₃ (sat.), brine, dried over MgSO₄, filtered and concentrated, and used directly in the next present step 2.

Step 2: (E)-2-(3-Bromophenyl)-1-(1-methyl-1H-imidazol-2-yl)-1-[4-(methylsulfonyl)phenyl]ethene To a solution of the crude sulfide—that is, (E/Z)-2-(3-Bromophenyl)-1-(1-methyl-1H-imidazol-2-yl)-1-[4-(methylthio)phenyl]ethene—from present step 1 (18.9 mmol) in THF/MeOH/H₂O (200/100/100 ml) was added oxone (23.2 g, 37.8 mmol). The mixture was stirred at r.t. for 4 h, quenched with NaHCO₃ (sat.), and diluted with EtOAc. The organic phase was washed with NaHCO₃ (sat.), brine, dried over Na₂SO₄, filtered and concentrated. Flash chromatography (95%EtOAc/5%Et₃N) yielded (E)-2-(3-Bromophenyl)-1-(1-methyl-1H-imidazol-2-yl)-1-[4-(methylsulfonyl)phenyl]ethene (single isomer) as a foam.

Step 3: Pinacol 3-{(E)-2-(1-methyl-1H-imidazol-2-yl)-2-[4-(methylsulfonyl)phenyl]ethenyl}phenylboronate A suspension of the bromide—that is, (E)-2-(3-Bromophenyl)-1-(1-methyl-1H-imidazol-2-yl)-1-[4-(methylsulfonyl)phenyl]ethene—from present step 2 (2.0 g; 4.8 mmol), pinacol diborane (1.5 g; 5.8 mmol), KOAc (1.65 g; 16.8 mmol) and PdCl₂(dppf) (0.2 g; 0.24 mmol) in 50 mL of DMF was stirred at 90° C. for 4 h. The resulting mixture was cooled to r.t., diluted with EtOAc, washed with H₂O (3×), brine, dried over Na₂SO₄, filtered and concentrated. Flash chromatography (95%EtOAc/5%Et₃N) yielded boronate B1 as a foam.

Boronate B2

Pinacol 3-{(E/Z)-2-(1,3-thiazol-2-yl)-2-[4-(methylsulfonyl)phenyl]ethenyl}phenylboronate
Boronate B2 was Prepared by the Following Procedure.
Step 1: (E/Z)-2-(3-Bromophenyl)-1-(1,3-thiazol-2-yl)-1-[4-(methylthio)phenyl]ethene To a solution of (3-bromobenzyl)(triphenyl)phosphonium bromide (44.5 g, 86.9 mmol) in THF (500 mL) and DMF (200 mL) at 0° C. was added LiHMDS (1.0M in THF, 86.9 mL, 86.9 mmol) dropwise and the resulting red solution was stirred at r.t. for 20 min. To the resulting ylide was then added at 0° C. the ketone K4 (18.6 g, 79.0 mmol). The mixture was stirred until completion by TLC, and quenched with a NH₄Cl (sat). The mixture was then diluted with EtOAc. The organic phase was washed with NaHCO₃ (sat.), brine, dried over MgSO₄, filtered and concentrated. Flash chromatography (CH₂Cl₂) yielded (E/Z)-2-(3-Bromophenyl)-1-(1,3-thiazol-2-yl)-1-[4-(methylthio)phenyl]ethene (1.5 to 1 mixture of isomers).

Step 2: (E/Z)-2-(3-Bromophenyl)-1-(1,3-thiazol-2-yl)-1-[4-(methylsulfonyl)phenyl]ethene To a solution of the sulfide—that is, (E/Z)-2-(3-Bromophenyl)-1-(1,3-thiazol-2-yl)-1-[4-(methylthio)phenyl]ethene—from present step 1 (24.8 g, 63.9 mmol) in THF/MeOH/H₂O (600/300/300 ml) was added Oxone (78.5 g, 128 mmol). The resulting reaction mixture was stirred at r.t. overnight. The resulting mixture was quenched with a NaHCO₃ (sat), and diluted with EtOAc. The organic phase was washed with NaHCO₃ (sat.), brine, dried over Na₂SO₄, filtered and concentrated to yield (E/Z)-2-(3-Bromophenyl)-1-(1,3-thiazol-2-yl)-1-[4-(methylsulfonyl)phenyl]ethene (3 to 2 mixture of isomers).

Step 3: Pinacol 3-{(E/Z)-2-(1,3-thiazol-2-yl)-2-[4-(methylsulfonyl)phenyl]ethenyl}phenylboronate A suspension of the bromide (E/Z)-2-(3-Bromophenyl)-1-(1,3-thiazol-2-yl)-1-[4-(methylsulfonyl)phenyl]ethene from present step 2 (15.0 g, 35.7 mmol), pinacol diborane (10.9 g, 42.8 mmol), KOAc (12.3 g, 125 mmol) and PdCl₂(dppf) (1.46 g, 1.78 mmol) in 350 mL of DMF was stirred at 90° C. for 4 h. The resulting mixture was cooled to r.t., diluted with EtOAc, washed with H₂O (3×), brine, dried over Na₂SO₄, filtered and concentrated. Flash chromatography (Tol/Acetone, 9/1) yielded boronate B2 (3 to 1 mixture of isomers) as a foam.

Boronate B3

Pinacol 3-{(E)-2-(5-methyl-2-pyridinyl)-2-[4-(methylsulfonyl)phenyl]ethenyl}phenylboronate
Boronate B3 was Prepared by the Following Procedure.
Step 1: (E)-2-(3-Bromophenyl)-1-(5-methyl-2-pyridinyl)-1-[4-(methylsulfonyl)phenyl]ethylene Following the procedure described for step 1 for boronate B1 but substituting the ketone K8 for ketone K2 as the starting material, (E)-2-(3-Bromophenyl)-1-(5-methyl-2-pyridinyl)-1-[4-(methylsulfonyl)phenyl]ethylene was obtained after separation of the isomers by flash chromatography.

Step 2: Pinacol 3-{(E)-2-(5-methyl-2-pyridinyl)-2-[4-(methylsulfonyl)phenyl]ethenyl}phenylboronate Following the procedure described for step 3 for boronate B1 but substituting the bromide (E)-2-(3-Bromophenyl)-1-(5-methyl-2-pyridinyl)-1-[4-(methylsulfonyl)phenyl] ethylene from present step 1 for (E)-2-(3-Bromophenyl)-1-(1-methyl-1H-imidazol-2-yl)-1-[4-(methylsulfonyl)phenyl] ethene as the starting material, boronate B3 was obtained.

Boronate B4

Pinacol 3-{(E)-2-(5-(1-hydroxy-1-methylethyl)-2-pyridinyl)-2-[4-(methylsulfonyl)phenyl] ethenyl}phenylboronate Boronate B4 was Prepared by the Following Procedure.

Step 1: (E)-2-(3-Bromophenyl)-1-[5-(1-hydroxy-1-methylethyl)-2-pyridinyl]-1-[4-(methylsulfonyl)phenyl] ethene Following the procedure described for step 1 for boronate B1 but substituting the ketone K11 for ketone K2 as the starting material, (E)-2-(3-Bromophenyl)-1-[5-(1-hydroxy-1-methylethyl)-2-pyridinyl]-1-[4-(methylsulfonyl)phenyl] ethene was obtained after separation of the isomers by flash chromatography.

Step 2: Pinacol 3-{(E)-2-(5-(1-hydroxy-1-methylethyl)-2-pyridinyl)-2-[4-(methylsulfonyl)phenyl]ethenyl}phenylboronate Following the procedure described for step 3 for boronate B1 but substituting the bromide (E)-2-(3-Bromophenyl)-1-[5-(1-hydroxy-1-methylethyl)-2-pyridinyl]-1-[4-(methylsulfonyl)phenyl]ethene from present step 1 for (E)-2-(3-Bromophenyl)-1-(1-methyl-1H-imidazol-2-yl)-1-[4-(methylsulfonyl)phenyl]ethene as the starting material, boronate B4 was obtained.

The aryl bromide compounds utilized to prepare the compounds of this invention can be made according to Schemes 3 and 4 shown below:

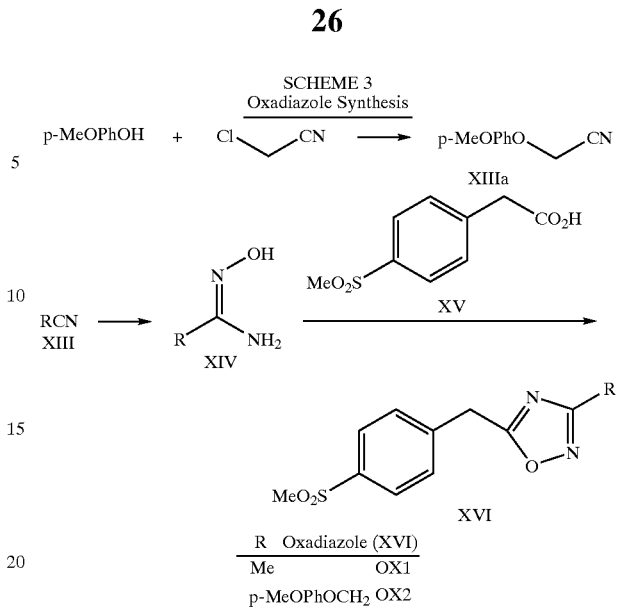

SCHEME 3
Oxadiazole Synthesis

| R | Oxadiazole (XVI) |
|---|---|
| Me | OX1 |
| p-MeOPhOCH$_2$ | OX2 |

Referring to Scheme 3 above, the nitrile intermediate XIIIa may be prepared by the alkylation of 4-methoxyphenol with chloroacetonitrile in the presence of a base such as potassium carbonate in a solvent such as acetone. The amide-oxime XIV may be prepared by treatment of the nitrile XIII with hydroxyl amine in a solvent such as methanol in the presence of a base such as sodium acetate. Formation of the oxadizole XVI may be achieved by activation of the arylacetic acid XV with carbonyldiimidazole in a solvent such as DMF followed by the addition of the amide-oxime XIV and subsequent heating of the reaction mixture.

SCHEME 4
Aryl Bromide Synthesis

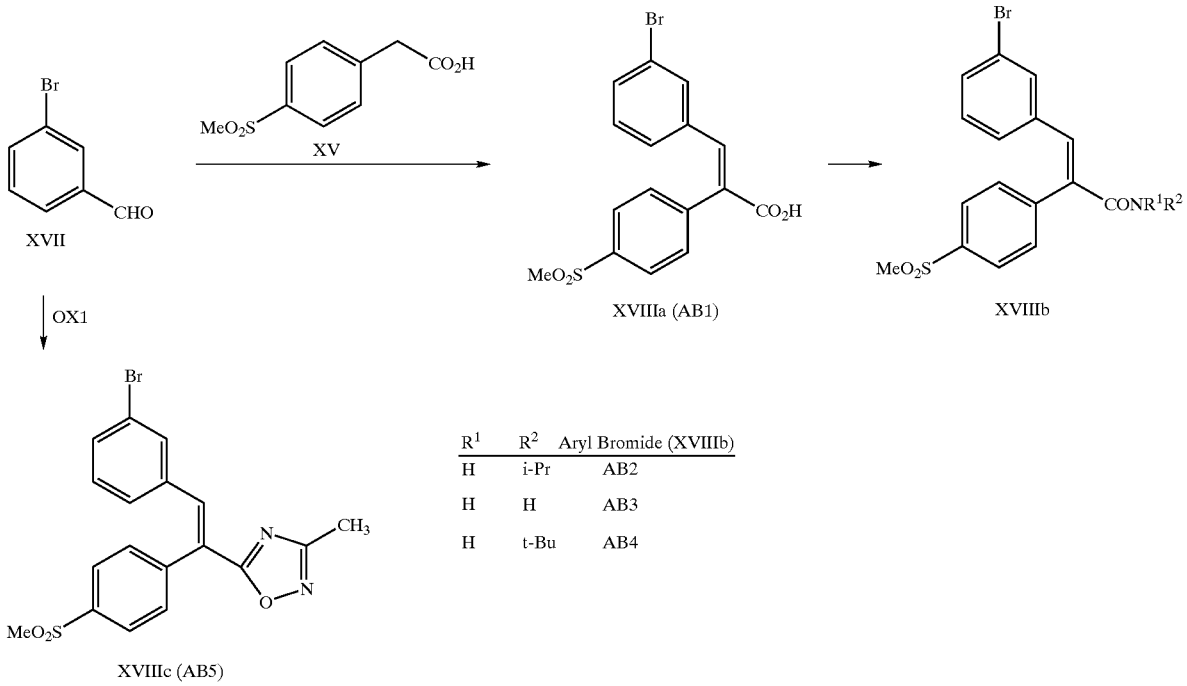

| R$^1$ | R$^2$ | Aryl Bromide (XVIIIb) |
|---|---|---|
| H | i-Pr | AB2 |
| H | H | AB3 |
| H | t-Bu | AB4 |

Referring to Scheme 4 above, condensation of the aldehyde XVII by heating with the arylacetic acid XV in the presence of a base such as piperidine in a solvent such as toluene produces the unsaturated acid XVIIIa. Formation of the acid chloride of XVIIIa in situ by treatment with thionyl chloride and a base such as triethylamine in a solvent such as toluene, is followed by the addition of an amine to the reaction mixture to yield the amide XVIIIb. The oxadiazole-ethene XVIIIc may be formed by heating OX1 with XVII in the presence of a base such as piperidine in a solvent such as toluene.

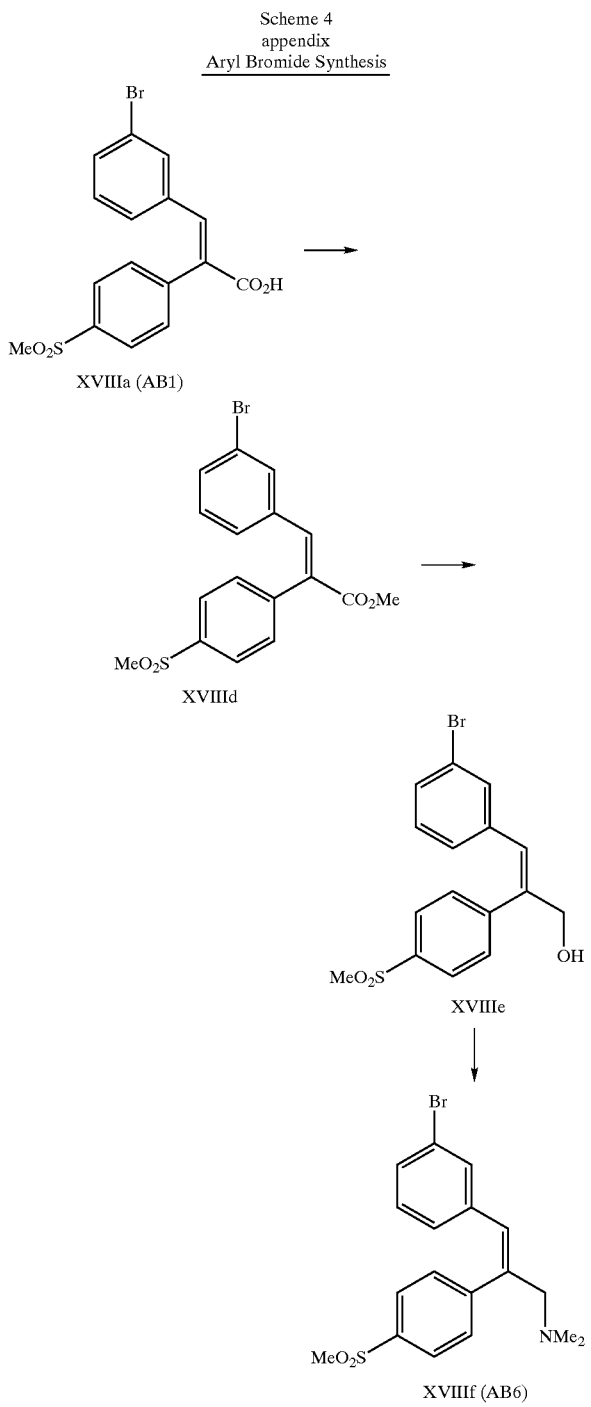

Scheme 4 appendix
Aryl Bromide Synthesis

Referring to Scheme 4 appendix above, treatment of the acid XVIIIa with diazomethane in a solvent such as THF produces the methyl ester XVIIId. Reduction of the ester XVIIId using DIBAL-H in a solvent such as THF gives the allylic alcohol XVIIIe. Conversion of the alcohol group in XVIIIe to a leaving group such as a mesylate using reagents such as methanesulfonyl chloride and triethylamine in a solvent such as THF, followed by displacement with a nucleophile such as dimethylamine in a solvent such as DMF produces the compound XVIIIf.

Aryl Bromide AB1

(E)-3-(3-Bromophenyl)-2-[4-(methylsulfonyl)phenyl]-2-propenoic Acid

Aryl Bromide AB1 was prepared by the following procedure. To a solution of 3-bromobenzaldehyde (12.9 g, 70 mmol) in toluene (100 mL) was added 4-(methylsulfonyl)phenylacetic acid (15 g, 70 mmol) and piperidine (2 mL). After overnight refluxing, the mixture was cooled down to r.t. To the slurry thus formed, toluene was added (10 mL). Filtration gave (E)-3-(3-Bromophenyl)-2-[4-(methylsulfonyl)phenyl]-2-propenoic acid as a white solid.

Aryl Bromide AB2

(E)-N-Isopropyl-3-(3-bromophenyl)-2-[4-(methylsulfonyl)phenyl]-2-propenamide

Aryl Bromide AB2 was Prepared by the Following Procedure. To a solution of AB1 (24.9 g, 65 mmol) in toluene (250 mL) was added thionyl chloride (14.3 mL, 196 mmol) and triethylamine (34 mL, 245 mmol). After stirring at r.t. for 0.5 h., isopropyl amine (28 mL, 327 mmol) was added. After a further 2 h at r.t., the mixture was cooled to 0° C. and was neutralized with saturated $NH_4Cl$ solution, then extracted with EtOAc. The organic extracts were washed ($H_2O$, brine), dried ($MgSO_4$), filtered and concentrated. Purification by flash chromatography (Hex:EtOAc, 1:1 to pure EtOAc) yielded (E)-N-Isopropyl-3-(3-bromophenyl)-2-[4-(methylsulfonyl)phenyl]-2-propenamide.

Aryl Bromide AB3

(E)-3-(3-Bromophenyl)-2-[4-(methylsulfonyl)phenyl]-2-propenamide

Aryl Bromide AB3 was prepared by following the procedure described for aryl bromide AB2 but substituting ammonium hydroxide for isopropyl amine as the starting material.

Aryl Bromide AB4

(E)-N-(t-Butyl)-3-(3-Bromophenyl)-2-[4-(methylsulfonyl)phenyl]-2-propenamide

Aryl Bromide AB4 was prepared by following the procedure described for aryl bromide AB2 but substituting t-butyl amine for isopropyl amine as the starting material.

Aryl Bromide AB5

(E)-1-(3-Bromophenyl)-2-(3-methyl-1,2,4-oxadiazol-5-yl)-2-[4-(methylsulfonyl)phenyl]ethene Aryl Bromide AB5 was Prepared by the Following Procedure.

Step 1 (Scheme 3, Oxadiazole OX1): (3-Methyl-1,2,4-oxadiazol-5-yl) [4-(methylsulfonyl)phenyl]methane To a solution of 4-(methylsulfonyl)phenylacetic acid (15 g, 70 mmol) in DMF (300 mL) at r.t., was added carbonyldiumidazole (12.5 g, 77 mmol). After 0.5 h at r.t., acetamide oxime (5.7 g, 77 mmol) was added. After stirring the resulting mixture overnight at r.t., the mixture was heated to 120° C. for 6 h. After cooling to r.t., the mixture was quenched with $H_2O$, and extracted with EtOAc. The organic extracts were washed ($H_2O$, brine), dried ($MgSO_4$), filtered and concentrated. Purification by flash chromatography (Hex:EtOAc, 1:1) yielded (3-Methyl-1,2,4-oxadiazol-5-yl)[4-(methylsulfonfyl)phenyl]methane.

Step 2 (Scheme 4): (E)-1-(3-Bromophenyl)-2-(3-methyl-1,2,4-oxadiazol-5-yl)-2-[4-(methylsulfonyl)phenyl]ethene To a solution of 3-bromobenzaldehyde (2.2 g, 11.9 mmol) in toluene (30 mL) was added the product from step 1 (OX1) (3.0 g, 11.9 mmol) and piperidine (0.4 mL). After overnight refluxing, the mixture was cooled down to r.t. To the resulting slurry, MeOH (30 mL) was added. After further refluxing then cooling to 0° C., filtration gave (E)-1-(3-Bromophenyl)-2-(3-methyl-1,2,4-oxadiazol-5-yl)-2-[4-(methylsulfonyl)phenyl]ethene as a white solid.

The Bromoquinolines utilized to prepare the compounds of this invention can be made according to Scheme 5 shown below:

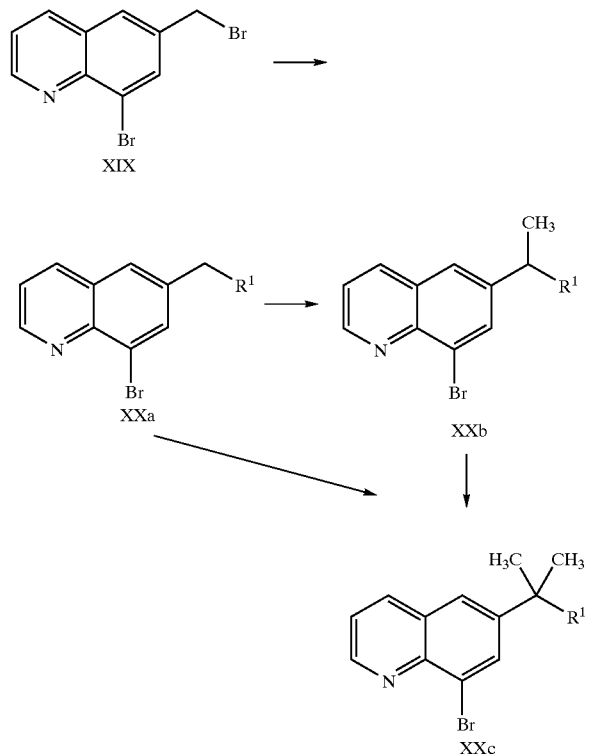

SCHEME 5
Preparation of Bromoquinolines iodide in a solvent such as THF. The compound XXc (where $R^1$=CN) may also be prepared by treatment of XXa with a base such as potassium t-butoxide (2.2 equivalents) and methyl iodide in a solvent such as THF. The compound XXc (where $R^1$=$SO_2$Me) may also be prepared by treatment of XXa with a base such as potassium t-butoxide (1.3 equivalents) and methyl iodide (1.6 equivalents) in a solvent such as THF, followed by an additional amount of methyl iodide (1.6 equivalents) and an additional amount of the same base (1.0 equivalents).

SCHEME 5 TABLE

Bromoquinolines

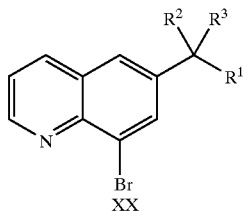

XX

| $R^1$ | $R^2$ | $R^3$ | Bromoquinoline (XX) |
|---|---|---|---|
| $SO_2$Me | H | H | Q1 |
| $SO_2$Me | Me | H | Q2 |
| $SO_2$Me | Me | Me | Q3 |
| CN | H | H | Q4 |
| CN | Me | Me | Q5 |

Bromoquinoline Q1

6-(Methylsulfonyl)methyl-8-bromoquinoline

Bromoquinoline Q1 was prepared by the following procedure. DMF (500 mL) was added to 6-bromomethyl-8-bromoquinoline (60 g, 200 mmol) (described in International Patent Publication WO 94/22852) and sodium methanesulfinate (27.6 g, 270 mmol). After stirring overnight at r.t., the mixture was quenched with $H_2O$ (2000 mL), stirred for one hour, isolated by filtration and washed with $Et_2O$ to yield 6-(methylsulfonyl)methyl-8-bromoquinoline.

Bromoquinoline Q2

6-[1-(Methylsulfonyl)ethyl]-8-bromoquinoline

Referring to Scheme 5 above and the Scheme 5 table below, treatment of the bromomethyl compound XIX with a nucleophile such as sodium methanesulfinate or potassium cyanide in a solvent such as DMF or a mixture of DMF and water can be used to produce the compounds XXa. The compound XXb may be prepared by treatment of XXa with a base such as potassium t-butoxide (1.1 equivalents) in a solvent such as THF followed by the addition of the resulting mixture into a solution of methyl iodide in a solvent such as THF. The compound XXc may be prepared by treatment of XXb with a base such as potassium t-butoxide (1.1 equivalents) in a solvent such as THF followed by the addition of the resulting mixture into a solution of methyl Bromoquinoline Q2 was prepared by the following procedure. To a solution of bromoquinoline Q1 (16.1 g, 54 mmol) in THF (500 mL) at −78° C., was added potassium t-butoxide (59 mL, 1N in THF). After 0.5 h at −78° C., the resulting mixture was stirred at 0° C. for 45 min and then transferred by canula dropwise into a solution of MeI (16.7 mL, 268.3 mmol) in THF (160 mL). After stirring overnight at r.t., the mixture was neutralised with saturated $NH_4Cl$ solution and extracted with EtOAc. The organic extracts were washed ($H_2O$), (brine), dried ($MgSO_4$), filtered and concentrated. Stirring in ether, followed by isolation by filtration gave 6-[1-(methylsulfonyl)ethyl]-8-bromoquinoline.

Bromoquinoline Q3

6-[1-Methyl-1-(methylsulfonyl)ethyl]-8-bromoquinoline

Bromoquinoline Q3 was prepared by the following procedure. To a solution of bromoquinoline Q2 (15.7 g, 50 mmol) in THF (500 mL) at −78° C., was added potassium t-butoxide (55 mL, 1N in THF). After stirring 0.5 h at −78° C., the resulting mixture was stirred at 0° C. for 45 min and then transferred dropwise into a solution of MeI (15.6 mL, 250 mmol) in THF (40 mL) at 0° C. After stirring overnight at r.t., the mixture was neutralised with saturated NH$_4$Cl solution, and extracted with EtOAc. The organic extracts were washed (H$_2$O, brine), dried (MgSO$_4$), filtered and concentrated. Stirring in ether, followed by isolation by filtration gave 6-[1-methyl-1-(methylsulfonyl)ethyl]-8-bromoquinoline.

Bromoquinoline Q4

6-Cyanomethyl-8-bromoquinoline

Bromoquinoline Q4 was prepared by the following procedure. DMF (10 mL) and H$_2$O (5 mL) were added to 6-bromomethyl-8-bromoquinoline (3 g, 10 mmol) (described in International Patent Publication WO 94/22852) and potassium cyanide (1.6 g, 25 mmol). After heating at 100° C. for 1 hour, the resulting mixture was quenched with H$_2$O (100 mL) and extracted with EtOAc. The organic extracts were washed (H$_2$O, brine), dried (MgSO$_4$), filtered and concentrated. Purification by flash chromatography (Hex:EtOAc, 3:1) yielded 6-cyanomethyl-8-bromoquinoline.

Bromoquinoline Q5

6-[1-Methyl-1-cyanoethyl]-8-bromoquinoline

Bromoquinoline Q5 was prepared by the following procedure. To a solution of bromoquinoline Q4 (3 g, 12.1 mmol) in THF (100 mL) at −78° C., was added MeI (1.7 mL, 27 mmol) followed by potassium t-butoxide (27 mL, 27 mmol). After 2 h at −78° C., the mixture was warmed to 0° C. and was neutralized with saturated NH$_4$Cl solution then extracted with EtOAc. The organic extracts were washed (H$_2$O, brine), dried (MgSO$_4$), filtered and concentrated. Purification by flash chromatography (Hex:EtOAc, 3:1) yielded 6-[1-methyl-1-cyanoethyl]-8-bromoquinoline.

The Benzyl Phosphorus Reagents utilized to prepare the compounds of this invention can be made according to Scheme 6 shown below:

SCHEME 6

Preparation of Benzyl Phosphorus Reagents

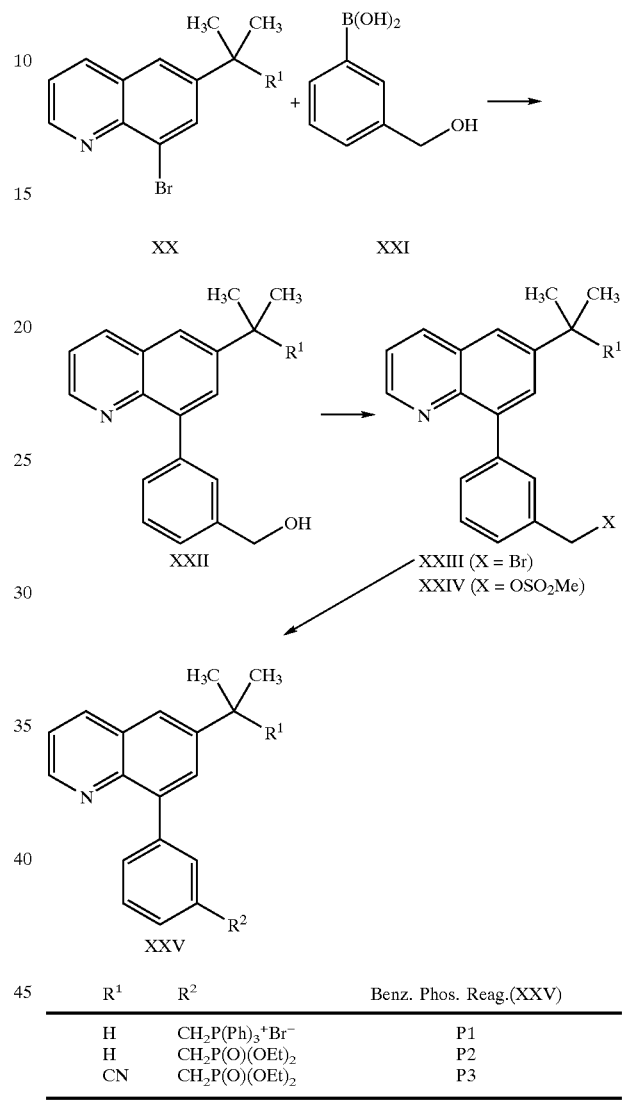

| R$^1$ | R$^2$ | Benz. Phos. Reag.(XXV) |
|---|---|---|
| H | CH$_2$P(Ph)$_3{}^+$Br$^-$ | P1 |
| H | CH$_2$P(O)(OEt)$_2$ | P2 |
| CN | CH$_2$P(O)(OEt)$_2$ | P3 |

The arylquinolines of the formula XXII may be prepared by coupling bromoquinoline XX with the boronic acid XXI by heating in the presence of a catalyst such as Pd(PPh$_3$)$_4$ and a base such as sodium carbonate (aqueous) in a solvent such as a DME. The alcohol XXII may be converted to the bromide XXIII by treatment with HBr (aq) in a solvent such as acetic acid. The alcohol XXII may be converted to the methyl sulfonate ester XXIV by methanesulfonyl chloride in the presence of a base such as triethylamine in a solvent such as dichloromethane. The benzyl phosphorous reagents XXV may be prepared either by heating XXIII in the presence of PPh$_3$ in a solvent such as acetonitrile or by treating XXIII or XXIV with diethylphosphite and a base such as potassium t-butoxide in a solvent such as THF.

Benzylphosphonium Bromide P1

[3-(6-Isopropyl-8-quinolinyl)benzyl](triphenyl) phosphonium Bromide

Benzylphosphonium Bromide P1 was prepared by the following procedure.

Step 1: 6-Isopropyl-8-[3-(hydroxymethyl)phenyl] quinoline

A mixture of 6-isopropyl-8-Bromoquinoline (11.1 g, 44.4 mmol) (described in International Patent Publication WO 94/22852), 3-(hydroxymethyl)phenylboronic acid (8.70 g, 57.2 mmol), $Na_2CO_3$ (2M, 71 mL, 142 mmol) and $Pd(PPh_3)_4$ (2.51 mg, 2.17 mmol) in 280 mL of DME was stirred at 80° C. for 5 h. The resulting mixture was cooled to r.t., diluted with EtOAc, washed with brine, dried over $Na_2SO_4$, filtered and concentrated. Flash chromatography (Hex/EtOAc, 1/1) and stirring in $CH_2Cl_2$/hexane (1/9) yielded 6-Isopropyl-8-[3-(hydroxymethyl)phenyl]quinoline as a white solid.

Step 2: 6-Isopropyl-8-[3-(bromomethyl)phenyl]quinoline

A suspension of the hydroxymethyl product compound from present step 1 (7.40 g, 26.7 mmol) in AcOH (50 mL) and HBr (50 mL, 48% aq) was stirred for 12 h at 100° C. The mixture was cooled to r.t., poured into NaOH (2N) in ice, the pH was adjusted to 8 and the mixture was diluted with ether. The organic phase was washed with brine, dried over $MgSO_4$, filtered and concentrated to yield 6-Isopropyl-8-[3-(bromomethyl)phenyl]quinoline as a yellow solid.

Step 3: [3-(6-Isopropyl-8-quinolinyl)benzyl](triphenyl) phosphonium Bromide

To a solution of the bromomethyl product compound from present step 2 (3.807 g, 11.1 mmol) in 40 mL of $CH_3CN$ was added triphenylphosphine (3.22 g, 12.3 mmol). The mixture was stirred at 60° C. for 12 h, cooled to r.t., diluted with ether, filtered, and washed with ether to yield [3-(6-Isopropyl-8-quinolinyl)benzyl](triphenyl)phosphonium Bromide.

Benzylphosphonate P2

Diethyl 3-(6-isopropyl-8-quinolinyl)benzylphosphonate

Benzylphosphonate P2 was Prepared by the Following Procedure. The bromomethyl compound from step 2 above of the synthesis of P1 (11.34 g, 1 eq) was dissolved in THF (170 mL). Diethylphosphite (3.87 mL, 1.05 eq) was added and the solution was cooled down to 0° C. Next, t-BuOK (3.87 mL, 1N in THF) was added slowly. The reaction was stirred 2 h and the quenched by addition of $NH_4Cl(sat)$, water and EtOAc. The organic phase was separated and washed with brine, dried over $MgSO_4$ and concentrated. Purification by flash chromatography on silica gel (hexane:EtOAc, 1/9) gave Diethyl 3-(6-isopropyl-8-quinolinyl)benzylphosphonate as a clear oil.

Benzylphosphonate P3

Diethyl 3-[6-(1-cyano-1-methylethyl)-8-quinolinyl]benzylphosphonate

Benzylphosphonate P3 was Prepared by the Following Procedure.

Step 1: 6-(1-Cyano-1-methylethyl)-8-[3-(hydroxymethyl)phenyl]quinoline

Following step 1 described above of the procedure for Benzylphosphonium Bromide P1, but substituting the bromoquinoline Q5 for 6-isopropyl-8-bromoquinoline as the starting material, 6-(1-Cyano-1-methylethyl)-8-[3-(hydroxymethyl)phenyl]quinoline was obtained.

Step 2: 3-[6-(1-Cyano-1-methylethyl)-8-quinolinyl]benzyl methanesulfonate

To a solution of the alcohol 6-(1-Cyano-1-methylethyl)-8-[3-(hydroxymethyl)phenyl]quinoline from present step 1 (5.15 g, 17 mmol) in $CH_2Cl_2$ (150 mL) at −78° C. was added $Et_3N$ (3.6 mL, 26 mmol) and methanesulfonyl chloride ("MsCl") (1.6 mL, 21 mmol). After 0.5 h at −78° C., the mixture was neutralized with saturated $NH_4Cl$ solution, diluted with water and extracted with ether. The organic extracts were washed ($H_2O$, brine), dried ($MgSO_4$), filtered and concentrated to yield 3-[6-(1-Cyano-1-methylethyl)-8-quinolinyl]benzyl methanesulfonate as a white foam.

Step 3: Diethyl 3-[6-(1-cyano-1-methylethyl)-8-quinolinyl]benzylphosphonate

To a solution of diethylphosphite (2.5 mL, 18 mmol) in THF (100 mL) at −78° C. was added potassium t-butoxide (1M, THF, 16 mL, 16 mmol) and the mesylate compound 3-[6-(1-Cyano-1-methylethyl)-8-quinolinyl]benzyl methanesulfonate from present step 2 (5.1 g, 13.5 mmol). After 0.5 h at −78° C. and 12 h at r.t., the resulting mixture was neutralized with saturated $NH_4Cl$ solution, diluted with water and extracted with ether. The organic extracts were washed ($H_2O$, brine), dried ($MgSO_4$), filtered and concentrated. Purification by flash chromatography (Hex:EtOAc, 1:4 to 1:10) yielded Diethyl 3-[6-(1-cyano-1-methylethyl)-8-quinolinyl]benzylphosphonate as an oil.

SCHEME 7
Benzyphosphorous Reagent-Ketone Coupling

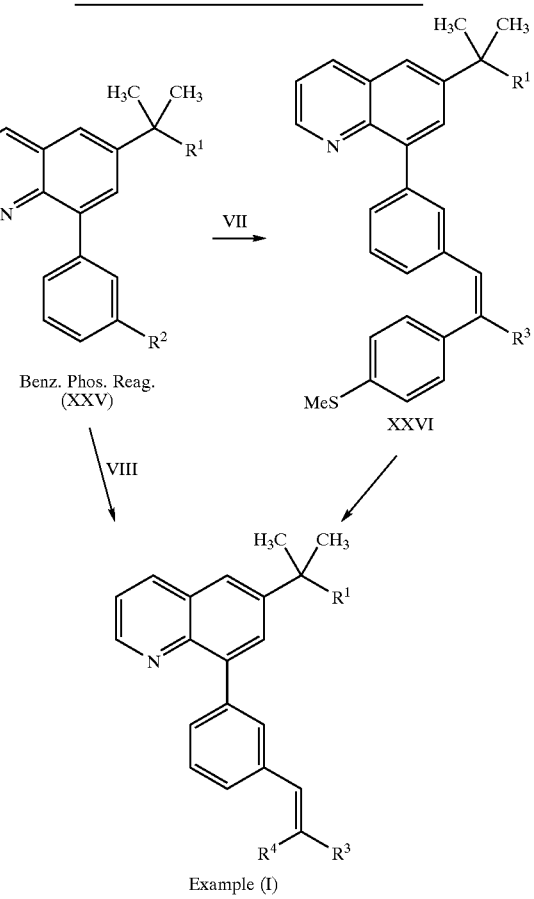

Example (I)

Compounds corresponding to the formula I may be prepared using the reaction pathways outlined in Scheme 7 above. The compound XXVI may be obtained by adding a solution of the ketone VII in a solvent such as THF to a mixture of the benzylphosphorous reagent XXV and a base such as potassium t-butoxide in a solvent such as THF. The compounds corresponding to the formula I may then be prepared by treating XXVI with oxone in a mixture of solvents such as THF/MeOH/water. Alternatively, the compounds of formula I may be prepared by reacting the ketone VIII with XXV in the presence of a base such as potassium t-butoxide in a solvent such as THF.

Referring to Scheme 7 above and Table 1 below, the coupling of the ketones with the benzyl phosphorous reagents resulted in the tabulated Examples.

TABLE 1

| Benz. Phos. Reag. | Ketone | Example |
|---|---|---|
| P2 | K3 | 1 |
| P2 | K3 | 2 |
| P1 | K5 | 3 |
| P1 | K2 | 4 |
| P2 | K1 | 5 |
| P2 | K1 | 6 |
| P2 | K6 | 7 |
| P3 | K6 | 8 |
| P3 | K2 | 9 |
| P2 | Commercial | 30 |
| P2 | K7 | 31 |
| P2 | K7 | 32 |
| P2 | K8 | 33 |
| P2 | K8 | 34 |
| P2 | K9 | 35 |
| P3 | K8 | 36 |
| P3 | K8 | 37 |
| P3 | K9 | 38 |
| P3 | K10 | 39 |

SCHEME 7
Aryl Bromide-Bromoquinoline Coupling

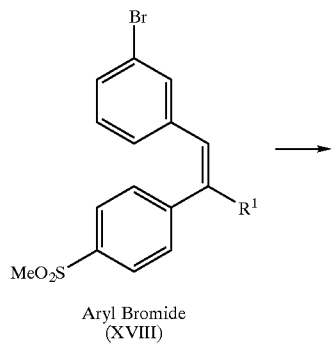

Aryl Bromide
(XVIII)

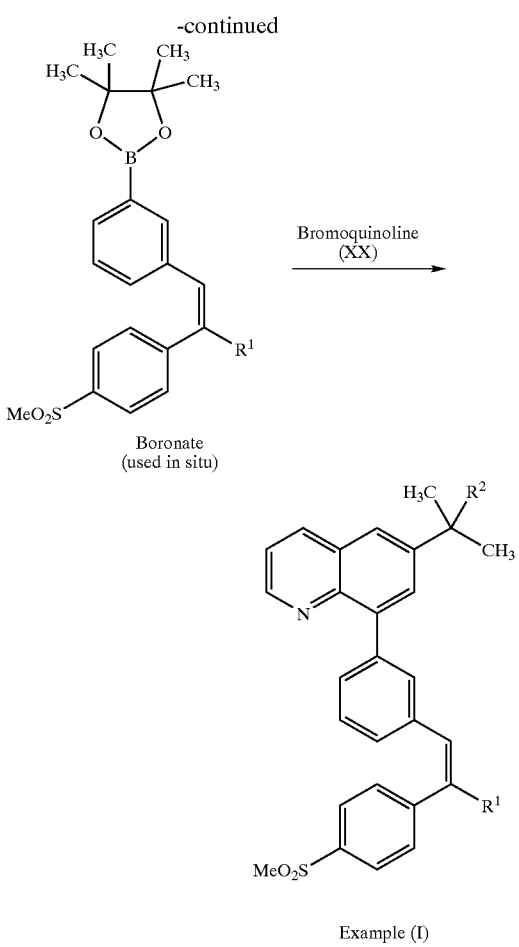

Example (I)

Referring to Scheme 8, compounds corresponding to the formula I may be prepared by in situ conversion of the aryl bromide XVIII to the corresponding boronate ester by heating with diboron pinacol ester, a catalyst such as [1,1'-bis(diphenylphosphino)-ferrocene]dichloropalladium(II) and a base such as potassium acetate in a solvent such as DMF, followed by the addition of the bromoquinoline XX, an additional amount of the same catalyst, an additional amount of a base such as sodium carbonate (aqueous) and an additional period of heating.

Referring to Scheme 8 above, Table 2 and Table 2 appendix below, the coupling of the Aryl Bromide with the Bromoquinoline resulted in the tabulated Examples.

TABLE 2

| Aryl Bromide | Bromoquinoline | Example |
|---|---|---|
| AB5 | Q3 | 14 |
| AB5 | Q3 | 15 |
| AB2 | Q5 | 16 |
| AB2 | Q5 | 17 |
| AB2 | Q3 | 20 |
| AB1 | Q5 | 21 |
| AB5 | Q5 | 22 |
| AB3 | Q5 | 23 |
| AB4 | Q5 | 24 |
| AB1 | WO 94/22852 | 25 |
| AB5 | WO 94/22852 | 26 |
| Table 2 appendix | | |
| AB6 | Q5 | 43 |

Compounds of this invention can be prepared by following Scheme 9 shown below.

SCHEME 9

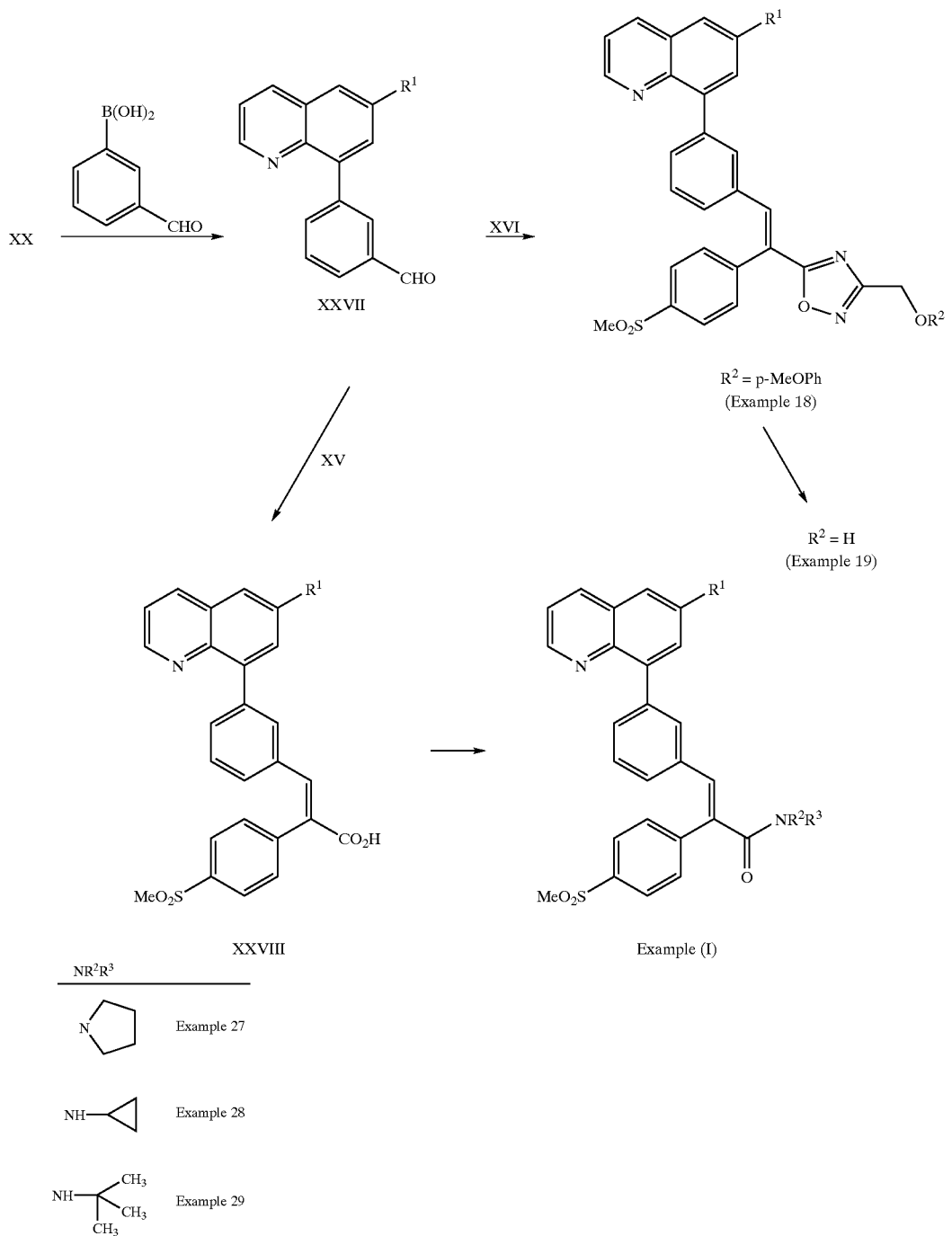

Scheme 9 outlines the preparation of compounds of formula I where the aldehyde XXVII may be prepared by heating the bromoquinoline XX, 3-formylbenzeneboronic acid, a catalyst such as Pd(PPh$_3$)$_4$ and a base such as sodium carbonate (aqueous) in a solvent such as DME. The aldehyde XXVII may be converted to Example 18 by heating with XVI in the presence of a base such as piperidine in a solvent such as toluene. Example 19 may be obtained by treatment of Example 18 with cerric ammonium nitrate ("CAN") in a mixture of solvents such as acetonitrile/water. Alternatively the aldehyde XXVII may be converted to the unsaturated acid XXVIII by heating with XV and a base such as piperidine in a solvent such as toluene. The acid XXVIII may then be converted to the amide I (Example 27, 28 and 29) by treatment with a coupling system such as EDCl, HOBt, and an amine in a solvent such as DMF.

Compounds of this invention can be prepared by coupling Bromoquinoline compounds with Boronate compounds according to Scheme 10 below.

SCHEME 10
Bromoquinoline-Boronate Coupling

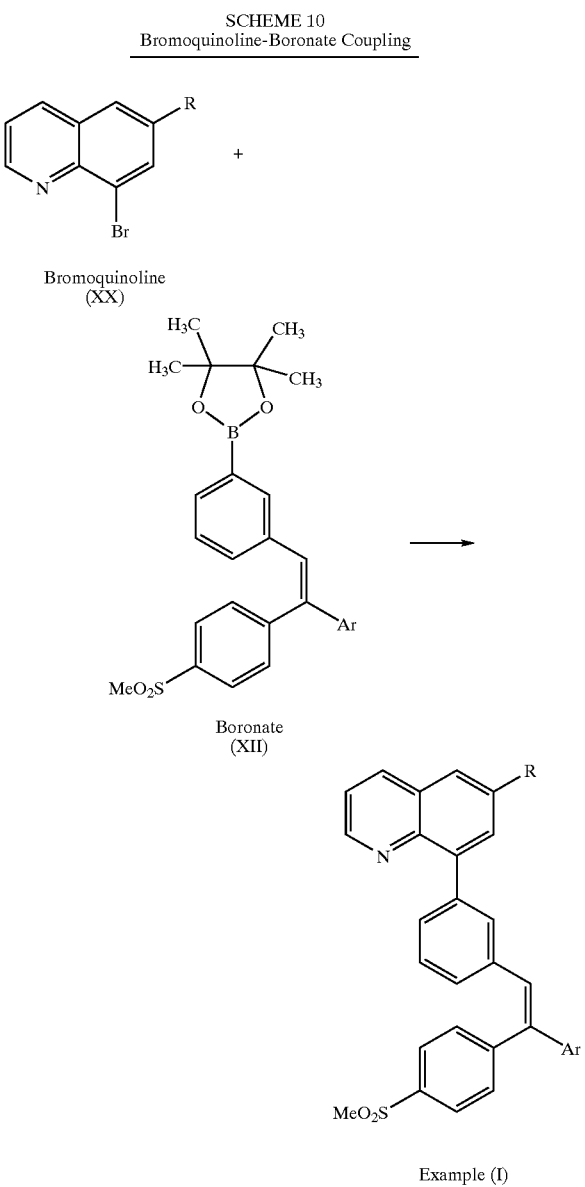

Scheme 10 describes how compounds of formula I may be obtained by coupling the bromoquinoline XX with the boronate ester XII in the presence of a catalyst such as Pd(OAc)$_2$, PPh$_3$, and a base such as sodium carbonate (aqueous) in a solvent such as n-propanol. Referring to Table 3, the coupling of the Bromoquinoline with Boronate resulted in the tabulated Examples.

TABLE 3

| Bromoquinoline | Boronate | Example |
| --- | --- | --- |
| Q2 | B2 | 10 |
| Q3 | B2 | 11 |
| Q2 | B1 | 12 |
| Q3 | B1 | 13 |
| Q3 | B3 | 40 |
| Q3 | B3 | 41 |
| Q3 | B4 | 42 |

EXAMPLES 1 and 2

6-Isopropyl-8-(3-{(Z/E)-2-[4-(methylsulfonyl) phenyl]-2-phenylethenyl}phenyl)quinoline Examples 1 and 2 were Prepared by the Following Procedure. To a mixture of benzylphosphonate P2 (330 mg, 0.83 mmol) and ketone K3 (200 mg, 0.77 mmol) in THF (6 mL) at r.t. was added potassium t-butoxide (1M, THF, 0.83 mL, 0.83 mmol). After 1 h at r.t., the mixture was diluted with water and extracted with Et$_2$O. The organic extracts were washed (H$_2$O), (brine), dried (MgSO$_4$), filtered and concentrated. Purification by flash chromatography (Hex:EtOAc, 7:3) produced Examples 1 and 2 as white foams with one product being less polar than the other product. Example 1 was the less polar Z-isomer and Example 2 was the more polar E-isomer.

Example 1: NMR $^1$H (400 MHz, Acetone-d$_6$) δ 8.79 (q, 1H), 8.28 (q, 1H), 7.94 (d, 2H), 7.73 (d, 1H), 7.6–7.1 (m, 14H), 3.14 (m, 1H), 2.97 (s, 3H), 1.34 (d, 6H).

Example 2: NMR $^1$H (400 MHz, Acetone-d$_6$) δ 8.78 (q, 1H), 8.25 (q, 1H), 7.89 (d, 2H), 7.71 (d, 1H), 7.6 (m, 3H), 7.45 (m, 3H), 7.39–7.2 (m, 8H), 3.11 (m, 4H), 1.34 (d, 6H).

EXAMPLE 3

6-Isopropyl-8-{3-[(E/Z)-2-[4-(methylsulfonyl) phenyl]-2-(1,3-thiazol-2-yl)ethenyl] phenyl}quinoline Example 3 was Prepared by the Following Procedure. To a suspension of the benzylphosphonium bromide P1 (320 mg, 0.531 mmol) in 2.5 mL THF at −78° C. was added t-BuOK (1.0M in THF, 0.55 mL, 0.55 mmol) dropwise and the resulting red solution was stirred 30 min at 0° C. To this ylide at −78° C. was then added ketone K5 (122 mg, 0.455 mmol) in 2 mL of THF dropwise. The mixture was warmed to r.t., then stirred for 1h, quenched with a NH$_4$Cl (sat.) and diluted with EtOAc. The organic phase was washed with brine, dried over Na$_2$SO$_4$, filtered and concentrated. Flash chromatography (Silica cartridge, Hex/EtOAc 10 to 100% in 20 min) yielded Example 3 (1.5 to 1 mixture of isomers).

NMR $^1$H (500 MHz in acetone-d$_6$) δ 8.79–8.78 (m, 1H), 8.26–8.23 (m, 1H), 8.01–7.92 (m, 3H), 7.84 (d, 0.4H, minor), 7.78 (d, 0.6H, major), 7.73–7.47 (m, 10H), 7.43 (dd, 1H), 7.34 (t, 0.6H, major), 7.27 (t, 0.4H, minor), 7.18 (d, 0.6H, major), 7.09 (d, 0.4H, minor), 3.12 (m, 1H), 3.11 (s, 1.8H, major), 2.99 (s, 1.2H, minor), 1.36–1.33 (m, 6H). MS (M+1) 511.

EXAMPLE 4

6-Isopropyl-8-(3-{(E)-2-(1-methyl-1H-imidazol-2-yl)-2-[4-(methylsulfonyl)phenyl]ethenyl}phenyl) quinoline Example 4 was Prepared by the Following Procedure.

Step 1: 6-isopropyl-8-(3-{(E)-2-(1-methyl-1H-imidazol-2-yl)-2-[4-(methylthio)phenyl]ethenyl}phenyl)quinoline Following the procedure for Example 3 but substituting the ketone K2 for K5 as the starting material, 6-isopropyl-8-(3-{(E)-2-(1-methyl-1H-imidazol-2-yl)-2-[4-(methylthio) phenyl]ethenyl}phenyl)quinoline was obtained.

Step 2: 6-isopropyl-8-(3-{(E)-2-(1-methyl-1H-imidazol-2-yl)-2-[4-(methylsulfonyl)phenyl]ethenyl}phenyl) quinoline.

Following the procedure used for the preparation of the boronate B1 (step 2 of Scheme 2) but substituting the sulfide obtained in the present step 1 for (E/Z)-2-(3-Bromophenyl)-

1-(1-methyl-1H-imidazol-2-yl)-1-[4-(methylthio)phenyl] ethene as the starting material, Example 4 was obtained.

NMR $^1$H (500 MHz in acetone-d$_6$) δ 8.77 (dd, 1H), 8.24 (dd, 1H), 7.88 (d, 2H), 7.71(d, 1H), 7.59 (d, 1H), 7.53 (d, 2H), 7.48 (d, 2H), 7.41 (dd, 1H) 7.28 (t, 1H), 7.23 (s, 1H), 7.15 (d, 1H), 7.07 (d, 1H), 6.95 (d, 1H), 3.51 (s, 3H), 3.10 (m, 1H), 2.99 (s, 3H), 1.32 (d, 6H). MS: (m+2): 509.4.

EXAMPLES 5 and 6

6-Isopropyl-8-(3-{(Z/E)-2-(4-fluorophenyl)-2-[4-(methylsulfonyl)phenyl]ethenyl}phenyl)quinoline Examples 5 and 6 were Prepared by the Following Procedure. Following the procedure for Example 1 but substituting the ketone K1 for K3 as the starting material, and purification by flash chromatography (50%EtOAc/50%Hexanes) yielded Examples 5 and 6.

NMR $^1$H (500 MHz in acetone-d$_6$) Example 5: Major (Z) isomer: δ 8.78 (dd, 1H), 8.25 (dd, 1H), 7.93 (d, 2H), 7.72 (d, 1H), 7.55–7.40 (m, 6H), 7.35 (m, 2H), 7.25 (t, 1H), 7.23 (s, 1H), 7.11 (t, 2H), 7.05 (d, 1H), 3.12 (m, 1H), 2.96 (s, 3H), 1.34 (d, 6H).

NMR $^1$H (500 MHz in acetone-d$_6$) Example 6: Minor (E) isomer: δ 8.78 (dd, 1H), 8.35 (dd, 1H), 7.93 (d, 2H), 7.72 (d, 1H), 7.65–7.55 (m, 3H), 7.45 (dd, 1H), 7.35–7.15 (m, 9H), 3.12 (m, 4H), 1.34 (d, 6H).

EXAMPLE 7

2-(2-{(E/Z)-2-[3-(6-Isopropyl-8-quinolinyl)phenyl]-1-[4-(methylsulfonyl)phenyl]ethenyl}-1,3-thiazol-5-yl)-2-propanol Example 7 was prepared by following the procedure for Example 1 but substituting the ketone K6 for K3 as the starting material. Purification by flash chromatography (100%EtOAc) yielded Example 7 as a mixture of isomers.

NMR $^1$H (400 MHz in acetone-d$_6$) δ 8.80 (m, 1H), 8.30 (m, 1H), 8.05 (d(major), 1.44H), 7.93 (d(minor), 0.55H), 7.85 (s(major), 0.72H), 7.77 (s,(minor), 0.28H), 7.75–7.45 (m, 7H) 7.35 (t(minor), 0.28H), 7.28 (t,(major), 0.72H), 7.21 (d(minor), 0.28H), 7.10 (d(major), 0.72H), 4.7 (m, 1H), 3.15 (m, 1H), 3.15 (s(minor), 0.84), 2.99 (s(major), 2.16H), 1.60 (m, 6H), 1.35 (m, 6H). MS (m+1): 569.6.

EXAMPLE 8

2-[8-(3-{(E/Z)-2-[5-(1-Hydroxy-1-methylethyl)-1,3-thiazol-2-yl]-2-[(methylsulfonyl)phenyl] ethenyl}phenyl)-6-quinolinyl]-2-methylpropanenitrile Example 8 was prepared by following the procedure for Example 1 but substituting the ketone K6 for K3 and the benzyl phosponate P3 for P2 as the starting materials. Purification by flash chromatography (20%CH$_2$Cl$_2$/80%EtOAc) yielded Example 8 as a mixture of isomers.

NMR $^1$H (400 MHz in acetone-d$_6$) δ 8.92 (m, 1H), 8.45 (m, 1H), 8.10 (m, 1H), 8.05 (m, 1H), 7.93 (m, 1H), 7.85 (m, 2H), 7.77–7.55 (m, XH), 7.40 (t(minor), 0.43H), 7.28 (t, (major), 0.57H), 7.21 (d(minor), 0.43H), 7.10(d(major), 0.57H), 4.67 (s,(major), 0.57H), 4.63 (s(minor), 0.43H), 3.15 (s(minor), 1.3H), 2.99 (s(major), 1.7H), 1.90 (m, 6H), 1.65 (s,(major), 3.4H), 1.45 (s(minor), 2.6H). MS (m+1): 594.6.

EXAMPLE 9

2-Methyl-2-[8-(3-{(E)-2-(1-methyl-1H-imidazol-2-yl)-2-[4-(methylsulfonyl)phenyl]ethenyl}phenyl)-6-quinolinyl]propanenitrile Example 9 was Prepared by the Following Procedure.

Step 1: 2-methyl-2-[8-(3-{(E)-2-(1-methyl-1H-imidazol-2-yl)-2-[4-(methylthio)phenyl]ethenyl}phenyl)-6-quinolinyl]propanenitrile was prepared by following the procedure for Example 1 but substituting the ketone K2 for K3 and the benzyl phosphonate P3 for P2 as the starting materials.

Step 2: 2-methyl-2-[8-(3-{(E)-2-(1-methyl-1H-imidazol-2-yl)-2-[4-(methylsulfonyl)phenyl]ethenyl}phenyl)-6-quinolinyl]propanenitrile, Example 9, was prepared by following the procedure used for the preparation of the boronate B1 (step 2 of Scheme 2) but substituting the sulfide obtained in present step 1 for (E/Z)-2-(3-Bromophenyl)-1-(1-methyl-1H-imidazol-2-yl)-1-[4-(methylthio)phenyl] ethene as the starting material. Example 9 was obtained after purification by flash chromatography (97%EtOAc/3%Et$_3$N).

NMR $^1$H (400 MHz in acetone-d$_6$) δ 8.92 (dd, 1H), 8.45 (dd, 1H), 8.10 (d, 1H), 7.93 (d, 2H), 7.76 (d, 1H), 7.60–7.50 (m, 5H), 7.38 (t, 1H), 7.35 (s, 1H), 7.19 (m, 1H), 7.10 (m, 1H), 6.95 (m, 1H), 3.55 (s, 3H), 3.00 (s, 3H), 1.85 (s, 6H). MS (m+1): 533.3.

EXAMPLE 10

6-[1-(Methylsulfonyl)ethyl]-8-{3-[(E)-2-[4-(methylsulfonyl)phenyl]-2-(1,3-thiazol-2-yl)ethenyl] phenyl}quinoline Example 10 was prepared by the following procedure. A mixture of bromoquinoline Q2 (105 mg, 0.33 mmol), boronate B2 (236 mg, 0.51 mmol), Na$_2$CO$_3$ (2M, 0.65 mL, 1.3 mmol), Pd(OAc)$_2$ (6.3 mg, 0.028 mmol) and PPh$_3$ (28 mg, 0.11 mmol) in 4 mL of n-propanol was stirred at 90° C. for 2 h. The mixture was cooled to r.t., diluted with EtOAc, washed with brine, dried over Na$_2$SO$_4$, filtered and concentrated. Flash chromatography (Tol/Acetone; 4/1) and stirring in Hexane/EtOAc yielded Example 10 (single isomer) as a white solid.

NMR $^1$H (400 MHz, Acetone-d$_6$) δ 8.89 (dd, 1H), 8.39 (dd, 1H), 8.07 (d, 1H), 8.03 (d, 2H), 7.94 (s, 1H), 7.86 (d, 1H), 7.71–7.68 (m, 3H) 7.62–7.60 (m, 2H), 7.55 (dd, 1H), 7.45 (s, 1H) 7.34 (t, 1H), 7.18 (d, 1H), 4.67 (q, 1H), 3.04 (s, 3H), 2.86 (s, 3H) 1.88 (s,3H) MS (M+1) 576.

EXAMPLE 11

6-[1-Methyl-1-(methylsulfonyl)ethyl]-8-{3-[(E)-2-[4-(methylsulfonyl)phenyl]-2-(1,3-thiazol-2-yl) ethenyl]phenyl}quinoline Example 11 was prepared by following the procedure described in Example 10 but substituting bromoquinoline Q3 for Q2 and using boronate B2. Flash chromatography (Tol/Acetone; 9/1) and stirring in EtOAc/Hex yielded Example 11 (single isomer) as a white solid.

NMR $^1$H (400 MHz, Acetone-d$_6$): δ 8.90 (dd, 1H), 8.41 (dd, 1H), 8.23 (s, 1H), 8.02–7.99 (d, 3H), 7.95 (s, 1H), 7.86 (d, 1H), 7.70 (d, 2H), 7.60–7.54 (m, 4H), 7.32 (t, 1H), 7.13 (d, 1H), 3.00 (s, 3H), 2.69 (s, 3H), 1.96 (s, 6H). MS (M+1) 523.

EXAMPLE 12

8-(3-{(Z)-2-(1-Methyl-1H-imidazol-2-yl)-2-[4-(methylsulfonyl)phenyl]ethenyl}phenyl)-6-[1-(methylsulfonyl)ethyl]quinoline Example 12 was prepared following the procedure described in Example 10 using the bromoquinoline Q2 but substituting the boronate B1 for boronate B2. Flash chromatography (95%CH$_2$Cl$_2$/5%EtOH) yielded the Example 12 compound.

NMR $^1$H (400 MHz in acetone-d$_6$) δ 8.92 (dd, 1H), 8.45 (dd, 1H), 8.10 (s, 1H), 7.93 (d, 2H), 7.76–7.65 (m, 4H), 7.59 (dd, 1H), 7.39 (t, 1H), 7.26 (s, 1H), 7.18 (s, 1H), 7.05 (m, 2H), 4.70 (q, 1H), 3.40 (s, 3H), 3.13 (s, 3H), 2.93 (s, 3H), 1.87 (d, 3H). MS (m+1): 572.4.

EXAMPLE 13

8-(3-{(Z)-2-(1-Methyl-1H-imidazol-2-yl)-2-[4-(methylsulfonyl)phenyl]ethenyl}phenyl)-6-[1-methyl-1-(methylsulfonyl)ethyl]quinoline Example 13 was prepared following the procedure described in Example 10 but substituting the bromoquinoline Q3 for Q2 and substituting the boronate B1 for boronate B2. Flash chromatography (95%EtOAc/5%Et$_3$N) produced Example 13 (single isomer) as a foam.

NMR $^1$H (400 MHz in acetone-d$_6$) δ 8.92 (dd, 1H), 8.45 (dd, 1H), 8.37 (d, 1H), 8.05 (d, 1H), 7.93 (d, 2H), 7.76 (d, 1H), 7.69 (d, 2H), 7.65 (d, 1H), 7.59 (dd, 1H), 7.38 (t, 1H), 7.31 (s, 1H), 7.18 (s, 1H), 7.05 (m, 2H), 3.40 (s, 3H), 3.13 (s, 3H), 2.70 (s, 3H), 1.95 (s, 6H). MS (m+1): 586.2.

EXAMPLES 14 and 15

6-[1-Methyl-1-(methylsulfonyl)ethyl]-8-(3-{(E/Z)-2-(3-methyl-1,2,4-oxadiazol-5-yl)-2-[4-(methylsulfonyl)phenyl])ethenyl}phenyl)quinoline

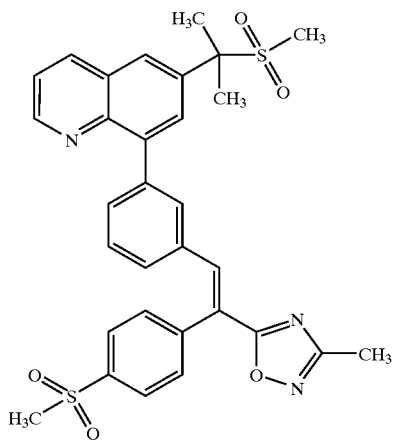

EXAMPLE 14

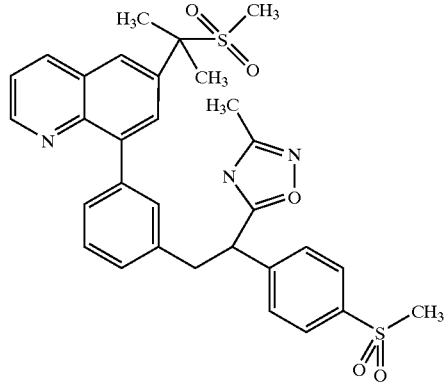

Example 15

Examples 14 and 15 were prepared by the following procedure. A solution of the aryl bromide AB5 (249 mg, 0.57 mmol), diboron pinacol ester (167 mg, 0.66 mmol), [1,1'-bis(diphenylphosphino)-ferrocene]dichloropalladium(II) (12 mg, 0.015 mmol) and potassium acetate (176 mg, 1.8 mmol) in DMF (N,N-Dimethylformamide) (10 mL) was degassed and stirred at 80° C. for 3 h. To that resulting mixture at 25° C. was then added the bromoquinoline Q3 (150 mg, 0.46 mmol), [1,1'-bis(diphenylphosphino)-ferrocene]dichloropalladium(II) (12 mg, 0.015 mmol) and sodium carbonate (0.6 mL, 2M). After degassing, the mixture was heated at 80° C. overnight. The mixture was then cooled to r.t. quenched with H$_2$O, and extracted with EtOAc. The organic extracts were washed (H$_2$O, brine), dried (MgSO$_4$), filtered and concentrated. Purification by flash chromatography (hexane:EtOAc:Et$_3$N, 22:68:10 then hexane:EtOAc, 3:1) yielded both isomers (Example 14 and Example 15).

NMR $^1$H (500 MHz, Acetone-d$_6$) Major(E) isomer (Example 14): δ 8.91 (dd, 1H), 8.42 (dd, 1H), 8.25 (d, 1H), 8.12 (s, 1H), 8.02 (d, 1H), 8.00 (d, 2H), 7.70 (m, 3H), 7.64 (s, 1H), 7.55 (dd, 1H), 7.38 (t, 1H), 7.23 (d, 1H), 3.03 (s, 3H), 2.69 (s, 3H), 2.33 (s, 3H), 1.96 (s, 6H). MS (M+1): 588.2.

Minor(Z) isomer (Example 15): δ 8.92 (dd, 1H), 8.45 (dd, 1H), 8.29 (d, 1H), 8.07 (d, 1H), 7.99 (d, 2H), 7.88 (s, 1H), 7.75 (m, 3H), 7.62 (s, 1H), 7.58 (q, 1H), 7.48 (t, 1H), 7.24 (d, 1H), 3.16 (s, 3H), 2.70 (s, 3H), 2.38 (s, 3H), 2.00 (s, 6H). MS (M+1): 588.2.

Alternatively, Example 14 can be made by the following procedure:

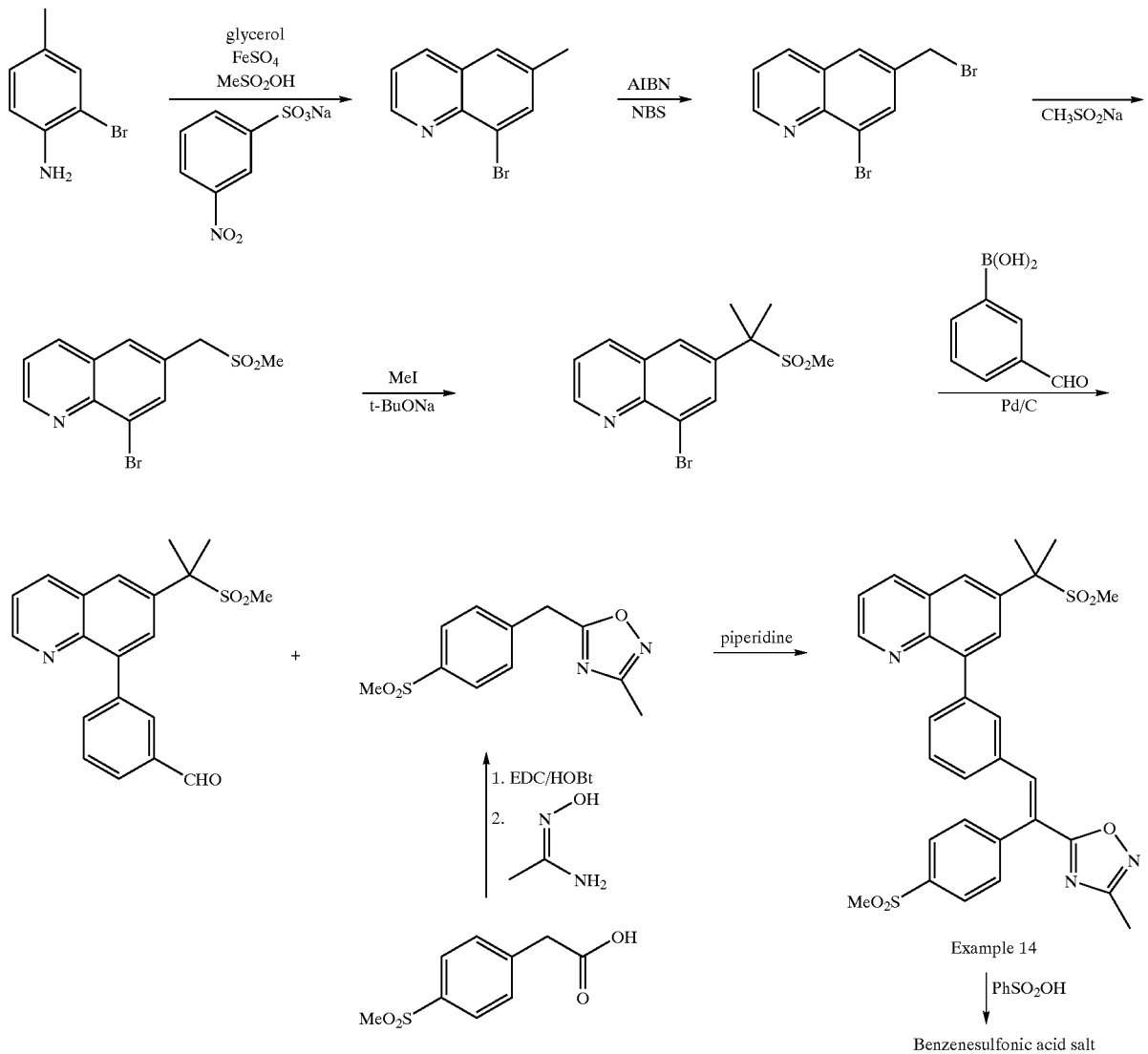

Example 14

Benzenesulfonic acid salt

Step 1. Skraup Reaction

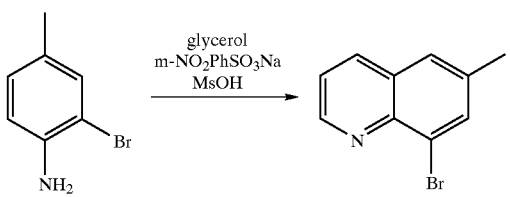

To methanesulfonic acid (8–10 equiv.) at 20° C. was added sodium m-nitrobenzenesulfonate (0.6–0.8 equiv.), followed by iron sulfate heptahydrate (0.01–0.05 equiv.). To the resulting mixture was added 2-bromo-4-methylaniline (1 equiv.).

Glycerol (2–3 equiv.) was added and the resulting solution was heated at 120–140° C. and aged until the reaction was complete.

The mixture was cooled to 70–90° C. and diluted with water. The solution was then cooled to about 20° C., and neutralized with aqueous NaOH and sodium bicarbonate. MTBE (methyl t-butyl ether) was added and the mixture was filtered and the phases were separated (the product was in the MTBE layer).

Step 2. Bromination

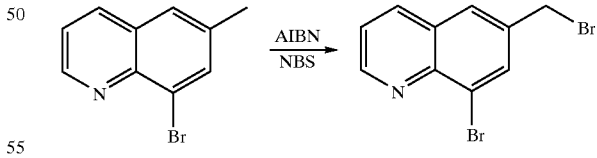

The MTBE solution from step 1 was solvent switched to chlorobenzene. After filtered through Silica gel and partially concentrated, N-bromosuccinimide (NBS, 0.6–0.8 equiv.) and 2,2'-azobisisobutylnitrile (AIBN, 0.01–0.1 equiv.) were added. The degassed mixture was heated at 55–85° C. The resulting mixture was diluted with cyclohexane. Additional NBS (0.3–0.5 equiv.) and AIBN (0.01–0.05 equiv.) were added. The degassed mixture was heated at about 55–85° C. until reaction completed. The mixture was cooled at 10–40° C. and diluted with cyclohexane and aged. The solid was isolated by filtration.

Step 3. Sulfone Formation

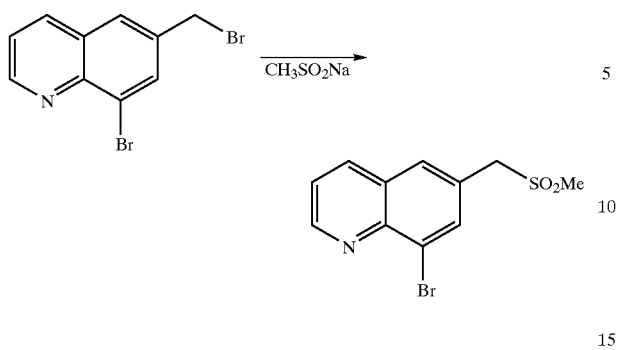

To a solution of bromomethyl-bromoquinoline (product from previous step, 1 equiv.) in DMF was added powdered sodium methanesulfinate (1.0–1.5 equiv.) at 10–60° C. The mixture was heated at about 50–70° C. for 30 min. The mixture was diluted with water while maintaining temp at about 50–70° C. with vigorous stirring, then cooled to, about 10–20° C. and aged. The mixture was filtered and the solid washed sequentially with 1:4 DMF/water and then water and dried.

Step 4. Methylation

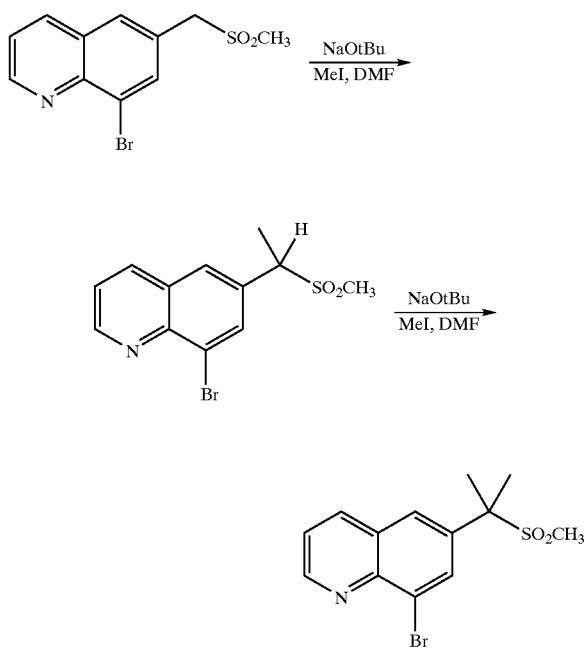

A solution of the sulfone (product from the previous step, 1 equiv.) in DMF was cooled to about −10 to 0° C. Sodium t-butoxide (~1 equiv.) was added. A solution of methyl iodide/DMF solution (~1 equiv. of MeI) was added slowly while maintaining temperature at about −10 to 0° C.

A second portion of solid sodium t-butoxide (~1 equiv.) was added, followed by methyl iodide/DNF solution (~1 equiv.) was added while maintaining the temperature at −5 to 10° C. (Additional base and MeI may be added if the reaction was not completed). The reaction was quenched by addition of water and the product crystallized, which was isolated and dried.

Step 5. Suzuki Coupling

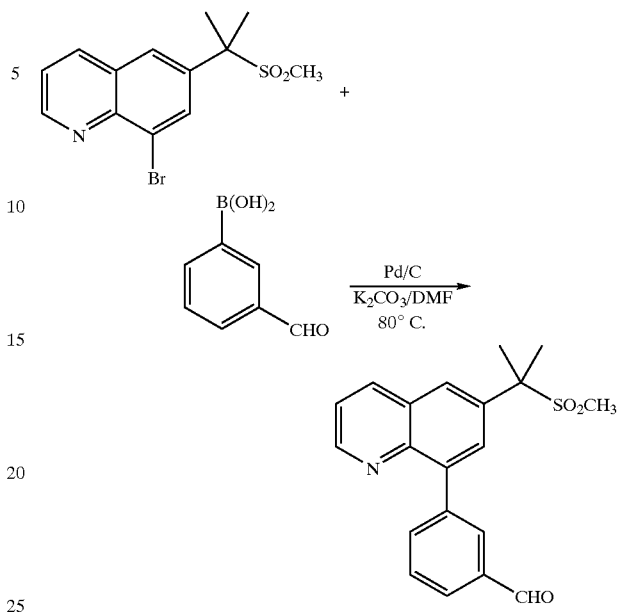

To a solution of the sulfone from the previous step (1 equiv.) was added Pd/C (5 or 10 w %, 0.005–0.1 equiv.), potassium carbonate (2–3 equiv.), and 3-formyl phenylboronic acid (1–2 equiv.). The degassed reaction mixture was heated at 60–120° C. until the reaction was complete. The mixture was filtered and the filtrate was diluted with water. The product crystallized and was isolated by filtration and dried.

Step 6. Oxadiazole

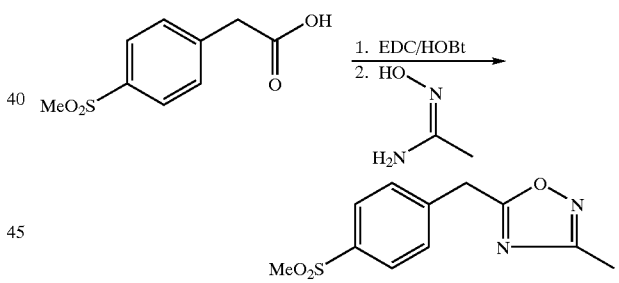

To the mixture of hydroxy benzotriazole ("HOBt") hydrate (1–1.5 equiv.), 4-methylsulfonylphenylacetic acid (1 equiv.) in acetonitrile was added EDC hydrochloride (1–1.5 equiv.). The slurry was aged at about 20–30° C. for 30 min.

Other N—OH compounds, such as N-hydroxyphthalimide, 2-hydroxypyridine N-oxide, N-hydroxysuccinimide, can also be used to replace HOBt. Other carbodiimides, such as dicyclohexylcarbodiimide and diisopropylcarbodiimide can be used to replace EDC hydrochloride (ethyl dimethylaminopropylcarbodiimide hydrochloride).

To the slurry was added acetamide oxime (1–1.5 equiv.). The resulting mixture was then heated at reflux until the reaction was complete. The resulting solution was concentrated and diluted with ethyl acetate. To the resulting mixture was washed with aqueous sodium bicarbonate. The solution was solvent switched to 2-propanol and product crystallized upon cooling, which was isolated and dried.

49
Step 7. Condensation to form Example 14

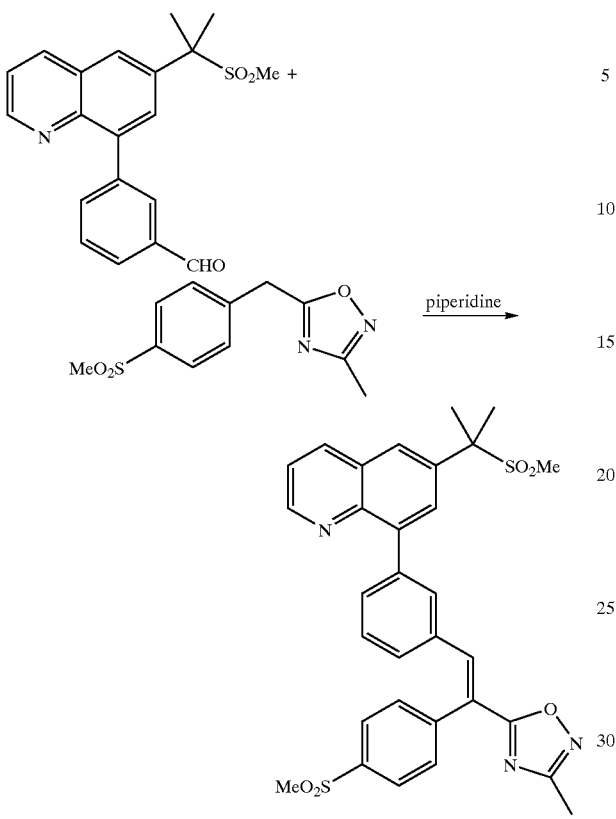

To a slurry of the aldehyde from step 5 above (1 equiv.) in 2-propanol was added the oxadiazole from step 6 above (1–1.5 equiv.), followed by piperidine (0.2–1.5 equiv.).

In place of 2-propanol, other solvents such as, for example, DMF, acetonitrile, 1-propanol, toluene, esters, and other alcohols. Piperidine serves as a basic initiator. In place of piperidine, other amine bases, especially secondary amines, can be used.

The resulting mixture was heated at reflux over molecular sieves until reaction completed. After cooling, the product was isolated by filtration and dried.

EXAMPLES 16 and 17

(E/Z)-3-{3-[6-(1-Cyano-1-methylethyl)-8-quinolinyl]phenyl}-N-isopropyl-2-[4-(methylsulfonyl)phenyl]-2-propenamide Examples 16 and 17 were prepared following the procedure described previously for Examples 14 and 15 but substituting the aryl bromide AB2 for AB5 and the bromoquinoline Q5 for Q3 as the starting materials. Examples 16 and 17 were obtained as a 4:1 mixture.

NMR $^1$H (500 MHz, Acetone-$d_6$) Major(E) isomer (Example 16): δ 8.89 (dd, 1H), 8.43 (dd, 1H), 8.09 (d, 1H), 7.90 (d, 2H), 7.81 (d, 1H), 7.68 (s, 1H), 7.57 (m, 4 H), 7.45 (s, 1H), 7.29 (t, 1H), 7.04 (d, 1H), 6.71 (bd, 1H), 4.13 (m, 1H), 2.92 (s, 3H), 1.87 (s, 6H), 1.12 (d, 6H). MS (M+1): 538.3.

Minor(Z) isomer (Example 17): δ 8.93 (dd, 1H), 8.48 (dd, 1H), 8.14 (d, 1H), 7.94 (m, 4H), 7.85 (d, 2H), 7.70 (dd, 2H), 7.59 (q, 1H), 7.50 (m, 2H), 7.28 (s, 1H), 4.15 (m, 1H) 3.13 (s, 3H), 1.91 (s, 6H), 1.04 (d, 6H). MS (M+1): 538.3.

50

EXAMPLE 18

8-(3-{(E)-2-{3-[(4-Methoxyphenoxy)methyl]-1,2,4-oxadiazol-5-yl}-2-[4-(methylsulfonyl)phenyl] ethenyl}phenyl)-6-[1-methyl-1-(methylsulfonyl) ethyl]quinoline Example 18 was Prepared by the Following Procedure.

Step 1 (Scheme 3): (4-methoxyphenoxy)acetonitrile

A mixture of 4-methoxyphenol (10 g, 80 mmol), chloroacetonitrile (7.0 mL, 111 mmol) and $K_2CO_3$ (26 g, 188 mmol) in acetone (150 mL) was stirred at r.t. for 18 h. The mixture was filtered, concentrated and purified by flash chromatography (Hex:EtOAc, 4:1) to yield (4-methoxyphenoxy)acetonitrile as a clear oil.

Step 2 (Scheme 3): (4-methoxyphenoxy)acetamide oxime

A mixture of the (4-methoxyphenoxy)acetonitrile product (5.0 g, 31 mmol) from step 1, hydroxylamine hydrochloride (4.3 g, 62 mmol) and sodium acetate (5.1 g, 62 mmol) in MeOH (100 mL) was stirred at r.t. for 2 h. The resulting mixture was filtered on Celite®, concentrated, stirred in $CHCl_3$ for 18 h and filtered. The resulting solution was concentrated to yield (4-methoxyphenoxy)acetamide oxime as a gum.

Step 3 (Scheme 3, Oxadiazole OX2): 3-[(4-methoxyphenoxy)methyl]-5-[4-(methylsulfonyl)benzyl]-1,2,4-oxadiazole 3-[(4-methoxyphenoxy)methyl]-5-[4-(methylsulfonyl)benzyl]-1,2,4-oxadiazole was prepared following the procedure as described in Scheme 3 for AB5 step 1 (OX1) but substituting the (4-methoxyphenoxy)acetamide oxime from step 2 above for acetamide oxime and heating the reaction at 90° C. for 6 h. Purification by flash chromatography (Hex:EtOAc, 3:2 to 1:4) yielded the desired material as a pale brown solid.

Step 4: 3-{6-[1-methyl-1-(methylsulfonyl)ethyl]-8-quinolinyl}benzaldehyde

To bromoquinoline Q3 (10.1 g, 30.9 mmol) 3-formylbenzeneboronic acid (5.8 g, 38.7 mmol), tetrakis(triphenylphosphine)-palladium (0) (2.1 g 1.86 mmol) and sodium carbonate (39 mL, 2M ) was added DME (330 mL). After degassing, the mixture was heated at 80° C. overnight. After cooling to r.t. the resulting mixture was quenched with $H_2O$, and extracted with EtOAc. The organic extracts were washed ($H_2O$, brine), dried ($MgSO_4$), filtered and concentrated. Stirring in ether, followed by isolation by filtration gave 3-{6-[1-methyl-1-(methylsulfonyl)ethyl]-8-quinolinyl}benzaldehyde.

Step 5: 8-(3-{(E)-2-{3-[(4-methoxyphenoxy)methyl]-1,2,4-oxadiazol-5-yl}-2-[4-(methylsulfonyl)phenyl] ethenyl}phenyl)-6-[1-methyl-1-(methylsulfonyl)ethyl]quinoline A mixture of the product from present step 4 (150 mg, 0.42 mmol), the oxadiazole OX2 from present step 3 above (175 mg, 0.47 mmol) and piperidine (0.1 mL, 1.0 mmol) in toluene (0.6 mL) was heated at 120° C. for 3 h. The mixture was purified by flash chromatography (Hex:EtOAc, 3:2 to 1:4) to yield Example 18 as a foam.

NMR $^1$H (400 MHz, Acetone-$d_6$) δ 8.90 (q, 1H), 8.42 (q, 1H), 8.24 (d, 1H), 8.20 (s, 1H), 8.02 (m, 3H), 7.75–7.66 (m, 4H), 7.55 (q, 1H), 7.39 (t, 1H), 7.25 (d, 1H), 7.00 (d, 2H), 6.87 (d, 2H), 5.17 (s, 2H), 3.73 (s, 3H), 3.03 (s, 3H), 2.80 (s, 3H), 1.96 (s, 6H).

EXAMPLE 19

(5-{(E)-2-(3-{6-[1-Methyl-1-(methylsulfonyl)ethyl]-8-quinolinyl}phenyl)-1-[4-(methylsulfonyl)phenyl] ethenyl}-1,2,4-oxadiazol-3-yl)methanol Example 19 was prepared by the following procedure. To a solution of the Example 18 compound (250 mg, 0.35 mmol) in acetonitrile:water (4:1, 8 mL) was added CAN (330 mg, 0.62 mmol) in two portions at r.t. After 3 h at r.t., the mixture was diluted with saturated NaHCO$_3$ solution, diluted with water and extracted with EtOAc. The organic extracts were washed (H$_{2O}$), (brine), dried (MgSO$_4$), filtered and concentrated. Purification by flash chromatography (Hex:EtOAc, 3:7) yielded (5-{(E)-2-(3-{6-[1-methyl-1-(methylsulfonyl)ethyl]-8-quinolinyl}phenyl)-1-[4-(methylsulfonyl)phenyl]ethenyl}-1,2,4-oxadiazol-3-yl) methanol as a pale yellow foam.

NMR $^1$H (400 MHz, Acetone-d$_6$) δ 8.90 (q, 1H), 8.42 (q, 1H), 8.25 (d, 1H), 8.15 (s, 1H), 8.02 (m, 3H), 7.73–7.65 (m, 4H), 7.55 (q, 1H), 7.38 (t, 1H), 7.23 (d, 1H), 4.67 (m, 3H), 3.04 (s, 3H), 2.82 (s, 3H), 1.96 (s, 6H).

EXAMPLE 20

(E)—N-Isopropyl-3-(3-{6-[1-methyl-1-(methylsulfonyl)ethyl]-8-quinolinyl}phenyl)-2-[4-(methylsulfonyl)phenyl]-2-propenamide Example 20 was prepared by following the procedure described above for Examples 14 and 15 but substituting the aryl bromide AB2 for AB5, and using the bromoquinoline Q3, as the starting materials.

NMR $^1$H (300 MHz, Acetone-d$_6$) δ 8.89 (dd, 1H), 8.41 (dd, 1H), 8.22 (d, 1H), 7.99 (d, 1H), 7.88 (d, 2H), 7.67 (s, 1H), 7.53 (m, 4H), 7.43 (s, 1H), 7.28 (t, 1H), 7.05 (d, 1H), 6.71 (bd, 1H), 4.14 (m, 1H) 2.9 (s, 3H), 1.95 (s, 6H), 1.13 (d, 6H). MS(M+1): 591.3.

EXAMPLE 21

(E)-3-{3-[6-(1-Cyano-1-methylethyl)-8-quinolinyl] phenyl}-2-[4-(methylsulfonyl)phenyl]-2-propenoic acid Example 21 was prepared by following the procedure described above for Examples 14 and 15 but substituting the aryl bromide AB1 for AB5 and the bromoquinoline Q5 for Q3 as the starting materials.

NMR $^1$H (500 MHz, Methanol) δ 8.8 (dd, 1H), 8.38 (dd, 1H), 8.04 (d, 2H), 7.88 (d, 2H), 7.66 (d, 1H), 7.55 (m, 4H), 7.36 (t, 1H), 7.29 (s, 1H), 7.18 (d, 1H), 2.93 (s, 3H), 1.88 (s, 6H). MS (M—CO$_2$): 451.4 (negative ion).

EXAMPLE 22

2-Methyl-2-[8-(3-{(E)-2-(3-methyl-1,2,4-oxadiazol-5-yl)-2-[4-(methylsulfonyl)phenyl]ethenyl}phenyl)-6-quinolinyl]propanenitrile Example 22 was prepared by following the procedure described for Examples 14 and 15 using the aryl bromide AB5 and substituting the bromoquinoline Q5 for Q3 as the starting materials.

NMR $^1$H (500 MHz, Acetone-d$_6$) δ 8.90 (dd, 1H), 8.43 (dd, 1H), 8.1 (d, 2H), 8.01 (d, 2H), 7.83 (d, 1H), 7.71 (t, 3H), 7.66 (s, 1H), 7.56 (q, 1H) 7.55 (dd, 1H), 7.38 (t, 1H), 7.22 (d, 1H), 3.03 (s, 3H), 2.33 (s, 3H), 1.87 (s, 6H) MS (M+1): 535.2.

EXAMPLE 23

(E)-3-{3-[6-(1-Cyano-1-methylethyl)-8-quinolinyl] phenyl}-2-[4-(methylsulfonyl)phenyl]-2-propenamide Example 23 was prepared by following the procedure described above for Examples 14 and 15 but substituting the aryl bromide AB3 for AB5 and the bromoquinoline Q5 for Q3 as the starting materials, the title compound was obtained.

NMR $^1$H (500 MHz, Acetone-d$_6$) δ 8.89 (dd, 1H), 8.43 (dd, 1H), 8.08 (d, 1H), 7.93 (d, 2H), 7.8 (d, 2H), 7.6 (m, 4H), 7.48 (s, 1H), 7.31 (t, 1H), 7.08 (d, 1H), 6.6 (bs, 1H), 6.7 (bs, 1H), 2.93 (s, 3H), 1.87 (s, 6H).

EXAMPLE 24

(E)—N-(tert-Butyl)-3-{3-[6-(1-cyano-1-methylethyl)-8-quinolinyl]phenyl}-2-[4-(methylsulfonyl)phenyl]-2-propenamide Example 24 was prepared by following the procedure described for Examples 14 and 15 but substituting the aryl bromide AB4 for AB5 and the bromoquinoline Q5 for Q3 as the starting materials.

NMR $^1$H (500 MHz, Acetone-d$_6$) δ 8.89 (dd, 1H), 8.43 (dd, 1H), 8.08 (d, 1H), 7.92 (d, 2H), 7.79 (d, 1H), 7.58 (m, 5H), 7.45 (s, 1H), 7.29 (t, 1H), 7.04 (d, 1H), 6.4 (bs, 1H), 2.93 (s, 3H), 1.87 (s, 6H), 1.36 (s, 9H). MS (M+1)553.

EXAMPLE 25

(E)-3-[3-(6-Isopropyl-8-quinolinyl)phenyl]-2-[4-(methylsulfonyl)phenyl]-2-propenoic Acid Example 25 was prepared by following the procedure described for Examples 14 and 15 but substituting the aryl bromide AB1 for AB5, and 5-isopropyl-8-bromoquinoline (described in International Patent Publication W09422852) for Q3, as the starting materials.

NMR $^1$H (500 MHz, Acetone-d$_6$) δ 8.69 (dd, 1H), 8.26 (dd, 1H), 7.85 (s, 1H), 7.83 (d, 2H), 7.68 (s, 1H), 7.51 (d, 2H), 7.49 (m, 2H), 7.36 (dd, 1H), 7.31 (t, 1H), 7.20 (s, 1H), 7.13 (d, 1H), 3.1 (m, 1H), 2.93 (s, 3H), 1.36 (d, 6H). MS (M+1) 472.

EXAMPLE 26

6-Isopropyl-8-(3-{(E)-2-(3-methyl-1,2,4-oxadiazol-5-yl)-2-[4-(methylsulfonyl)phenyl]ethenyl}phenyl) quinoline Example 26 was prepared by following the procedure described for Examples 14 and 15 using the aryl bromide AB5, and substituting 5-isopropyl-8-bromoquinoline (described in International Patent Publication W09422852) for Q3 as the starting materials.

NMR $^1$H (500 MHz, Acetone-d$_6$) δ 8.80 (dd, 1H), 8.29 (dd, 1H), 8.12 (s, 1H), 8.03 (d, 2H), 7.76 (s, 1H), 7.73 (m, 3H), 7.59 (s, 1H), 7.53 (d, 1H), 7.47 (q, 1H), 7.36 (t, 1H), 7.22 (d, 1H), 3.1 (m, 1H), 2.93 (s, 3H), 2.33 (s, 3H) 1.36 (d, 6H). MS (M+1) 510.

EXAMPLE 27

(E)-3-(3-{6-[1-Methyl-1-(methylsulfonyl)ethyl]-8-quinolinyl}phenyl)-2-[4-(methylsulfonyl)phenyl]-1-(1-pyrrolidinyl)-2-propen-1-one Example 27 was Prepared by the Following Procedure.

Step 1: (E)-3-(3-{6-[1-methyl-1-(methylsulfonyl)ethyl]-8-quinolinyl}phenyl)-2-[4-(methylsulfonyl)phenyl]-2-propenoic acid. A mixture of 3-{6-[1-methyl-1-(methylsulfonyl)ethyl]-8-quinolinyl}benzaldehyde from step 4 of Example 18 (2.33 g, 6.60 mmol), 4-(methylsulfonyl)phenyl acetic acid (1.71 g, 7.98 mmol) and piperidine (0.20 mL, 1.98 mmol) in 10 mL of toluene was refluxed for 2 days. The mixture was cooled to r.t., diluted with CH$_2$Cl$_2$, subjected to flash chromatography (CH$_2$Cl$_2$/EtOAc/AcOH, 50/50/1) and finally stirred with (Et$_2$O/CH$_2$Cl$_2$) and isolated to give (E)-3-(3-{6-[1-methyl-1-(methylsulfonyl)ethyl]-8-quinolinyl}phenyl)-2-[4-(methylsulfonyl)phenyl]-2-propenoic acid (single isomer) as a white solid.

NMR $^1$H (400 MHz, Acetone-d$_6$): δ 8.89 (dd, 1H), 8.39 (dd, 1H), 8.07 (d, 1H), 8.03 (d, 2H), 7.94 (s, 1H), 7.86 (d, 1H), 7.71–7.68 (m, 3H) 7.62–7.60 (m, 2H), 7.55 (dd, 1H), 7.45 (s, 1H) 7.34 (t, 1H), 7.18 (d, 1H), 4.67 (q, 1H), 3.04 (s, 3H), 2.86 (s, 3H) 1.88 (s,3H). MS (M+1) 576.

Step 2: (E)-3-(3-{6-[1-methyl-1-(methylsulfonyl)ethyl]-8-quinolinyl}phenyl)-2-[4-(methylsulfonyl)phenyl]-1-(1-pyrrolidinyl)-2-propen-1-one A mixture of (E)-3-(3-{6-[1-methyl-1-(methylsulfonyl)ethyl]-8-quinolinyl}phenyl)-2-[4-(methylsulfonyl)phenyl]-2-propenoic acid (104 mg, 0.19 mmol) from the present step 1 above, pyrrolidine (24 µL, 0.29 mmol), EDCI (1-(3-Dimethylaminopropyl)-3-ethylcarbodiimide hydrochloride) (55 mg, 0.29 mmol) and HOBt (1-Hydroxybenzotriazole hydrate) (34 mg, 0.25 mmol) in 1 mL of DMF was stirred at r.t. for 12 h. The mixture was diluted with EtOAc, washed with NH$_4$Cl (sat), H$_2$O (3×), brine, dried over Na$_2$SO$_4$, filtered and concentrated. Stirring in EtOAc/Hex yielded Example 27 as a white solid.

NMR $^1$H (400 MHz, Acetone-d$_6$): δ 8.88 (dd, 1H), 8.40 (dd, 1H), 8.22 (d, 1H), 8.98 (d, 1H), 7.88 (d, 2H), 7.67 (d, 2H), 7.60 (d, 1H) 7.55–7.52 (m, 2H) 7.34 (t, 1H), 7.18 (d, 1H), 7.03 (bs, NH) 3.58 (bs, 2H), 3.44 (bs, 2H), 3.02 (s, 3H), 2.69 (s, 3H) 1.95 (s, 6H), 1.88 (bs, 4H). MS (M+1) 603.

EXAMPLE 28

(E)—N-cyclopropyl-3-(3-{6-[ 1-methyl-1-(methylsulfonyl)ethyl]-8-quinolinyl}phenyl)-2-[4-(methylsulfonyl)phenyl]-2-propenamide Example 28 was prepared by following the procedure for step 2 of Example 27 but substituting cyclopropyl amine for pyrrolidine, thus yielding a white solid.

NMR $^1$H (400 MHz, acetone-d$_6$): δ 8.89 (dd, 1H), 8.41 (dd, 1H), 8.23 (d, 1H), 7.98 (d, 1H), 7.87 (d, 2H), 7.68 (s, 1H), 7.59–7.53 (m, 4H), 7.43 (s, 1H), 7.29 (t, 1H), 7.04 (d, 1H), 6.94 (bs, 1H), 2.89 (s, 3H), 2.84–2.80 (m, 1H), 2.69 (s, 3H), 1.96 (s, 6H), 0.67–0.63 (m, 2H), 0.49–0.45 (m, 2H). MS (M+1) 589.

EXAMPLE 29

(E)—N-(tert-Butyl)-3-(3-{6-[1-methyl-1-(methylsulfonyl)ethyl]-8-quinolinyl}phenyl)-2-[4-(methylsulfonyl)phenyl]-2-propenamide Example 29 was prepared as a white solid by following the procedure for step 2 of Example 27 but substituting t-butyl amine amine for pyrrolidine.

NMR $^1$H (400 MHz, acetone-d$_6$): δ 8.89 (dd, 1H), 8.41 (dd, 1H), 8.23 (d, 1H), 7.98 (d, 1H), 7.90 (d, 2H), 7.59–7.53 (m, 5H), 7.43 (s, 1H), 7.30 (t, 1H), 7.05 (d, 1H), 6.43 (bs, 1H), 2.94 (s, 3H), 2.69 (s, 3H), 1.96 (s, 6H), 1.36 (s, 9H MS (M+1) 606.

EXAMPLE 30

8-{3-[2,2-bis(4-Chlorophenyl)vinyl]phenyl}-6-isopropylquinoline

Example 30 was Prepared by the Following Procedure. To a mixture of the benzylphosphonate P2 (100 mg, 0.25 mmol), 4,4'-dichlorobenzophenone (63 mg, 0.25 mmol),) in THF (2 mL) at r.t. was added potassium t-butoxide (1M, THF, 0.35 mL, 0.35 mmol). After 1 h at r.t., the mixture was diluted with water/NH$_4$Cl and extracted with EtOAc. The organic extracts were washed (H$_2$O), (brine), dried (MgSO$_4$), filtered and concentrated. Purification by flash chromatography (Hex:EtOAc, 8:2) yielded Example 30 as a white foam.

NMR $^1$H (300 MHz, acetone-d$_6$) δ 8.79 (dd, 1H), 8.28 (dd, 1H), 7.74 (d, 1H), 7.60 (d, 1H), 7.48–7.25 (m, 12H), 7.20–7.16 (m, 2H) 3.13 (hept, 1H), 1.36 (d, 6H).

EXAMPLES 31 AND 32

6-Isopropyl-8-(3-{(E/Z)-2-(6-methyl-3-pyridinyl)-2-[4-(methylsulfonyl)phenyl]ethenyl}phenyl)quinoline Examples 31 and 32 were prepared by following the procedure described for Example 30 but substituting the ketone K7 for 4,4'-dichlorobenzophenone and using the benzylphosphonate P2 as the starting materials.

NMR $^1$H (300 MHz, Acetone-d$_6$) (E) isomer (Example 31): δ 8.79 (dd, 1H), 8.43 (d, 1H), 8.27 (dd, 1H), 7.95 (d, 2H), 7.73 (d, 1H), 7.57–7.43 (m, 7H), 7.32–7.19 (m, 3H), 7.10 (d, 1H), 3.15 (hept, 1H), 2.98 (s, 3H), 1.34 (d, 6H).

(Z) isomer (Example 32): δ 8.79 (dd, 1H), 8.35 (d, 1H), 8.28 (dd, 1H), 7.92 (d, 2H), 7.74 (d, 1H), 7.61–7.30 (m, 10H), 7.19 (d, 1H), 3.13 (s, 3H), 3.11 (hept, 1H), 1.35 (d, 6H).

EXAMPLES 33 AND 34

6-Isopropyl-8-(3-{(EZ)-2-(5-methyl-2-pyridinyl)-2-[4-(methylsulfonyl)phenyl]ethenyl}phenyl)quinoline Examples 33 and 34 were prepared by following the procedure described for Example 30 but substituting the ketone K8 for 4,4'-dichlorobenzophenone and using the benzylphosphonate P2 as the starting materials.

NMR $^1$H (300 MHz, Acetone-d$_6$) (E) isomer (Example 33): δ 8.80 (dd, 1H), 8.48 (s, 1H), 8.28 (dd, 1H), 7.99–7.96 (m, 3H), 7.97 (m, 1H), 7.74 (d, 1H), 7.61–7.44 (m, 6H), 7.27 (t, 1H), 7.07 (d, 1H), 6.97 (d, 1H), 3.15 (hept, 1H), 2.96 (s, 3H), 1.36 (d, 6H).

NMR $^1$H (300 MHz, Acetone-d$_6$) (Z) isomer (Example 34): δ 8.79 (dd, 1H), 8.52 (s, 1H), 8.29 (dd, 1H), 7.89 (d, 2H), 7.75 (d, 1H), 7.65–7.54 (m, 4H), 7.47 (dd, 1H), 7.42–7.23, (m, 5H), 7.11 (d, 1H), 3.12 (s, 3H), 3.12 (hept, 1H), 1.36 (d, 6H).

EXAMPLE 35

8-(3-{2,2-bis[4-(Methylsulfonyl)phenyl]vinyl}phenyl)-6-isopropylquinoline

Example 35 was prepared by following the procedure described for Example 30 but substituting the ketone K9 for 4,4'-dichlorobenzophenone and using the benzylphosphonate P2 as the starting materials.

NMR $^1$H (500 MHz, Acetone-d$_6$): δ 8.80 (dd, 1H), 8.29 (dd, 1H), 7.98 (d, 2H), 7.93 (d, 2H), 7.75 (d, 1H), 7.61 (d, 2H), 7.59–7.56 (m, 3H), 7.50 (d, 1H), 7.48–7.44 (m, 3H) 7.30 (t, 1H), 7.12 (d, 1H), 3.14 (hept, 1H), 3.13 (s, 3H), 2.97 (s, 3H), 1.35 (d, 6H).

EXAMPLES 36 AND 37

2-Methyl-2-[8-(3-{(E/Z)-2-(5-methyl-2-pyridinyl)-2-[4-(methylsulfonyl)phenyl]ethenyl}phenyl)-6-quinolinyl]propanenitrile Examples 36 and 37 were prepared by following the procedure described for Example 30 but substituting the ketone K8 for 4,4'-dichlorobenzophenone and substituting the benzylphosphonate P3 for P2 as the starting materials.

NMR $^1$H (500 MHz, Acetone-d$_6$) (E) isomer (Example 36): δ 8.90 (dd, 1H), 8.47 (s, 1H), 8.43 (dd, 1H), 8.08 (d, 1H), 8.00 (s, 1H), 7.97 (d, 2H), 7.83 (d, 1H) 7.57–7.53 (m, 5H), 7.50 (s, 1H), 7.28 (t, 1H), 7.06 (d, 1H), 6.96 (d, 1H), 2.96 (s, 3H), 2.33 (s, 3H), 1.88 (s, 6H).

NMR $^1$H (300 MHz, Acetone-d$_6$) (Z) isomer (Example 37): δ 8.89 (dd, 1H), 8.51 (s, 1H), 8.45 (dd, 1H), 8.09 (d, 1H), 7.89 (d, 2H), 7.72 (d, 1H), 7.62–7.56 (m, 5H), 7.43–7.42 (m, 2H) 7.30 (t, 1H), 7.25 (d, 1H), 7.10 (d, 1H), 3.11 (s, 3H), 2.34 (s, 3H), 1.87 (s, 6H).

EXAMPLE 38

2-[8-(3-{2,2-bis[4-(Methylsulfonyl)phenyl]vinyl}phenyl)-6-quinolinyl]-2-methylpropanenitrile Example 38 was prepared by following the procedure described for Example 30 but substituting the ketone K9 for 4,4'-dichlorobenzophenone and substituting the benzylphosphonate P3 for P2 as the starting materials.

NMR $^1$H (500 MHz, Acetone-d$_6$): δ 8.90 (dd, 1H), 8.44 (dd, 1H), 8.09 (d, 1H), 7.97 (d, 2H), 7.92 (d, 2H), 7.81 (d, 1H), 7.61 (d, 2H) 7.58–7.55 (m, 3H), 7.53 (s, 1H), 7.44 (s, 1H), 7.32 (t, 1H), 7.13 (d, 1H), 6.96 (d, 1H), 3.13 (s, 3H), 2.97 (s, 3H), 1.86 (s, 6H).

EXAMPLE 39

2-Methyl-2-(8-{3-[(E)-2-[4-(methylsulfonyl)phenyl]-2-(2-pyridinyl)ethenyl]phenyl}-6-quinolinyl)propanenitrile Example 39 was prepared by following the procedure described for Example 30 but substituting the ketone K10 for 4,4'-dichlorobenzophenone and substituting the benzylphosphonate P3 for P2 as the starting materials.

NMR $^1$H (300 MHz, Acetone-d$_6$): δ 8.90 (dd, 1H), 8.45 (dd, 1H), 8.11–8.09 (m, 2H), 7.84–7.80 (m, 3H), 7.72–7.69 (m, 1H), 7.63–7.52 (m, 5H), 7.43–7.38 (m, 2H), 7.33 (t, 1H) 7.28 (s, 1H), 7.14 (d, 1H), 2.97 (s, 3H), 1.86 (s, 6H).

EXAMPLES 40 AND 41

6-[1-Methyl-1-(methylsulfonyl)ethyl]-8-(3-{(E/Z)-2-(5-methyl-2-pyridinyl)-2-[4-(methylsulfonyl)phenyl]ethenyl}phenyl)quinoline Examples 41 and 42 were prepared by following the procedure described in Example 10 but substituting bromoquinoline Q3 for Q2 and substituting boronate B3 for boronate B2.

NMR $^1$H (400 MHz, Acetone-d$_6$) (E) isomer (Example 40): δ 8.91 (dd, 1H), 8.45 (s, 1H), 8.41 (dd, 1H), 8.23 (d, 1H), 8.01–8.00 (m, 2H), 7.95 (d, 2H), 7.57–7.54 (m, 4H), 7.51 (d, 1H) 7.49 (s, 1H), 7.28 (t, 1H), 7.07 (d, 1H), 6.96 (d, 1H), 2.94 (s, 3H), 2.69 (s, 3H), 2.33 (s, 3H), 1.97 (s, 6H).

NMR $^1$H (400 MHz, Acetone-d$_6$) (Z) isomer (Example 41): δ 8.88 (dd, 1H), 8.49 (s, 1H), 8.42 (dd, 1H), 8.24 (d, 1H), 7.94 (d, 1H), 7.88 (d, 2H), 7.61–7.55 (m, 5H), 7.47 (s, 1H), 7.40 (s, 1H), 7.29 (t, 1H), 7.24 (d, 1H), 7.06 (d, 1H), 3.12 (s, 3H), 2.68 (s, 3H), 2.33 (s, 3H), 1.96 (s, 6H).

EXAMPLE 42

2-(6-{(E)-2-(3-{6-[1-Methyl-1-(methylsulfonyl)ethyl]-8-quinolinyl}phenyl)-1-[4-(methylsulfonyl)phenyl]ethenyl}-3-pyridinyl)-2-propanol Example 42 was prepared by following the procedure described in Example 10 but substituting bromoquinoline Q3 for Q2 and substituting boronate B4 for boronate B2.

NMR $^1$H (500 MHz, Acetone-d$_6$): δ 8.91 (dd, 1H), 8.80 (d, 1H), 8.42 (dd, 1H), 8.23 (d, 1H), 8.03–8.01 (m, 2H), 7.96 (d, 1H), 7.82 (dd, 1H), 7.58–7.54 (m, 4H), 7.51 (s, 1H), 7.29 (t, 1H), 7.08 (d, 1H), 7.01 (d, 1H), 4.31 (s, 1H), 2.96 (s, 3H), 2.70 (s, 3H), 1.96 (s, 6H), 1.56 (s, 6H).

EXAMPLE 43

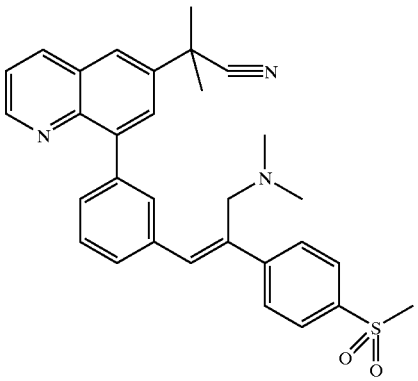

Example 43 was prepared following the procedure described previously for Examples 14 and 15 but substituting the aryl bromide AB6 for AB5 and the bromoquinoline Q5 for Q3 as the starting materials.

SALTS OF THE EXAMPLES

As discussed above, pharmaceutically acceptable salts are often desirable. Examples of such salts are described below:
General Method for Salt Preparation Salts of the compounds of this invention that are basic may be prepared in several ways:

a) The compound is dissolved in acceptable solvent such as ethyl acetate. An acceptable acid such as hydrochloric acid in an acceptable solvent such as 1,4-dioxane is then added. The precipitated salt slurry is aged and the salt is then isolated by filtration.

b) The compound and an acceptable acid such as benzenesulfonic acid are dissolved in an acceptable solvent such as isopropyl acetate or in a mixture of solvents such as isopropyl acetate and methanol. The salt may then be isolated by concentration or a solvent switch, leading to precipitation, followed by filtration. The more stable crystal form of the salt may be obtained by equilibration of the precipitated salt slurry by heating and aging prior to filtration. Seed crystals from previous batches may also be added prior to equilibration of the salt slurry, to initiate the process of crystallization and equilibration.

SULFURIC ACID SALT OF THE EXAMPLE 14 COMPOUND

The sulfuric acid salt of the example 14 compound was prepared by dissolving the compound (1.00 equiv.) in refluxing ethyl acetate. After cooling to room temperature, sulfuric acid (1.04 equiv.) was added slowly, while stirring. The resulting suspension was stirred a further 40 minutes and the solid was isolated by filtration and washed with ethyl acetate to give the sulfuric acid salt of the example 14 compound.

1H NMR (500 MHz, acetone-d$_6$): δ 9.45 (d, 1H), 9.23 (d, 1H), 8.65 (d, 1H), 8.25 (d, 1H), 8.16 (dd, 1H), 8.10 (s, 1H), 7.99 (d, 2H), 7.80 (d, 2H), 7.60 (d, 1H), 7.49 (s, 1H), 7.45 (t, 1H), 7.30 (d, 3H), 3.09 (s, 3H), 2.77 (s, 3H), 2.33 (s, 3H), 2.01 (s, 6H).

METHANESULFONIC ACID SALT OF THE EXAMPLE 14 COMPOUND

The methanesulfonic acid salt of the example 14 compound was prepared by dissolving the compound (1.0 equiv.) in refluxing ethyl acetate. After cooling to room temperature, methanesulfonic acid (1.1 equiv.) was added slowly, while stirring. The resulting suspension was stirred, allowed to concentrate by evaporation and the solid was isolated by filtration and washed with ether to give the methanesulfonic acid salt of the example 14 compound.

1H NMR (500 MHz, acetone-$d_6$): d 9.45 (d, 1H), 9.32 (d, 1H), 8.70 (s, 1H), 8.27 (s, 1H), 8.22 (t, 1H), 8.11 (s, 1H), 7.99 (d, 2H), 7.78 (d, 2H), 7.61 (d, 1H), 7.49 (m, 2H), 7.35 (d, 1H), 3.09 (s, 3H), 2.78 (s, 3H), 2.33 (s, 3H), 2.01 (s, 6H).

p-TOLUENESULFONIC ACID SALT OF THE EXAMPLE 14 COMPOUND

The p-toluenesulfonic acid salt of the example 14 compound was prepared by dissolving the compound (1.0 equiv.) in refluxing ethyl acetate. After cooling to room temperature, p-toluenesulfonic acid (1.1 equiv.) in ethyl acetate was added slowly. The solution was concentrated and the suspension was aged with stirring and periodic sonication at room temperature for 3 days. The solid was then isolated by filtration and washed with ethyl acetate to give the p-toluenesulfonic acid salt of the example 14 compound).

mp 184–185° C.

1H NMR (500 MHz, acetone-$d_6$): δ 9.58 (d, 1H), 9.22 (d, 1H), 8.63 (s, 1H), 8.23 (d, 1H), 8.16 (m, 1H), 8.03 (s, 1H), 7.94 (d, 2H), 7.73 (d, 2H), 7.55 (m, 3H), 7.45 (s, 1H), 7.40 (t, 1H), 7.27 (d, 1H), 7.12 (d, 2H), 3.07 (s, 3H), 2.75 (s, 3H), 2.33 (s, 3H), 2.29 (s, 3H), 2.01 (s, 6H).

2-NAPHTHALENESULFONIC ACID SALT OF THE EXAMPLE 14 COMPOUND

The 2-naphthalenesulfonic acid salt of the example 14 compound was prepared by dissolving the compound (1.0 equiv.) in refluxing ethyl acetate. After cooling to room temperature, 2-naphthalenesulfonic acid (1.1 equiv.) in ethyl acetate was added slowly, followed by ethanol. Toluene was then added to the solution, followed by concentration. More toluene was then added and the suspension was aged with stirring and periodic sonication at room temperature for 24 h. The solid was then isolated by filtration and washed with toluene to give the 2-naphthalenesulfonic acid salt of the example 14 compound.

mp 202–204° C.

1H NMR (500 MHz, acetone-$d_6$): δ 9.64 (d, 1H), 9.30 (d, 1H), 8.67 (d, 1H), 8.25 (d, 1H), 8.23 (m, 1H), 8.16 (s, 1H), 7.99 (s, 1H), 7.91 (d, 2H), 7,87 (m, 2H), 7.82 (d, 1H), 7.72 (dd, 1H), 7.68 (d, 2H), 7.54 (d, 1H), 7.52 (m, 2H), 7.43 (brs, 1H), 7.37 (t, 1H), 7.22 (d, 1H), 3.03 (s, 3H), 2.76 (s, 3H), 2.33 (s, 3H), 2.02 (s, 6H).

HYDROCHLORIDE SALT OF THE EXAMPLE 43 COMPOUND

The hydrochloride salt of the example 43 compound was prepared by dissolving the compound (1.0 equiv.) in ethyl acetate with heating and sonication. After cooling the solution to room temperature, HCl in 1,4-dioxane (4M, 1.0 equiv.) was added while stirring. The suspension was stirred for a further 5 minutes and the solid was isolated by filtration to give the mono-hydrochloride salt of the example 43 compound.

BENZENESULFONIC ACID SALT OF THE EXAMPLE 14 COMPOUND

The benzenesulfonic acid salt of the Example 14 compound is available in two crystalline forms ("Form A" and "Form B"). The forms are produced by the following procedures:

Salt Formation

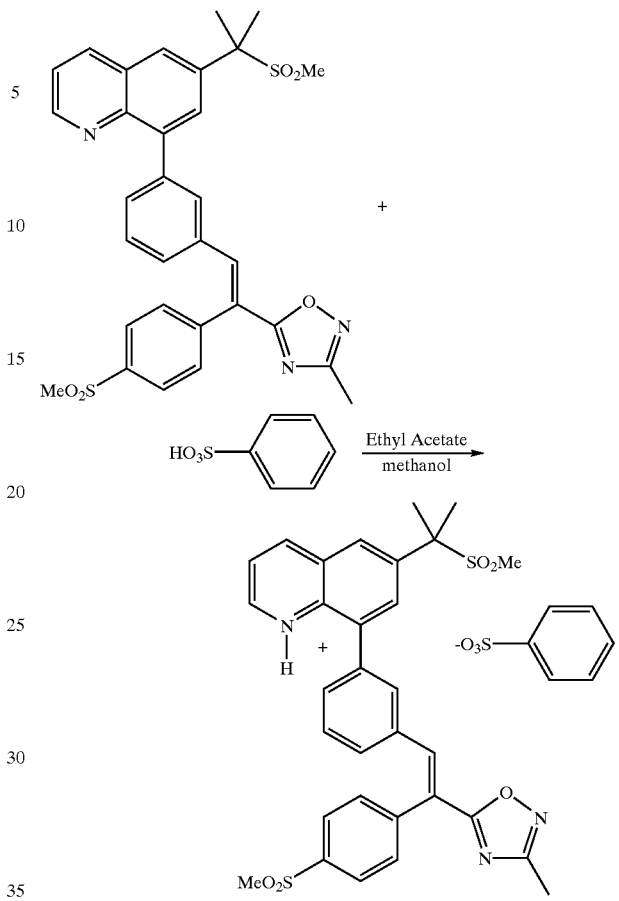

Form A

To a slurry of the Example 14 compound (1 equiv.) in ethyl acetate was added benzenesulfonic acid (1–1.2 equiv.). Other esters may be used in place of ethyl acetate. Methanol was added and the resulting mixture was heated until the solid dissolved. Other alcohols such as ethanol or propanol may be used in place of the methanol.

The resulting solution was filtered and concentrated. The product crystallized during concentration. The resulting mixture was diluted with ethyl acetate and aged. The yellow solid was collected by filtration.

HPLC indicated a 1:1 molar ratio of 6-[1-methyl-1-(methylsulfonyl)ethyl]-8-[3-[(E)-2-[3-methyl-1,2,4-oxadiazol-5-yl]-2-[4-(methylsulfonyl)phenyl]ethenyl]phenyl]quinoline and benzenesulfonic acid.

m.p. by DSC: 193° C.

Figure 2:
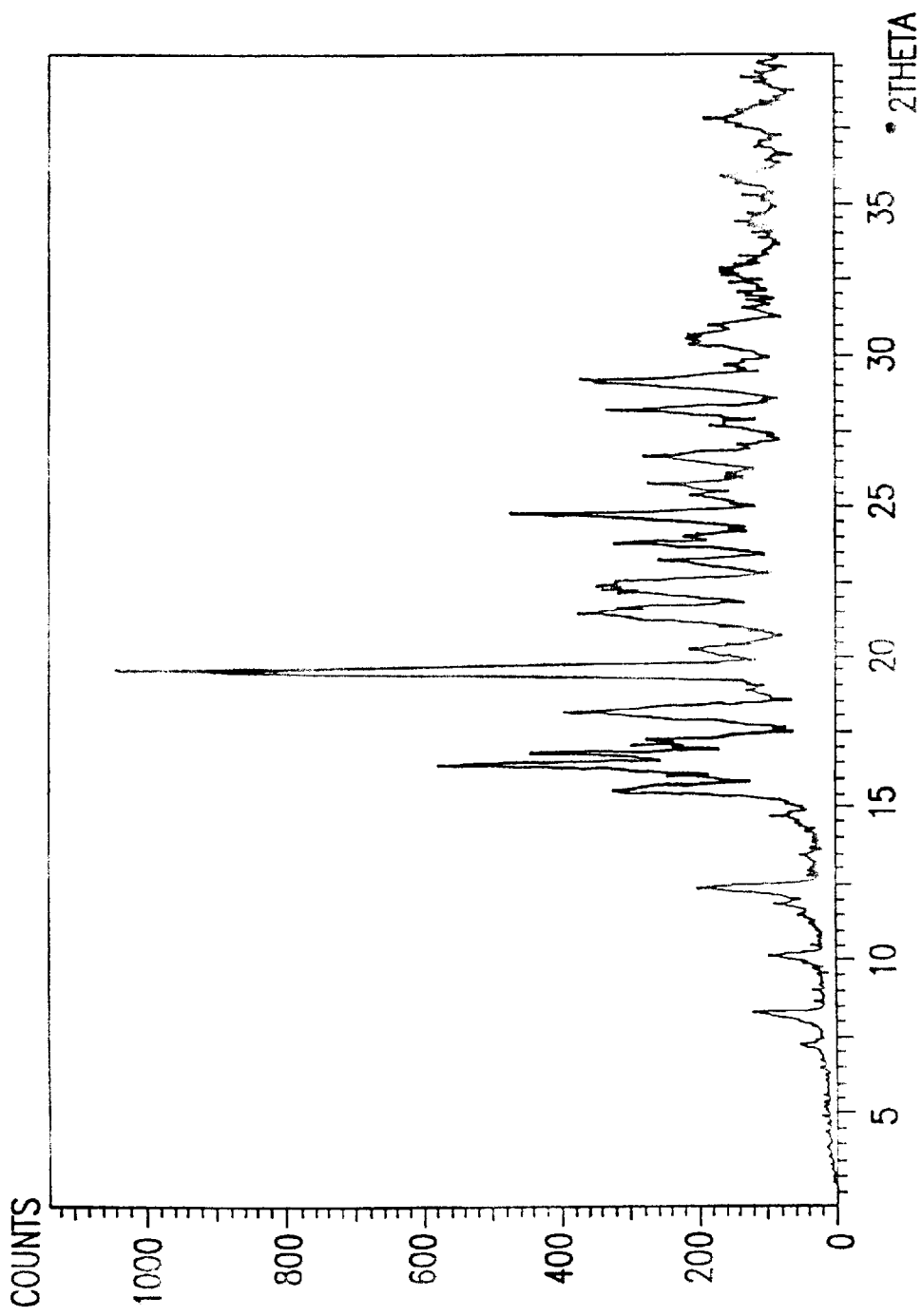
FIG. 2 is a graph of Counts against °Theta for an X-ray Powder Diffraction of the Form A polymorph of the benzenesulfonic acid salt of 6-[1-methyl-1-(methylsulfonyl) ethyl]-8-[3-[(E)-2-[3-methyl-1,2,4-oxadiazol-5-yl]-2-[4-(methylsulfonyl)phenyl]ethenyl]phenyl]quinoline.
Figure 5:
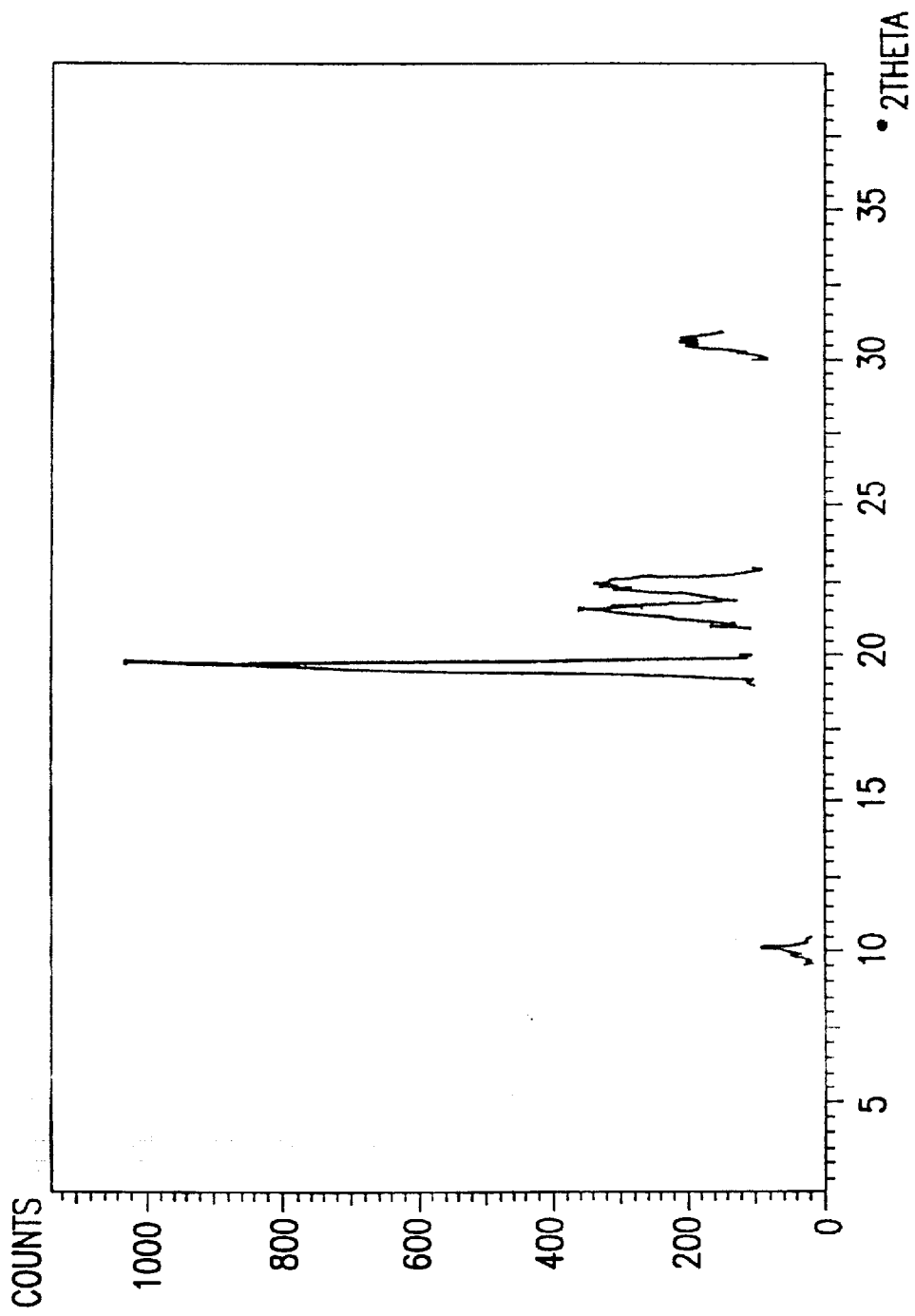
FIG. 5 is a graph of the distinguishing feature peaks of the X-ray Powder Diffraction of the Form A polymorph of the benzenesulfonic acid salt of 6-[1-methyl-1-(methylsulfonyl) ethyl]-8-[3-[(E)-2-[3-methyl-1,2,4-oxadiazol-5-yl]-2-[4-(methylsulfonyl)phenyl]ethenyl]phenyl]quinoline.

The X-ray Powder Diffraction ("XRPD") Spectrogram for the Form A is shown in FIG. 2. The identifying peaks are tabulated below and shown in FIG. 5.

| Peaks Identifying Form A Polymorph (°2 Theta) |
| --- |
| 10.0 |
| 19.5 |
| 21.4 |
| 22.4 |
| 30.5 |

Form B

To a slurry of the Example 14 compound (1 equiv.) in a mixture of isopropyl acetate (i-PrOAc) and methanol (1:1) was added benzenesulfonic acid (1–1.2 equiv.). Other esters may be used in place of i-PrOAc and other alcohols such as ethanol or propanol may be used in place of methanol. The mixture was aged at 20–50° C. until the solids dissolved. The resulting solution was filtered and distilled while the volume was maintained by addition of a 9:1 (v/v) mixture of i-PrOAc/methanol. The product crystallized during the distillation.

The resulting mixture was aged at 20–70° C. for 2–10 h to ensure complete formation of Form B. The resulting off-white solid was isolated by filtration and dried.

HPLC indicated a 1:1 molar ratio of 6-[1-methyl-1-(methylsulfonyl)ethyl]-8-[3-[(E)-2-[3-methyl-1,2,4-oxadiazol-5-yl]-2-[4-(methylsulfonyl)phenyl]ethenyl]phenyl]quinoline and benzenesulfonic acid.

m.p. by DSC: 210° C.

Figure 3:
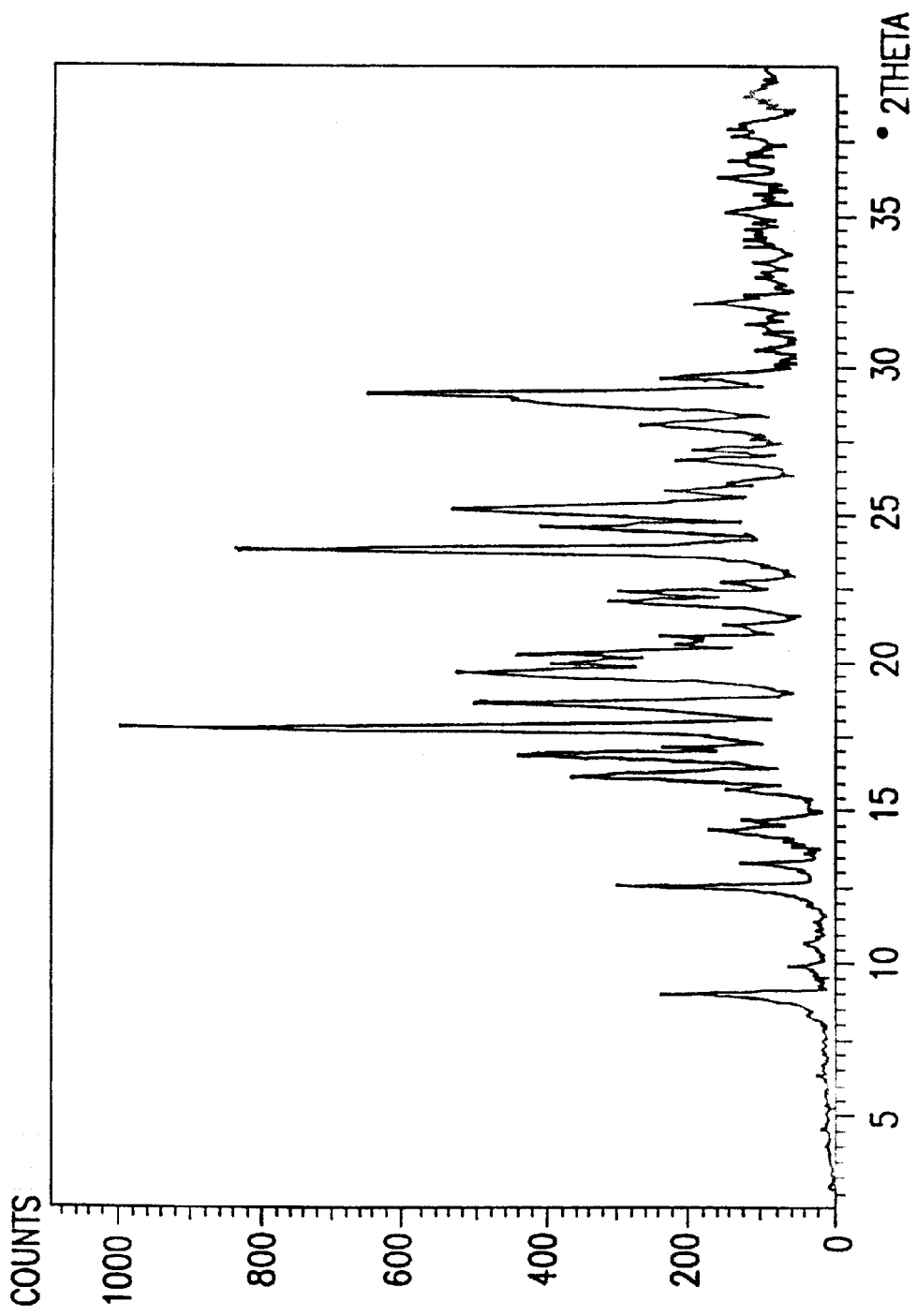
FIG. 3 is a graph of Counts against °Theta for an X-ray Powder Diffraction of the Form B polymorph of the benzenesulfonic acid salt of 6-[1-methyl-1-(methylsulfonyl) ethyl]-8-[3-[(E)-2-[3-methyl-1,2,4-oxadiazol-5-yl]-2-[4-(methylsulfonyl)phenyl]ethenyl]phenyl]quinoline.
Figure 4:
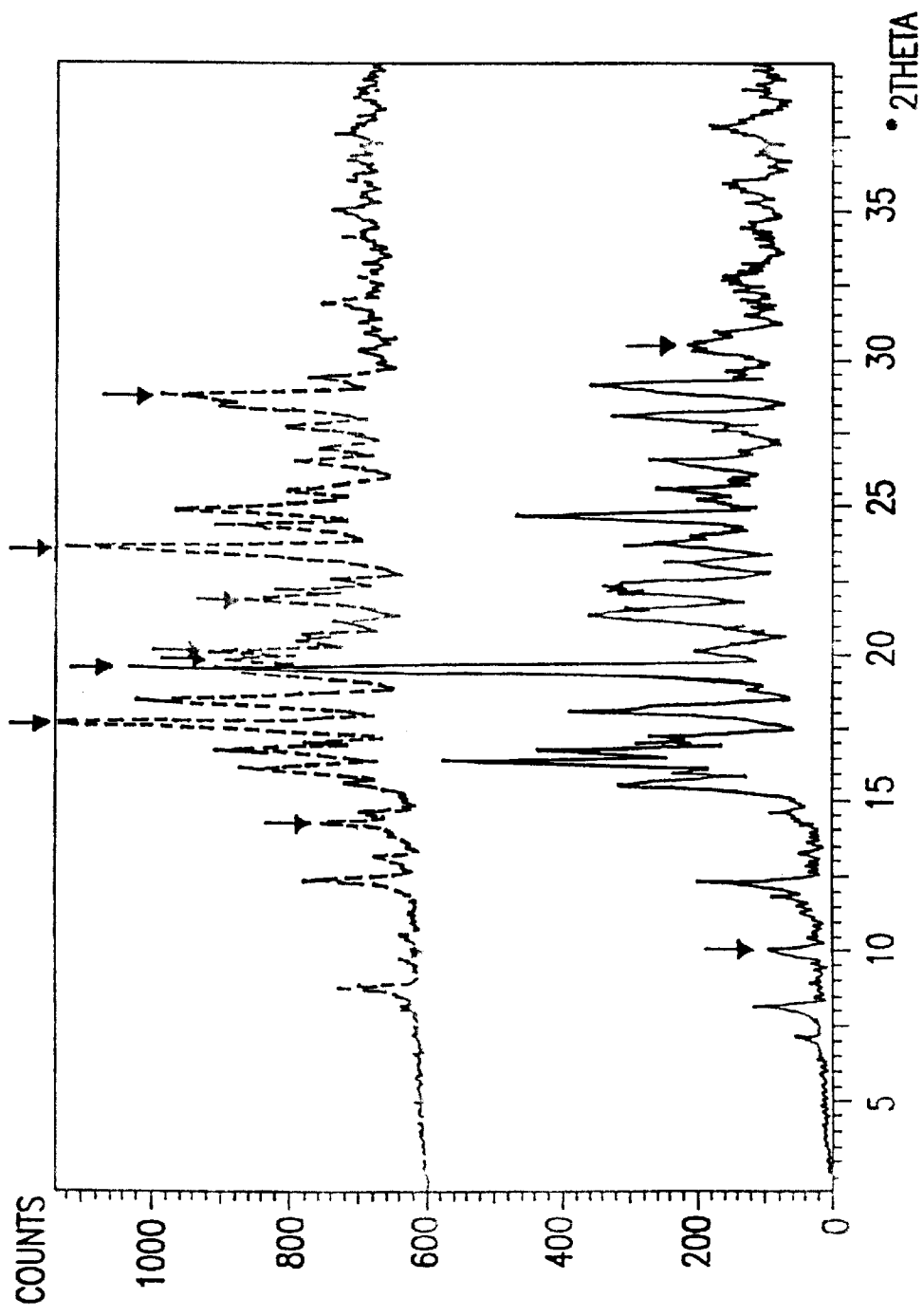
FIG. 4 is a comparison of the X-ray Powder Diffractions of the Form A polymorph (bottom trace) and the Form B (upper trace) of the benzenesulfonic acid salt of 6-[1-methyl-1-(methylsulfonyl)ethyl]-8-[3-[(E)-2-[3-methyl-1,2, 4-oxadiazol-5-yl]-2-[4-(methylsulfonyl)phenyl]ethenyl] phenyl]quinoline.
Figure 6:
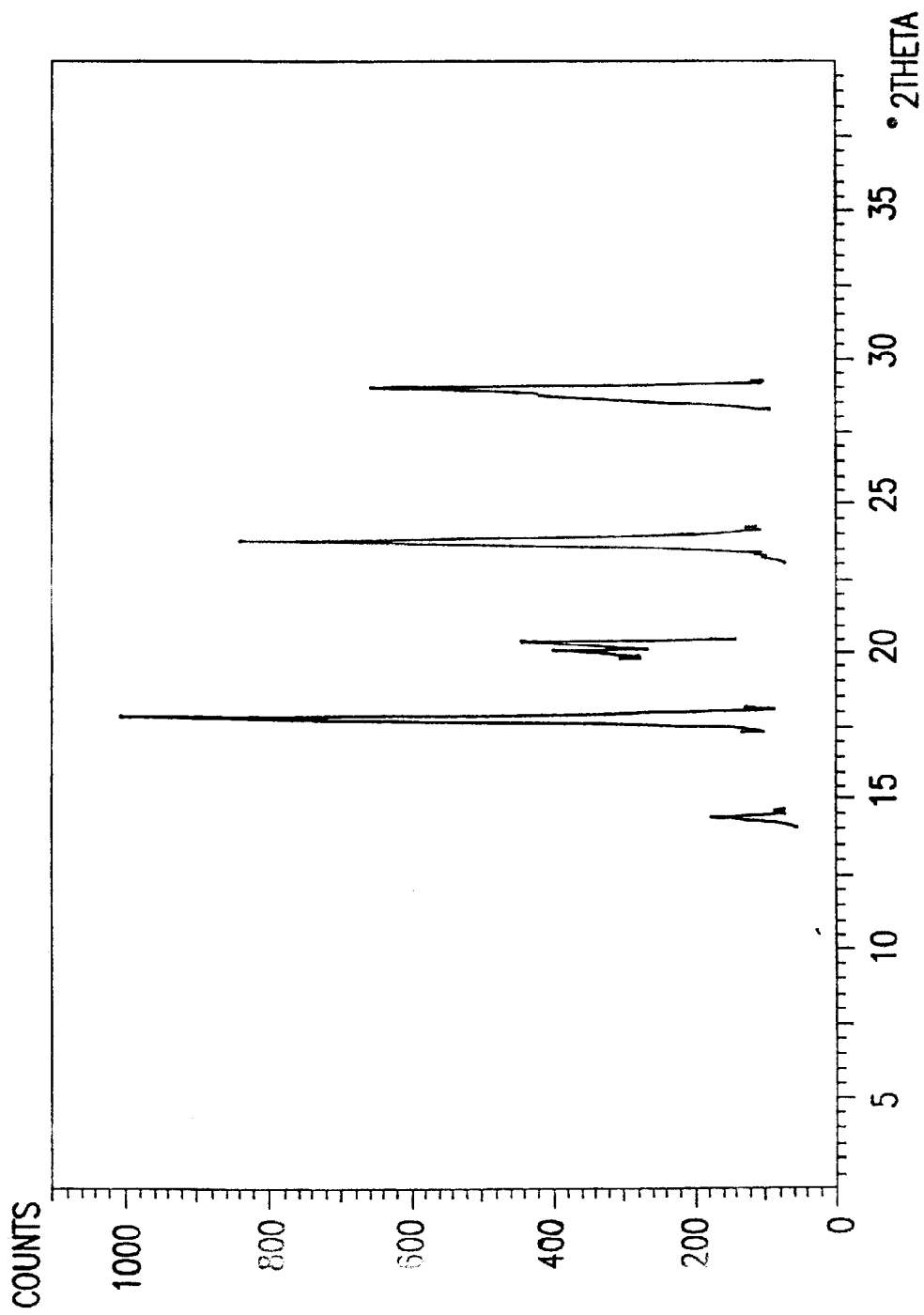
FIG. 6 is a graph of the distinguishing feature peaks of the X-ray Powder Diffraction of the Form B polymorph of the benzenesulfonic acid salt of 6-[1-methyl-1-(methylsulfonyl) ethyl]-8-[3-[(E)-2-[3-methyl-1,2,4-oxadiazol-5-yl]-2-[4-(methylsulfonyl)phenyl]ethenyl]phenyl]quinoline.

The XRPD Spectrogram for the Form B is shown in FIG. 3. The identifying peaks are tabulated below and shown in FIG. 6. The spectra are compared in FIG. 4 with the identifying peaks pointed out by arrows.

| Peaks Identifying Form B Polymorph (°2 Theta) |
| --- |
| 14.4 |
| 17.7 |
| 20.0 |
| 20.2 |
| 23.7 |
| 28.9 |

Other variations or modifications, which will be obvious to those skilled in the art, are within the scope and teachings of this invention. This invention is not to be limited except as set forth in the following claims.

What is claimed is:

1. A compound comprising the benzenesulfonic acid salt of

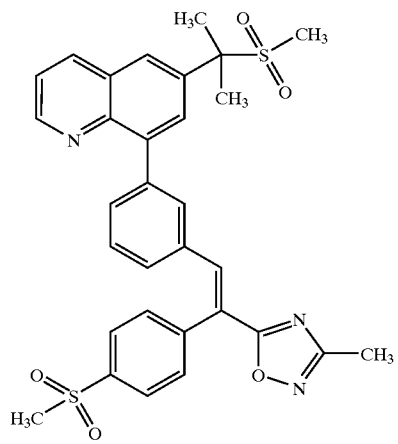

characterized by identifying peaks:

| Peaks Identifying Form B Polymorph (°2 Theta) |
| --- |
| 14.4 |
| 17.7 |
| 20.0 |
| 20.2 |
| 23.7 |
| 28.9 | in an X-ray powder diffraction spectrogram.

2. A compound comprising the benzenesulfonic acid salt of

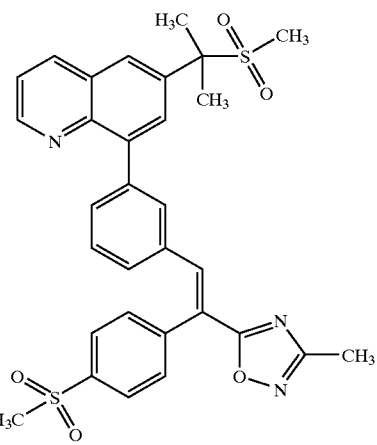

characterized by identifying peaks:

| Peaks Identifying Form A Polymorph (°2 Theta) |
| --- |
| 10.0 |
| 19.5 |
| 21.4 |
| 22.4 |
| 30.5 | in an X-ray powder diffraction spectrogram.

3. A method of treatment of asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues comprising the step of administering a therapeutically effective amount, or a prophylactically effective amount, of the pharmaceutically acceptable salt according to claim 1.

4. A method of treatment of asthma, chronic bronchitis, chronic obstructive pulmonary disease (COPD), eosinophilic granuloma, psoriasis and other benign or malignant proliferative skin diseases, endotoxic shock (and associated conditions such as laminitis and colic in horses), septic shock, ulcerative colitis, Crohn's disease, reperfusion injury of the myocardium and brain, inflammatory arthritis, osteoporosis, chronic glomerulonephritis, atopic dermatitis, urticaria, adult respiratory distress syndrome, infant respiratory distress syndrome, chronic obstructive pulmonary disease in animals, diabetes insipidus, allergic rhinitis, allergic conjunctivitis, vernal conjunctivitis, arterial restenosis, atherosclerosis, neurogenic inflammation, pain, cough, rheumatoid arthritis, ankylosing spondylitis, transplant rejection and graft versus host disease, hypersecretion of gastric acid, bacterial, fungal or viral induced sepsis or septic shock, inflammation and cytokine-mediated chronic tissue degeneration, osteoarthritis, cancer, cachexia, muscle wasting, depression, memory impairment, monopolar depression, acute and chronic neurodegenerative disorders with inflammatory components, Parkinson disease, Alzheimer's disease, spinal cord trauma, head injury, multiple sclerosis, tumour growth and cancerous invasion of normal tissues comprising the step of administering a therapeutically effective amount, or a prophylactically effective amount, of the pharmaceutically acceptable salt according to claim 2.

* * * * *